US008198456B2

(12) United States Patent
Adler et al.

(10) Patent No.: US 8,198,456 B2
(45) Date of Patent: Jun. 12, 2012

(54) DIHYDROPYRIDINE DERIVATIVES AS USEFUL AS PROTEIN KINASE INHIBITORS

(75) Inventors: Marc Adler, Orinda, CA (US); Stefan Baeurle, Berlin (DE); Judi Bryant, Mill Valley, CA (US); Ming Chen, Somerville, MA (US); Yuo-Ling Chou, Lafayette, CA (US); Paul Hrvatin, Concord, CA (US); Seock-Kyu Khim, Orinda, CA (US); Monica Kochanny, Benicia, CA (US); Wheeseong Lee, Orinda, CA (US); Michael Mamounas, Oakland, CA (US); Janet Meurer Ogden, Fairfield, CA (US); Gary Bruce Phillips, Pleasant Hill, CA (US); Victor Selchau, Concord, CA (US); Christopher West, El Sobrante, CA (US); Bin Ye, Moraga, CA (US); Shendong Yuan, San Ramon, CA (US); Martin Krueger, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 1171 days.

(21) Appl. No.: 11/955,777

(22) Filed: Dec. 13, 2007

(65) Prior Publication Data

US 2008/0176833 A1 Jul. 24, 2008

Related U.S. Application Data

(60) Provisional application No. 60/875,124, filed on Dec. 14, 2006.

(51) Int. Cl.
*C07D 401/04* (2006.01)
(52) U.S. Cl. .................................................... 546/275.7
(58) Field of Classification Search ............... 546/275.7; 514/339
See application file for complete search history.

(56) References Cited

U.S. PATENT DOCUMENTS

| 3,969,359 | A | 7/1976 | Kuthan et al. |
| 6,265,127 | B1 | 7/2001 | Wilson et al. |
| 2007/0191409 | A1 | 8/2007 | Mullan et al. |
| 2007/0232633 | A1 | 10/2007 | Kompella et al. |
| 2007/0293491 | A1 | 12/2007 | Shafer et al. |

FOREIGN PATENT DOCUMENTS

| EP | 0755931 | | 1/1997 |
| WO | WO 2003/087026 | | 10/2003 |
| WO | WO 2005/005378 | | 1/2005 |
| WO | 2006/066011 | * | 6/2006 |
| WO | WO 2006074419 A3 | | 7/2006 |

OTHER PUBLICATIONS

Database CA [Online] Chemical Abstracts Service, Columbus, Ohio, US; XP002475969 retrieved from STN, database accession No. 1996: 442010, compounds with CAS registry No. 180888-06-6, 180888-11-3, 180888-30-6.
Database CA [Online] Chemical Abstracts Service, Columbus, Ohio, US; XP002475970 retrieved from STN, database accession No. 1994: 217523, compounds with CAS registry No. 153901-35-0, 153901-36-1.
Database CA [Online] Chemical Abstracts Service, Columbus, Ohio, US; XP002475971 retrieved from STN, database accession No. 1992: 591655, compounds with CAS registry No. 130422-56-9, 130422-57-0, 143813-66-5.
Database CA [Online] Chemical Abstracts Service, Columbus, Ohio, US; XP002475972 retrieved from STN, database accession No. 1988: 630744, compounds with CAS registry No. 117772-29-9.
Database CA [Online] Chemical Abstracts Service, Columbus, Ohio, US; XP002475973 retrieved from STN, database accession No. 1987: 636462, compounds with CAS registry No. 109329-72-8, 111564-27-3, 35929-86-3, 111564-26-2.
Database CA [Online] Chemical Abstracts Service, Columbus, Ohio, US; XP002475974 retrieved from STN, database accession No. 1985: 203849, compounds with CAS registry No. 96336-23-1.
Database CA [Online] Chemical Abstracts Service, Columbus, Ohio, US; XP002475975 retrieved from STN, database accession No. 1985: 185036, compounds with CAS registry No. 82921-30-0.
Database BNF [Online] British Non-Ferrous Metals Technology Centre, Wantage, GB; XP002475976 retrieved from STN, database accession No. 1984: 472686, compounds with CAS registry No. 91206-60-9.
Database CA [Online] Chemical Abstracts Service, Columbus, Ohio, US; XP002475977 retrieved from STN, database accession No. 1984: 191135, compounds with CAS registry No. 35929-86-3, 9005862-1.
Database CA [Online] Chemical Abstracts Service, Columbus, Ohio, US; XP002475978 retrieved from STN, database accession No. 1984: 85560, compounds with CAS registry No. 88876-77-1, 8887681-7.
Database CA [Online] Chemical Abstracts Service, Columbus, Ohio, US; XP002475979 retrieved from STN, database accession No. 1982: 527451, compounds with CAS registry No. 82921-31-1.

(Continued)

*Primary Examiner* — Patricia Morris

(57) ABSTRACT

This invention provides novel dihydropyridine derivatives of the formula I

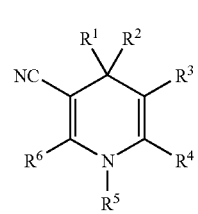

having protein tyrosine kinase inhibitory activity, to process for the manufacture thereof and to the use thereof for the treatment of c-Met-mediated diseases or c-Met-mediated conditions.

10 Claims, No Drawings

OTHER PUBLICATIONS

Database CA [Online] Chemical Abstracts Service, Columbus, Ohio, US; XP002475980 retrieved from STN, database accession No. 1978: 508971, compounds with CAS registry No. 35929-86-3, 67438-98-6, 67438-99-7, 67439-00-3, 67439-03-6, 67439-06-9, 67439-07-0, 67439-09-2.

Database CA [Online] Chemical Abstracts Service, Columbus, Ohio, US; XP002475981 retrieved from STN, database accession No. 1977: 535104, compounds with CAS registry No. 64089-23-2, 64089-24-3, 64089-25-4, 64089-26-5, 64089-27-6, 64089-28-7.

Database CA [Online] Chemical Abstracts Service, Columbus, Ohio, US; XP002475982 retrieved from STN, database accession No. 1977: 72447, compounds with CAS registry No. 61322-83-6, 61322-85-8, 61322-86-9, 61322-87-0.

Database CA [Online] Chemical Abstracts Service, Columbus, Ohio, US; XP002475983 retrieved from STN, database accession No. 1956: 74000, compounds with CAS registry No. 345237-13-0, 874492-74-7, 874492-75-8.

Cui J. J., "Inhibitors targeting hepatocyte growth factor receptor and their potential therapeutic applications", Expert Opinion on Therapeutic Patents, vol. 17, No. 9, 2007, pp. 1035-1045, XP002475968.

International Preliminary Report on Patentability for PCT/EP2007/011076 dated Jun. 16, 2009.

* cited by examiner

DIHYDROPYRIDINE DERIVATIVES AS USEFUL AS PROTEIN KINASE INHIBITORS

This application claims the benefit of the filing date of U.S. Provisional Application Ser. No. 60/875,124, filed Dec. 14, 2006.

This invention relates to novel dihydropyridine derivatives having protein tyrosine kinase inhibitory activity, to a process for the manufacture thereof and to the use thereof for the treatment of c-Met-mediated diseases or c-Met-mediated conditions.

In the past two decades numerous avenues of research have demonstrated the importance of receptor tyrosine kinase (RTK)-mediated signaling in the regulation of mammalian cell growth. Recently, results have been achieved in the clinic with selective small-molecule inhibitors of tyrosine kinases as anti-tumorigenic agents.

c-Met is a receptor tyrosine kinase (RTK) that is encoded by the Met proto-oncogene and transduces the biological effects of hepatocyte growth factor (HGF), which is also referred to as scatter factor (SF) [Jiang et al. *Crit. Rev. Oncol. Hematol.* 29: 209-248 (1999)]. c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). In addition to its effects on epithelial cells, HGF/SF has been reported to be an angiogenic factor, and c-Met signaling in endothelial cells can induce many of the cellular responses necessary for angiogenesis (proliferation, motility, invasion).

The c-Met receptor and HGF are frequently overexpressed, and constitutively active, in numerous human cancers. Indeed, published data has demonstrated that overexpression of c-Met and/or HGF is often a negative prognostic indicator for an array of solid tumor types, including lung, liver, gastric and breast. Similarly, multiple in vitro and in vivo data suggest that the c-Met RTK plays a critical role in growth regulation of tumors and spread of metastases. Importantly, in vivo experiments have shown that anti-c-Met or -HGF ribozymes, anti-HGF monoclonal antibodies, HGF peptide antagonists and small-molecule kinase inhibitors against c-Met cause significant tumor regression in a variety of animal tumor models. c-Met has also been directly implicated in cancers without a successful treatment regimen, such as pancreatic cancer, glioma, and hepatocellular carcinoma. Moreover, in humans, a causal link between c-Met activation and tumorigenesis has been established in hereditary renal cell carcinoma (HPRC), demonstrating that c-Met-activating mutations directly result in the formation of these tumors and are the primary defect in these patients.

In view of the impact of c-Met activation on tumorigenesis and the recent success with tyrosine kinase inhibitors in the clinic, it would be desirable to develop a small-molecule inhibitor of the c-Met kinase as a therapeutic agent for multiple solid tumor types and for other proliferative disorders, particularly given the inadequate treatments currently available for the majority of the disorders implicated in its activation.

c-Met inhibitors have been disclosed in WO 2004/076412 and WO 2006/021881 and have recently been reviewed [J. J. Cui, Expert Opin. Ther. Patents (2007) 17(9): 1035-1045].

In view of the prior art, the objective technical problem to be solved according to the present invention may therefore be seen in providing alternative compounds having an inhibitory activity on the c-Met kinase.

The technical problem has been solved according to the present invention by the provision of novel compounds of the formula I

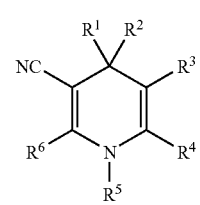

wherein, $R^1$ is hydrogen, optionally substituted alkyl, optionally substituted haloalkyl, optionally substituted hydroxyalkyl, or optionally substituted alkoxyalkyl;

$R^2$ is selected from the groups:

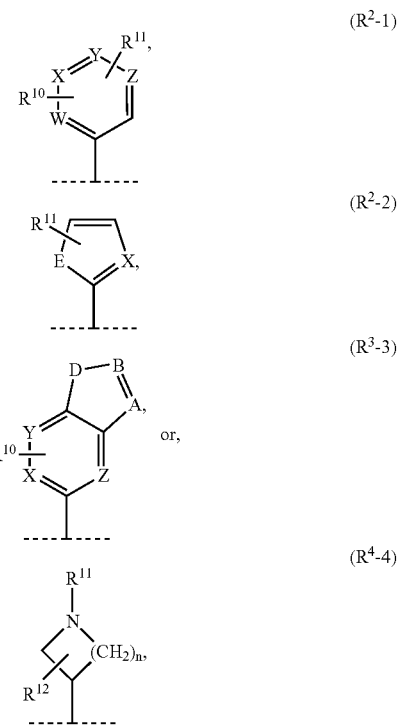

in which

A and B are each independently C—$R^{11}$ or N;

D and E are each independently N—$R^{12}$, O, or S;

W, X, Y, and Z are each independently C—$R^{11}$, C—$R^{14}$, or N;

n=1, 2 or 3;

$R^3$ is hydrogen, cyano, optionally substituted alkyl, optionally substituted alkenyl, or optionally substituted alkynyl;

$R^4$ is haloalkyl, $R^7$, $R^7$-aminocycloalkyl, $R^7$-aminocycloalkenyl, aryl, heteroaryl, —$(CH_2)_m NR^8 R^9$, or —C(=O)O$R^8$;

$R^5$ is hydrogen, optionally substituted aralkyl, optionally substituted hydroxyalkyl, $R^7$, —C(=O)$OR^8$—$CH_2$C(=O)$NR^8R^9$, or —$(CH_2)_m NR^8R^9$;
or
$R^4$ and $R^5$ together form an alkylene bridge;
$R^6$ is $C_{1-3}$alkyl or amino;
$R^7$ is optionally substituted alkyl, optionally substituted cycloalkyl, optionally substituted cycloalkenyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl;
$R^8$ is hydrogen or optionally substituted alkyl;
$R^9$ is hydrogen, or optionally substituted alkyl;
$R^{10}$ is hydrogen, hydroxy, halo, amino, —C(=O)$OR^8$, —CH(=$NOR^8$), —$NR^8R^9$, optionally substituted alkyl, or optionally substituted aryl;
$R^{11}$ in each instance is independently hydrogen, halo, amino, optionally substituted alkyl, optionally substituted alkenyl, optionally substituted alkynyl, optionally substituted cycloalkyl, optionally substituted cycloalkylalkyl, —C(=O)$OR^8$, —C(=O)$NR^8R^9$, —CH(=$NOR^8$), —NHC(=O)$R^7$, —NHC(=O)$NHR^7$, —NHC(=O)$OR^7$, —$NHR^7$, —N=$CHR^7$, optionally substituted aryl, optionally substituted aralkyl, optionally substituted heteroaryl, optionally substituted heteroaralkyl, optionally substituted heterocyclyl, or optionally substituted heterocyclylalkyl;
$R^{12}$ is hydrogen, amino, optionally substituted alkyl, optionally substituted alkenyl, optionally substituted alkynyl, optionally substituted cycloalkyl, optionally substituted cycloalkylalkyl, —C(=O)$OR^8$, —C(=O)$NR^8R^9$, —CH(=$NOR^8$), —NHC(=O)$R^7$, —NHC(=O)$NHR^7$, —NHC(=O)$OR^7$, —$NHR^7$, —N=$CHR^7$, optionally substituted aryl, optionally substituted aralkyl, optionally substituted heteroaryl, optionally substituted heteroaralkyl, optionally substituted heterocyclyl, or optionally substituted heterocyclylalkyl;
$R^{14}$ in each instance is independently hydrogen, halo, amino, optionally substituted alkyl, optionally substituted alkenyl, optionally substituted alkynyl, optionally substituted cycloalkyl, optionally substituted cycloalkylalkyl, —C(=O)$OR^8$, —C(=O)$NR^8R^9$, —CH(=$NOR^8$), —NHC(=O)$R^7$, —NHC(=O)$NHR^7$, —NHC(=O)$OR^7$, —$NHR^7$, —N=$CHR^7$, optionally substituted aryl, optionally substituted aralkyl, optionally substituted heteroaryl, optionally substituted heteroaralkyl, optionally substituted heterocyclyl, optionally substituted heterocyclylalkyl, or —$R^{16}$—C(=O)N$(R^{15})_2$;
$R^{15}$ in each instance is independently hydrogen, alkyl, haloalkyl, cycloalkyl, cycloalkylalkyl, aryl, aralkyl, heterocyclyl, heterocyclylalkyl, heteroaryl or heteroaralkyl, where each of the above substituents may be optionally substituted as defined herein;
$R^{16}$ in each instance is independently a direct bond or a straight or branched alkylene or alkenylene chain, where each of the above substituents may be optionally substituted as defined herein; preferably $R^{16}$ is a direct bond;
m is 0, 1, 2, 3 or 4;
provided that, when $R^1$ and $R^5$ are hydrogen, $R^3$ is cyano, and $R^4$ and $R^6$ are methyl,
then $R^2$ cannot be 4-hydroxyphenyl; or their pharmaceutically acceptable derivatives or salts.

The present invention covers compounds of formula I in form of single stereoisomers or as mixtures of stereoisomers thereof, as well as their pharmaceutically acceptable derivatives or salts.

In a further aspect, this invention provides a pharmaceutical composition, which composition comprises a therapeutically effective amount of a compound of formula I as described above and a pharmaceutically acceptable excipient.

In another aspect, this invention provides a method of treating a disease, disorder or condition ameliorated by the inhibition of c-Met kinase activity in a mammal, wherein the method comprises administering to a mammal in need thereof a therapeutically effective amount of a compound of formula I as described above. Such diseases, disorders or conditions include, but are not limited to, cancers and other proliferative disorders. The compounds provided by this invention are also useful for the study of kinases in biological and pathological phenomena; the study of intracellular signal transduction pathways mediated by such kinases; and the comparative evaluation of new kinase inhibitors.

DEFINITIONS

Throughout this specification and the claims that follow, unless the context requires otherwise, the word "comprise", and variations such as "comprises" and "comprising", will be understood to imply the inclusion of a stated component or step or group of components or steps but not the exclusion of any other component or step or group of components or steps. As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Furthermore, as used in the specification and appended claims, unless specified to the contrary, the following terms have the meaning indicated:

"Amino" refers to the —$NH_2$ radical.
"Cyano" refers to the —CN radical.
"Hydroxy" refers to the —OH radical.
"Nitro" refers to the —$NO_2$ radical.
"Oxo" refers to the =O radical.
"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one or more substituents independently selected from halo, cyano, nitro, oxo, trimethylsilyl, —$OR^{15}$, —OC(=O)$R^{15}$, —N$(R^{15})_2$, —C(=O)$R^{15}$—C(=O)$OR^{15}$, —C(=O)N$(R^{15})_2$, —N$(R^{15})$C(=O)$OR^{15}$, —N$(R^{15})$C(=O)$R^{15}$, —N$(R^{15})$S(=O)$_t R^{15}$ (where t is 1 or 2), —S(=O)$_t OR^{15}$ (where t is 1 or 2), —S(=O)$_p R^{15}$ (where p is 0, 1 or 2), or —S(=O)$_t$N$(R^{15})_2$ (where t is 1 or 2) where each $R^{15}$ is independently hydrogen, alkyl, haloalkyl, cycloalkyl, cycloalkylalkyl, aryl, aralkyl, heterocyclyl, heterocyclylalkyl, heteroaryl or heteroaralkyl, and where each of the above substituents may be optionally substituted as defined herein.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl group may be optionally substituted by one or more substituents independently selected from cyano, nitro, oxo, trimethylsilyl, —OR$^{15}$, —OC(=O)—R$^{15}$, —N(R$^{15}$)$_2$, —C(=O)R$^{15}$, —C(=O)OR$^{15}$, —C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and where each of the above substituents may be optionally substituted as defined herein.

"Alkynyl" refers to a straight or branched hydrocarbon chain radical group consisting solely of carbon and hydrogen atoms, containing at least one triple bond, optionally containing at least one double bond, having from two to twelve carbon atoms, preferably two to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one or more substituents independently selected from cyano, nitro, oxo, trimethylsilyl, —OR$^{15}$, —OC(=O)—R$^{15}$, —N(R$^{15}$)$_2$, —C(=O)R$^{15}$, —C(=O)OR$^{15}$, —C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and where each of the above substituents may be optionally substituted as defined herein.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like.

The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one or more substituents independently selected from halo, cyano, nitro, aryl, cycloalkyl, heterocyclyl, heteroaryl, oxo, trimethylsilyl, —OR$^{15}$, —OC(=O)—R$^{15}$, —N(R$^{15}$)$_2$, —C(=O)R$^{15}$, —C(=O)OR$^{15}$—C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and where each of the above substituents may be optionally substituted as defined herein.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one or more substituents independently selected from halo, cyano, nitro, aryl, cycloalkyl, heterocyclyl, heteroaryl, oxo, trimethylsilyl, —OR$^{15}$, —OC(=O)—R$^{15}$, —N(R$^{15}$)$_2$, —C(=O)R$^{15}$, —C(=O)R —C(=O)N(R)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and where each of the above substituents may be optionally substituted as defined herein.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one or more substituents independently selected from alkyl, alkenyl, halo, haloalkenyl, cyano, nitro, aryl, cycloalkyl, heterocyclyl, heteroaryl, oxo, trimethylsilyl, —OR$^{15}$, —OC(=O)—R$^{15}$, —N(R$^{15}$)$_2$, —C(=O)R$^{15}$, —C(=O)OR$^{15}$, —C(=O)N(R$^{15}$)$_2$, —N(R$^{15}$)C(=O)OR$^{15}$, —N(R$^{15}$)C(=O)R$^{15}$, —N(R$^{15}$)S(=O)$_t$R$^{15}$ (where t is 1 or 2), —S(=O)$_t$OR$^{15}$ (where t is 1 or 2), —S(=O)$_p$R$^{15}$ (where p is 0, 1 or 2), and —S(=O)$_t$N(R$^{15}$)$_2$ (where t is 1 or 2) where each R$^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and where each of the above substituents may be optionally substituted as defined herein.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$, $R^{16}$—$N(R^{15})_2$, —$R^{16}$—$C(=O)R^{15}$-$R^{16}$—$C(=O)OR^{15}$, —$R^{16}$—$C(=O)N(R^{15})_2$, —$R^{16}$—$N(R^{15})C(=O)OR^{15}$, —$R^{16}$—$N(R^{15})C(=O)R^{15}$, —$R^{16}$—$N(R^{15})C(=O)N(R^{15})_2$, —$R^{16}$—$N(R^{15})S(=O)_tR^1$ (where t is 1 or 2), —$R^{16}$—$S(=O)_tOR^{15}$ (where t is 1 or 2), —$R^{16}$—$S(=O)_pR^{15}$ (where p is 0, 1 or 2), and —$R^{16}$—$S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain, and where each of the above substituents may be optionally substituted as defined herein.

"Aralkyl" refers to a radical of the formula —$R_aR_b$ where $R_a$ is an alkyl radical as defined above and $R_b$ is one or more aryl radicals as defined above, for example, phenyl, diphenylmethyl and the like. The aryl radical(s) may be optionally substituted as described above.

"Aralkenyl" refers to a radical of the formula —$R_cR_b$ where $R_c$ is an alkenyl radical as defined above and $R_b$ is one or more aryl radicals as defined above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula —$R_dR_b$ where $R_d$ is an alkynyl radical as defined above and $R_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Aryloxy" refers to a radical of the formula —$OR_b$ where $R_b$ is an aryl group as defined above. The aryl part of the aryloxy radical may be optionally substituted as defined above.

"Aralkyloxy" refers to a radical of the formula —$OR_b$ where $R_b$ is an aralkyl group as defined above. The aralkyl part of the aralkyloxy radical may be optionally substituted as defined above.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclo-butyl, cyclopentyl, cyclohexyl, cycloheptyl, and cyclooctyl. Polycyclic radicals include, for example, adamantine, norbornane, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from alkyl, alkenyl, halo, haloalkyl, haloalkenyl, cyano, amino, nitro, oxo, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$, —$R^{16}$—$N(R^{15})_2$, —$R^{16}$—$C(=O)R^{15}$, —$R^{16}$—$C(=O)R^{15}$, —$R^{16}$—$C(=O)N(R^{15})_2$, —$R^{16}$—$N(R^{15})C(=O)OR^{15}$-$R^{16}$—$N(R^{15})C(=O)$ $R^{15}$-$R^{16}$—$N(R^{15})C(=O)N(R^{15})_2$, —$R^{16}$—$N(R^{15})S(=O)_t$ $R^{15}$ (where t is 1 or 2), —$R^{16}$—$S(=O)_tOR^{15}$ (where t is 1 or 2), —$R^{16}$—$S(=O)_pR^{15}$ (where p is 0, 1 or 2), and —$R^{16}$—$S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain, and where each of the above substituents may be optionally substituted as defined herein.

"Cycloalkylalkyl" refers to a radical of the formula —$R_aR_e$ where $R_a$ is an alkyl radical as defined above and $R_e$ is a cycloalkyl radical as defined above. The alkyl radical and the cycloalkyl radical may be optionally substituted as defined above.

"Cycloalkylalkenyl" refers to a radical of the formula —$R_cR_e$ where $R_c$ is an alkenyl radical as defined above and $R_e$ is a cycloalkyl radical as defined above. The alkenyl radical and the cycloalkyl radical may be optionally substituted as defined above.

"Cycloalkylalkynyl" refers to a radical of the formula —$R_dR_e$ where $R_d$ is an alkynyl radical as defined above and $R_e$ is a cycloalkyl radical as defined above. The alkynyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Haloalkynyl" refers to an alkynyl radical, as defined above, that is substituted by one or more halo radicals, as defined above. The alkynyl part of the haloalkyl radical may be optionally substituted as defined above for an alkynyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azepinyl, 2,5-diazabicyclo[2.2.1]heptan-2-yl, hexahydro-1H-1,4-diazepinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxiranyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—$OC(=O)$—$R^{15}$-$R^{16}N(R^{15})_2$, —$R^{16}$—$C(=O)R^{15}$, —$R^{16}$—$C(=O)R^{15}$, —$R^{16}$—$C(=O)N(R^{15})_2$—$R^{16}$—$N(R^{15})C(=O)OR^{15}$-$R^{16}$—$N(R^{15})C(=O)R^{15}$-

$R^{16}$—N($R^{15}$)C(=O)N($R^{15}$)$_2$, —$R^{16}$—N($R^{15}$)S(=O)$_t R^{15}$ (where t is 1 or 2), —$R^{16}$—S(=O)$_t OR^{15}$ (where t is 1 or 2), —$R^{16}$—S(=O)$_p R^{15}$ (where p is 0, 1 or 2), and —$R^{16}$—S(=O)$_t$N($R^{15}$)$_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain, and where each of the above substituents may be optionally substituted as defined herein.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula —$R_a R_f$ where $R_a$ is an alkyl radical as defined above and $R_f$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heterocyclylalkenyl" refers to a radical of the formula —$R_c R_f$ where $R_c$ is an alkenyl radical as defined above and $R_f$ is a heterocyclyl radical as defined above, and if the heterocyclyl is a nitrogen-containing heterocyclyl, the heterocyclyl may be attached to the alkenyl radical at the nitrogen atom. The alkenyl part of the heterocyclylalkenyl radical may be optionally substituted as defined above for an alkenyl group. The heterocyclyl part of the heterocyclylalkenyl radical may be optionally substituted as defined above for a heterocyclyl group.

"Heterocyclylalkynyl" refers to a radical of the formula —$R_d R_f$ where $R_d$ is an alkynyl radical as defined above and $R_f$ is a heterocyclyl radical as defined above, and if the heterocyclyl is a nitrogen-containing heterocyclyl, the heterocyclyl may be attached to the alkynyl radical at the nitrogen atom. The alkynyl part of the heterocyclylalkynyl radical may be optionally substituted as defined above for an alkynyl group. The heterocyclyl part of the heterocyclylalkynyl radical may be optionally substituted as defined above for a heterocyclyl group.

"Heteroaryl" refers to a 3- to 18-membered fully or partially aromatic ring radical which consists of one to thirteen carbon atoms and from one to six heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, acridinyl, benzimidazolyl, benzindolyl, benzodioxolyl, benzofuranyl, benzooxazolyl, benzothiazolyl, benzothiadiazolyl, benzo[b]-[1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrazolyl, pyridinyl, pyrazinyl, pyrimidinyl, pyridazinyl, pyrrolyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkoxy, halo, haloalkyl, haloalkenyl, cyano, oxo, thioxo, nitro, oxo, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—C(=O)—$R^{15}$, —$R^{16}$—N($R^{15}$)$_2$, —$R^{16}$—C(=O)$R^{15}$, —$R^{16}$—C(=O)$OR^{15}$, —$R^{16}$—C(=O)N($R^{15}$)$_2$, —$R^{16}$—N($R^{15}$)C(=O)$OR^{15}$, —$R^{16}$—N($R^{15}$)C(=O)$R^{15}$-$R^{16}$—N($R^{15}$)C(=O)N($R^{15}$)$_2$, —$R^{16}$—N($R^{15}$)S(=O)$_t R^{15}$ (where t is 1 or 2), —$R^{16}$—S(=O)$_t OR^{15}$ (where t is 1 or 2), —$R^{16}$—S(=O)$_p R^{15}$ (where p is 0, 1 or 2), and —$R^{16}$—S(=O)$_t$N($R^{15}$)$_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain, and where each of the above substituents may be optionally substituted as defined herein.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroaralkyl" refers to a radical of the formula —$R_a R_g$ where $R_a$ is an alkyl radical as defined above and $R_g$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroaralkenyl" refers to a radical of the formula —$R_c R_g$ where $R_d$ is an alkenyl radical as defined above and $R_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Heteroaralkynyl" refers to a radical of the formula —$R_d R_g$ where $R_d$ is an alkynyl radical as defined above and $R_g$ is a heteroaryl radical as defined above. The heteroaryl part of the heteroarylalkynyl radical may be optionally substituted as defined above for a heteroaryl group. The alkynyl part of the heteroarylalkynyl radical may be optionally substituted as defined above for an alkynyl group.

"Hydroxyalkyl" refers to an alkyl radical, as defined above, substituted by one or more hydroxy (—OH) groups. If the hydroxyalkyl radical is attached to a hetero atom (e.g., oxygen or nitrogen), a hydroxy group can not be attached to a carbon in the alkyl group which is directly attached to the hetero atom.

"Hydroxyiminoalkyl" refers to an alkyl radical, as defined above, substituted by a hydroxyimino (=NOH) group.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutically acceptable derivative" means any non-toxic salt, ester, salt of an ester, or other derivative or a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of c-Met kinase.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention that, when administered to a mammal, preferably a human, is sufficient to effect treatment, as defined below, of a disease or condition of interest in the mammal, preferably a human. The amount of a compound of the invention which constitutes a "therapeutically effective amount" will vary depending on, e.g., the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy, but it can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, and their structures as depicted herein, are also meant to include all isomeric (e.g., enantiomeric, diastereomeric, and geometric (or conformational)) forms, which may be defined, in terms of absolute stereochemistry, as (R)- or (S)- or, as (D)- or (L)- for amino acids. The present invention is meant to include all such possible isomers, as well as their racemic, enantio-enriched, and optically pure forms. Optically active (+) and (−), (R)- and (S)-, or (D)- and (L)-isomers may be prepared using chiral synthons or chiral reagents, or resolved using conventional techniques, such as for example but not limited to HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Additionally, unless otherwise stated, the compounds of the present invention are also meant to include compounds that differ in structure only in the presence of one or more isotopically enriched atoms. For example, compounds having the present structures except for the replacement of hydrogen by deuterium or tritium, or the replacement of a fluorine by a $^{18}$F-fluoro label ($^{18}$F isotope), or the replacement of a carbon by a $^{11}$C—, $^{13}$C—, or $^{14}$C-enriched carbon ($^{11}$C—, $^{13}$C—, or $^{14}$C-carbon label; $^{11}$C—, $^{13}$C—, or $^{14}$C-isotope) are within the scope of this invention. Such compounds are useful, for example, as analytical tools or probes in biological assays, or may be used as tracers for diagnostic in vivo imaging of diseases, or as tracers for pharmacodynamic, pharmacokinetic or receptor studies.

The structure diagrams used herein employ and rely on the Chemical Abstracts Service (CAS) rules. The chemical naming protocol used herein employ and rely on the Chemical Abstracts Service (CAS) rules (for complex chemical names employed herein, a substituent group is named before the group to which it attaches; e.g. 2-cyclopropylethyl comprises an ethyl backbone with cyclopropyl substituent), however in some cases a computer generated name (e.g. using AutoNom 2000 for ISIS/Draw) is used. In each case, the compounds are defined by the structural formula, either as given or as derivable from the Example tables.

The following compound serves to illustrate the naming systems used.

| Structure | Name based on CAS rules | AutoNom 2000 name |
|---|---|---|
| (structure shown) | 4-(3-cyano-4-fluorophenyl)-1,4-dihydro-2,6-dimethyl-3,5-pyridinedicarbonitrile | 4-(3-cyano-4-fluoro-phenyl)-2,6-dimethyl-1,4-dihydro-pyridine-3,5-dicarbonitrile |

In chemical structure diagrams, all bonds are identified, except for some carbon atoms, which are assumed to be bonded to sufficient hydrogen atoms to complete the valency. Unless otherwise indicated, compound names are intended to include any single stereoisomer, enantiomer, diastereomer, racemate or mixture of stereoisomers.

The use of parentheses in a formula herein is used to conserve space. Accordingly, the use of parentheses in a formula indicates that the group enclosed within the parentheses is attached directly to the atom preceding the parenthesis. For example, the term —P(O)(OR$^5$)—R$^7$—N(R$^5$)—C(O)—R$^7$—N(R$^5$)—C(O)OR$^8$ can be drawn as follows:

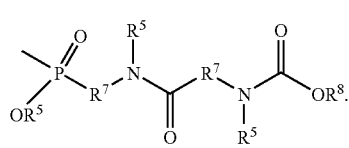

Preferred according to the present invention are compounds of formula I having the formula I-3

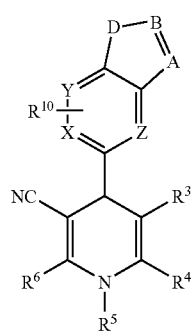

I-3 wherein,
A, B are independently of one another C—R$^{11}$ or N;
D is N—R$^{12}$, O, or S;
X, Y, and Z are independently of one another C—R$^{11}$ or N;
R$^{12}$ is hydrogen, optionally substituted alkyl, optionally substituted alkenyl, optionally substituted alkynyl, optionally substituted cycloalkyl, optionally substituted cycloalkylalkyl, —C(=O)OR$^8$, —C(=O)NR$^8$R$^9$, optionally substituted aryl, optionally substituted aralkyl, optionally substituted heteroaryl, optionally substituted heteroaralkyl, optionally substituted heterocyclyl, or optionally substituted heterocyclylalkyl.

Compounds preferred according to the present invention are those of the formula I, in which
A is C—R$^{11}$,
B is N,
D is N—R$^{12}$,
X, Y and Z are independently of one another C—R$^{11}$ or N, whereby at least two of X, Y and Z are C—R$^{11}$.

Compounds more preferred according to the present invention are those of the formula I, in which
A is C—R$^{11}$,
B is N,
D is N—R$^{12}$,
X, Y and Z are independently of one another C—R$^{11}$, in which more preferably C—R$^{11}$ is a CH-group.

Compounds more preferred according to the present invention are those of the formula I, in which
D is an NH-group.

Compounds likewise preferred are those of formula I having the formula I-1

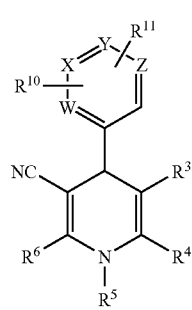

I-1 wherein,
W, X, Y, and Z are each independently C—R$^{11}$, C—R$^{14}$, or N.

Compounds likewise more preferred are those of the formula I-1 in which
W is CH or N;
X is C—$R^{14}$;
Y and Z are CH;
$R^7$ is optionally substituted alkyl, optionally substituted aryl, optionally substituted heteroaryl or optionally substituted heterocyclyl;
$R^{10}$ and $R^{11}$ are absent.

Compounds more preferred according to the present invention are those of the formula I in which
$R^3$ is a cyano group.

Compounds more preferred according to the present invention are those of the formula I in which
$R^4$ is optionally substituted alkyl, optionally substituted heterocyclylalkyl, optionally substituted aryl or optionally substituted heteroaryl; preferably $C_{1-3}$alkyl, phenyl or pyridyl; more preferably methyl.

Compounds more preferred according to the present invention are those of the formula I in which
$R^5$ is hydrogen, optionally substituted alkyl, optionally substituted heterocyclylalkyl, cycloalkyl, or benzyl; preferably hydrogen, $C_{1-4}$alkyl or benzyl; more preferably methyl or hydrogen.

Compounds more preferred according to the present invention are those of the formula I in which
$R^4$ and $R^5$ together form an alkylene bridge.

Compounds more preferred according to the present invention are those of the formula I, in which
$R^6$ is $C_{1-3}$alkyl; more preferably methyl.

Compounds very particularly preferred according to the present invention are those of formula I, namely
80  1,4-dihydro-4-(1H-indazol-5-yl)-2,6-dimethyl-3,5-pyridinedicarbonitrile;
81 1,4-dihydro-2,6-dimethyl-4-(3-methyl-1H-indazol-5-yl)-3,5-pyridinedicarbonitrile;
82 4-(3-amino-1H-indazol-5-yl)-1,4-dihydro-2,6-dimethyl-3,5-pyridinedicarbonitrile;
83  1,4-dihydro-2,6-dimethyl-4-[3-(4-morpholinylmethyl)-1H-indazol-5-yl]-3,5-pyridinedicarbonitrile;
84  1,4-dihydro-4-[3-(3-methoxyphenyl)-1H-indazol-5-yl]-2,6-dimethyl-3,5-pyridinedicarbonitrile;
85  5-(3,5-dicyano-1,4-dihydro-2,6-dimethyl-4-pyridinyl)-1H-indazole-3-carboxylic acid methyl ester;
86  5-(3,5-dicyano-1,4-dihydro-2,6-dimethyl-4-pyridinyl)-1H-indazole-3-carboxylic acid;
87 1,4-dihydro-2,6-dimethyl-4-[3-(3-pyridinyl)-1H-indazol-5-yl]-3,5-pyridinedicarbonitrile;
88 1,4-dihydro-2,6-dimethyl-4-[3-(2-pyridinyl)-1H-indazol-5-yl]-3,5-pyridinedicarbonitrile;
89  N-[5-(3,5-dicyano-1,4-dihydro-2,6-dimethyl-4-pyridinyl)-1H-indazol-3-yl]-acetamide;
91  1,4-dihydro-2,6-dimethyl-4-[3-[(3-pyridinylamino)methyl]-1H-indazol-5-yl]-3,5-pyridinedicarbonitrile;
92 3-amino-5-(3,5-dicyano-1,4-dihydro-2,6-dimethyl-4-pyridinyl)-1H-indazole-1-carboxylic acid 1,1-dimethylethyl ester;
93 1,4-dihydro-4-(3-iodo-1H-indazol-5-yl)-2,6-dimethyl-3,5-pyridinedicarbonitrile;
94.1 1,4-dihydro-2,6-dimethyl-4-[3-(4-pyridinyl)-1H-indazol-5-yl]-3,5-pyridinedicarbonitrile,
95 4-(3-amino-1-benzoyl-1H-indazol-5-yl)-1,4-dihydro-2,6-dimethyl-3,5-pyridinedicarbonitrile
99.2 5-(3,5-dicyano-1,4-dihydro-2,6-dimethyl-4-pyridinyl)-N-methyl-1H-indazole-3-carboxamide;
103.2  5-(3,5-dicyano-1,4-dihydro-2,6-dimethyl-4-pyridinyl)-N-[2-(dimethylamino)-ethyl]-1H-indazole-3-carboxamide;
105 1,4-dihydro-2,6-dimethyl-4-[3-[(phenylmethyl)amino]-1H-indazol-5-yl]-3,5-pyridinedicarbonitrile;
106.2  5-(3,5-dicyano-2,6-dimethyl-1,4-dihydro-pyridin-4-yl)-1H-indazole-3-carboxylic acid (3-dimethylamino-propyl)-amide;
110  4-[3-amino-1-(methoxy-3-pyridinylmethyl)-1H-indazol-5-yl]-1,4-dihydro-2,6-dimethyl-3,5-pyridinedicarbonitrile;
111  1,4-dihydro-2,6-dimethyl-4-[3-[4-(1-piperazinyl)phenyl]-1H-indazol-5-yl]-3,5-pyridinedicarbonitrile;
114.2  5-(3,5-dicyano-2,6-dimethyl-1,4-dihydro-pyridin-4-yl)-1H-indazole-3-carboxylic acid dimethylamide;
118 1,4-dihydro-4-[3-[(2-hydroxyethyl)amino]-1H-indazol-5-yl]-2,6-dimethyl-3,5-pyridinedicarbonitrile;
119  5-(3,5-dicyano-1,4-dihydro-2,6-dimethyl-4-pyridinyl)-3-[(2-hydroxyethyl)-amino]-1H-indazole-1-carboxylic acid, 1,1-dimethylethyl ester;
120  1,4-dihydro-2,6-dimethyl-4-[3-[(3-pyridinylmethyl)amino]-1H-indazol-5-yl]-3,5-pyridinedicarbonitrile;
121  4-[3-(ethylamino)-1H-indazol-5-yl]-1,4-dihydro-2,6-dimethyl-3,5-pyridinedicarbonitrile;
123  [4-[5-(3,5-dicyano-1,4-dihydro-2,6-dimethyl-4-pyridinyl)-1H-indazol-3-yl]-phenyl]-carbamic acid methyl ester;
124  5-(3,5-dicyano-1,4-dihydro-2,6-dimethyl-4-pyridinyl)-N-[2-(1-pyrrolidinyl)ethyl]-1H-indazole-3-carboxamide;
125  5-(3,5-dicyano-1,4-dihydro-2,6-dimethyl-4-pyridinyl)-N-[2-(1-methyl-2-pyrrolidinyl)ethyl]-1H-indazole-3-carboxamide;
127 1,4-dihydro-2,6-dimethyl-4-[3-[[(4-nitrophenyl)methyl]amino]-1H-indazol-5-yl]-3,5-pyridinedicarbonitrile;
128  4-[3-[[(4-aminophenyl)methyl]amino]-1H-indazol-5-yl]-1,4-dihydro-2,6-dimethyl-3,5-pyridinedicarbonitrile;
129  N-[5-(3,5-dicyano-1,4-dihydro-2,6-dimethyl-4-pyridinyl)-1H-indazol-3-yl]-benzamide;
130  1,4-dihydro-2,6-dimethyl-4-[3-[[4-(4-pyridinyl)-1-piperazinyl]methyl]-1H-indazol-5-yl]-3,5-pyridinedicarbonitrile;
131 4-[[[5-(3,5-dicyano-1,4-dihydro-2,6-dimethyl-4-pyridinyl)-1H-indazol-3-yl]-amino]methyl]-1-piperidinecarboxylic acid 1,1-dimethylethyl ester;
133  1,4-dihydro-2,6-dimethyl-4-[3-[(4-piperidinylmethyl)amino]-1H-indazol-5-yl]-3,5-pyridinedicarbonitrile;
135 4-[[[5-(3,5-dicyano-1,4-dihydro-2,6-dimethyl-4-pyridinyl)-1H-indazol-3-yl]-amino]methyl]-benzoic acid methyl ester;
136 4-[[[5-(3,5-dicyano-1,4-dihydro-2,6-dimethyl-4-pyridinyl)-1H-indazol-3-yl]-amino]methyl]-benzoic acid;
137 1,4-dihydro-2,6-dimethyl-4-[3-[6-(4-methyl-1-piperazinyl)-3-pyridinyl]-1H-indazol-5-yl]-3,5-pyridinedicarbonitrile;
138  4-[3-[4-[(dimethylamino)methyl]phenyl]-1H-indazol-5-yl]-1,4-dihydro-2,6-dimethyl-3,5-pyridinedicarbonitrile;
139  4-[3-[3-(dimethylamino)-1-propynyl]-1H-indazol-5-yl]-1,4-dihydro-2,6-dimethyl-3,5-pyridinedicarbonitrile;
140 1,4-dihydro-2,6-dimethyl-4-[3-[4-(4-methyl-1-piperazinyl)phenyl]-1H-indazol-5-yl]-3,5-pyridinedicarbonitrile;
141  N-[5-(3,5-dicyano-1,4-dihydro-2,6-dimethyl-4-pyridinyl)-1H-indazol-3-yl]-2-(diethylamino)-acetamide;
142  4-[3-(1H-benzimidazol-2-yl)-1H-indazol-5-yl]-1,4-dihydro-2,6-dimethyl-3,5-pyridinedicarbonitrile;
143  5-(3,5-dicyano-1,4-dihydro-2,6-dimethyl-4-pyridinyl)-N-methoxy-N-methyl-1H-indazole-3-carboxamide;

144 1,4-dihydro-4-[3-(hydroxymethyl)-1H-indazol-5-yl]-2,6-dimethyl-3,5-pyridinedicarbonitrile;
145 4-(3-formyl-1H-indazol-5-yl)-1,4-dihydro-2,6-dimethyl-3,5-pyridinedicarbonitrile;
147 N-[5-(3,5-dicyano-1,4-dihydro-2,6-dimethyl-4-pyridinyl)-1H-indazol-3-yl]-N'-methyl-urea;
148 4-(3-chloro-1H-indazol-5-yl)-1,4-dihydro-2,6-dimethyl-3,5-pyridinedicarbonitrile;
149 1,4-dihydro-4-[3-[(E)-(hydroxyimino)methyl]-1H-indazol-5-yl]-2,6-dimethyl-3,5-pyridinedicarbonitrile;
150 1,4-dihydro-4-[3-[(1H-imidazol-4-ylmethyl)amino]-1H-indazol-5-yl]-2,6-dimethyl-3,5-pyridinedicarbonitrile;
151 4-(3-bromo-1H-indazol-5-yl)-1,4-dihydro-2,6-dimethyl-3,5-pyridinedicarbonitrile;
152 1,4-dihydro-4-[3-[4-[4-(2-hydroxyethyl)-1-piperazinyl]phenyl]-1H-indazol-5-yl]-2,6-dimethyl-3,5-pyridinedicarbonitrile;
153 4-[3-amino-1-[(4-aminophenyl)methyl]-1H-indazol-5-yl]-1,4-dihydro-2,6-dimethyl-3,5-pyridinedicarbonitrile;
155 4-[4-[5-(3,5-dicyano-1,4-dihydro-2,6-dimethyl-4-pyridinyl)-1H-indazol-3-yl]-phenyl]-1-piperazinecarboxylic acid 1,1-dimethylethyl ester;
156 1,4-dihydro-2,6-dimethyl-4-[3-(4-morpholinyl)-1H-indazol-5-yl]-3,5-pyridinedicarbonitrile;
157 1,4-dihydro-2,6-dimethyl-4-[3-[1-(4-piperidinyl)-1H-pyrazol-4-yl]-1H-indazol-5-yl]-3,5-pyridinedicarbonitrile;
158 4-(3-acetyl-1H-indazol-5-yl)-1,4-dihydro-2,6-dimethyl-3,5-pyridinedicarbonitrile;
159 1,4-dihydro-4-[3-[(E)-(methoxyimino)methyl]-1H-indazol-5-yl]-2,6-dimethyl-3,5-pyridinedicarbonitrile;
160 1,4-dihydro-4-[3-[(1E)-1-(hydroxyimino)ethyl]-1H-indazol-5-yl]-2,6-dimethyl-3,5-pyridinedicarbonitrile;
163 1,4-dihydro-2,6-dimethyl-4-[3-[[[4-(4-morpholinyl)phenyl]methyl]amino]-1H-indazol-5-yl]-3,5-pyridinedicarbonitrile;
164 1,4-dihydro-2,6-dimethyl-4-[3-(1-piperazinyl)-1H-indazol-5-yl]-3,5-pyridinedicarbonitrile;
165.2 2,6-dimethyl-4-[3-(4-propyl-piperazin-1-yl)-1H-indazol-5-yl]-1,4-dihydropyridine-3,5-dicarbonitrile;
166 1,4-dihydro-4-[3-[[4-(2-hydroxyethyl)-1-piperazinyl]methyl]-1H-indazol-5-yl]-2,6-dimethyl-3,5-pyridinedicarbonitrile;
167.2 4-[5-(3,5-Dicyano-2,6-dimethyl-1,4-dihydro-pyridin-4-yl)-1H-indazol-3-ylmethyl]-piperazine-1-carboxylic acid ethyl ester;
168 1,4-dihydro-4-[3-[[[4-[(3-hydroxy-1-pyrrolidinyl)carbonyl]phenyl]methyl]amino]-1H-indazol-5-yl]-2,6-dimethyl-3,5-pyridinedicarbonitrile;
169 1,4-dihydro-2,6-dimethyl-4-[3-(trifluoromethyl)-1H-indazol-5-yl]-3,5-pyridinedicarbonitrile;
170 1,4-dihydro-4-[3-(1H-imidazol-2-yl)-1H-indazol-5-yl]-2,6-dimethyl-3,5-pyridinedicarbonitrile;
172 1,4-dihydro-4-[3-[[[4-[(2-hydroxyethyl)methylamino]phenyl]methyl]amino]-H-indazol-5-yl]-2,6-dimethyl-3,5-pyridinedicarbonitrile;
173 1,4-dihydro-2,6-dimethyl-4-[3-(1H-pyrazol-4-yl)-1H-indazol-5-yl]-3,5-pyridinedicarbonitrile;
174 1,4-dihydro-2,6-dimethyl-4-[3-(1-methyl-1H-pyrazol-4-yl)-1H-indazol-5-yl]-3,5-pyridinedicarbonitrile;
175 1,4-dihydro-4-[3-(3-isoxazolyl)-1H-indazol-5-yl]-2,6-dimethyl-3,5-pyridinedicarbonitrile;
176 1,4-dihydro-4-(3-hydroxy-1H-indazol-5-yl)-2,6-dimethyl-3,5-pyridinedicarbonitrile;
177 1,4-dihydro-2,6-dimethyl-4-[3-(5-oxazolyl)-1H-indazol-5-yl]-3,5-pyridinedicarbonitrile;
178 1,4-dihydro-2,6-dimethyl-4-[3-(2-thienyl)-1H-indazol-5-yl]-3,5-pyridinedicarbonitrile;
204 1,4-dihydro-2,6-dimethyl-4-(1H-pyrazolo[3,4-b]pyridin-5-yl)-3,5-pyridinedicarbonitrile;
249 1,4-dihydro-4-(1H-indazol-5-yl)-2-methyl-6-phenyl-3,5-pyridinedicarbonitrile;
250 1,4-dihydro-4-(1H-indazol-5-yl)-2-methyl-6-(3-nitrophenyl)-3,5-pyridinedicarbonitrile;
251 3-[3,5-dicyano-1,4-dihydro-4-(1H-indazol-5-yl)-6-methyl-2-pyridinyl]-1-piperidinecarboxylic acid phenylmethyl ester;
252 2-(3-aminophenyl)-1,4-dihydro-4-(1H-indazol-5-yl)-6-methyl-3,5-pyridinedicarbonitrile;
253 N-[3-[3,5-dicyano-1,4-dihydro-4-(1H-indazol-5-yl)-6-methyl-2-pyridinyl]-phenyl]-acetamide;
255 2-(2-aminoethyl)-1,4-dihydro-4-(1H-indazol-5-yl)-6-methyl-3,5-pyridinedicarbonitrile;
261 4-[3,5-dicyano-1,4-dihydro-4-(1H-indazol-5-yl)-6-methyl-2-pyridinyl]-N-[2-(4-morpholinyl)ethyl]-benzamide;
264 4-(3-amino-1H-indazol-5-yl)-2-(4-chlorophenyl)-1,4-dihydro-6-methyl-3,5-pyridinedicarbonitrile;
265 1,4-dihydro-4-(1H-indazol-5-yl)-6-methyl-[2,4'-bipyridine]-3,5-dicarbonitrile;
266 1,4-dihydro-4-(1H-indazol-5-yl)-6-methyl-[2,3'-bipyridine]-3,5-dicarbonitrile;
267 2-(2-furanyl)-1,4-dihydro-4-(1H-indazol-5-yl)-6-methyl-3,5-pyridinedicarbonitrile;
268 3,5-dicyano-1,4-dihydro-4-(1H-indazol-5-yl)-6-methyl-2-pyridinecarboxylic acid ethyl ester;
269 2,6-diethyl-1,4-dihydro-4-(1H-indazol-5-yl)-3,5-pyridinedicarbonitrile;
270 1,4-dihydro-2-(4-chloropyrid-3-yl)-6-methyl-4-(1H-indazol-5-yl)-3,5-pyridinedicarbonitrile;
271 1,4-dihydro-4-(1H-indazol-5-yl)-6-methyl-6'-(4-morpholinyl)-[2,3'-bipyridine]-3,5-dicarbonitrile;
272 2-[3-fluoro-4-(4-morpholinyl)phenyl]-1,4-dihydro-4-(1H-indazol-5-yl)-6-methyl-3,5-pyridinedicarbonitrile;
273 1,4-dihydro-6'-[(2-hydroxyethyl)methylamino]-4-(1H-indazol-5-yl)-6-methyl-[2,3'-bipyridine]-3,5-dicarbonitrile;
274 1,4-dihydro-4-(1H-indazol-5-yl)-6-methyl-6'-[[2-(4-morpholinyl)ethyl]amino]-[2,3'-bipyridine]-3,5-dicarbonitrile;
275 6'-[[2-(dimethylamino)ethyl]amino]-1,4-dihydro-4-(1H-indazol-5-yl)-6-methyl-[2,3'-bipyridine]-3,5-dicarbonitrile;
276 2'-chloro-1,4-dihydro-4-(1H-indazol-5-yl)-6-methyl-[2,4'-bipyridine]-3,5-dicarbonitrile;
278 1,4-dihydro-4-(1H-indazol-5-yl)-6-methyl-2'-[[2-(4-morpholinyl)ethyl]amino]-[2,4'-bipyridine]-3,5-dicarbonitrile;
280 1,4-dihydro-2'-[(2-hydroxyethyl)methylamino]-4-(1H-indazol-5-yl)-6-methyl-[2,4'-bipyridine]-3,5-dicarbonitrile;
281 4-(3-amino-1H-indazol-5-yl)-2-(2,5-dimethyl-3-furanyl)-1,4-dihydro-6-methyl-3,5-pyridinedicarbonitrile;
282 4-(3-amino-1H-indazol-5-yl)-1,4-dihydro-2-methyl-6-(2-methyl-3-furanyl)-3,5-pyridinedicarbonitrile;
288 4-(3-amino-1H-indazol-5-yl)-1,4-dihydro-1,2,6-trimethyl-3,5-pyridinedicarbonitrile;
289 1,4-dihydro-4-(1H-indazol-5-yl)-1,2,6-trimethyl-3,5-pyridinedicarbonitrile;
290 3,5-dicyano-4-(1H-indazol-5-yl)-2,6-dimethyl-1(4H)-pyridineacetic acid ethyl ester;
292 1,4-dihydro-1-(2-hydroxyethyl)-4-(1H-indazol-5-yl)-2,6-dimethyl-3,5-pyridinedicarbonitrile;

293 4-(3-amino-1H-indazol-5-yl)-1,4-dihydro-2,6-dimethyl-1-(phenylmethyl)-3,5-pyridinedicarbonitrile;
294 1-ethyl-4-(3-amino-1H-indazol-5-yl)-1,4-dihydro-2,6-dimethyl-3,5-pyridinedicarbonitrile;
297 4-(3-chloro-1H-indazol-5-yl)-1,4-dihydro-1-(2-hydroxyethyl)-2,6-dimethyl-3,5-pyridinedicarbonitrile;
298 4-(3-chloro-1H-indazol-5-yl)-1,4-dihydro-1,2,6-trimethyl-3,5-pyridinedicarbonitrile;
299 4-(3-amino-1H-indazol-5-yl)-1,4-dihydro-1-(2-hydroxyethyl)-2,6-dimethyl-3,5-pyridinedicarbonitrile;
301 1-cyclopropyl-1,4-dihydro-2,6-dimethyl-4-(3-methyl-1H-indazol-5-yl)-3,5-pyridinedicarbonitrile;
302 1,4-dihydro-4-(1H-indazol-5-yl)-2,6-dimethyl-1-(2-propynyl)-3,5-pyridinedicarbonitrile;
304 6,7,8,9-tetrahydro-2-(1H-indazol-5-yl)-4-methyl-2H-quinolizine-1,3-dicarbonitrile.

Compounds also very particularly preferred according to the present invention are those of formula I, namely 94.2 1,4-dihydro-2,6-dimethyl-4-[3-(4-pyridinyl)-1H-indazol-5-yl]-3,5-pyridinedicarbonitrile, acetic acid salt;
99.1 5-(3,5-dicyano-1,4-dihydro-2,6-dimethyl-4-pyridinyl)-N-methyl-1H-indazole-3-carboxamide, TFA salt;
103.1 5-(3,5-dicyano-1,4-dihydro-2,6-dimethyl-4-pyridinyl)-N-[2-(dimethylamino)-ethyl]-1H-indazole-3-carboxamide, TFA salt;
106.1 5-(3,5-dicyano-2,6-dimethyl-1,4-dihydro-pyridin-4-yl)-1H-indazole-3-carboxylic acid (3-dimethylamino-propyl)-amide, TFA salt;
114.1 5-(3,5-dicyano-2,6-dimethyl-1,4-dihydro-pyridin-4-yl)-1H-indazole-3-carboxylic acid dimethylamide, TFA salt;
161 4-[3-(ethylamino)-1H-indazol-5-yl]-1,4-dihydro-2,6-dimethyl-3,5-pyridinedicarbonitrile, monohydrochloride;
165.1 2,6-dimethyl-4-[3-(4-propyl-piperazin-1-yl)-1H-indazol-5-yl]-1,4-dihydropyridine-3,5-dicarbonitrile, TFA salt;
167.1 4-[5-(3,5-Dicyano-2,6-dimethyl-1,4-dihydro-pyridin-4-yl)-1H-indazol-3-ylmethyl]-piperazine-1-carboxylic acid ethyl ester, TFA salt;
257 4-[3,5-dicyano-1,4-dihydro-4-(1H-indazol-5-yl)-6-methyl-2-pyridinyl]-benzoic acid methyl ester;
258 1,4-dihydro-2-[4-(hydroxymethyl)phenyl]-4-(1H-indazol-5-yl)-6-methyl-3,5-pyridinedicarbonitrile;
259 4-(3-amino-1H-indazol-5-yl)-1,4-dihydro-2-methyl-6-phenyl-3,5-pyridinedicarbonitrile;
260 4-[3,5-dicyano-1,4-dihydro-4-(1H-indazol-5-yl)-6-methyl-2-pyridinyl]-benzoic acid;
306 1,4-dihydro-1,2,6-trimethyl-4-(3-methyl-1H-indazol-5-yl)-3,5-pyridinedicarbonitrile;
307 1,4-dihydro-2,6-dimethyl-4-[3-[[2-(4-morpholinyl)ethyl]amino]-1H-indazol-5-yl]-3,5-pyridinedicarbonitrile;
308 4-[3-[(2-aminoethyl)amino]-1H-indazol-5-yl]-1,4-dihydro-2,6-dimethyl-3,5-pyridinedicarbonitrile;
309 1,4-dihydro-2,6-dimethyl-4-[3-[[2-(1-pyrrolidinyl)ethyl]amino]-1H-indazol-5-yl]-3,5-pyridinedicarbonitrile.
310 1-(2-methoxy-ethyl)-2,6-dimethyl-4-(3-methyl-1H-indazol-5-yl)-1,4-dihydropyridine-3,5-dicarbonitrile
311 4-(4-fluoro-1H-indazol-5-yl)-2,6-dimethyl-1,4-dihydro-pyridine-3,5-dicarbonitrile Compounds also very particularly preferred according to the present invention are those of formula I-1, namely 10 3-(3,5-dicyano-1,4-dihydro-2,6-dimethyl-4-pyridinyl)-benzoic acid, methyl ester;
12 3-(3,5-dicyano-2,6-dimethyl-1,4-dihydro-pyridin-4-yl)-N-methyl-benzamide, TFA salt;
17 3-(3,5-dicyano-1,4-dihydro-2,6-dimethyl-4-pyridinyl)-benzamide;
21 3-(3,5-dicyano-1,4-dihydro-2,6-dimethyl-4-pyridinyl)-N-3-pyridinyl-benzamide;
22 3-(3,5-dicyano-1,4-dihydro-2,6-dimethyl-4-pyridinyl)-N-methyl-benzamide;
23 3-(3,5-dicyano-1,4-dihydro-2,6-dimethyl-4-pyridinyl)-N-[2-(4-pyridinyl)ethyl]-benzamide;
26 3-(3,5-dicyano-1,4-dihydro-2,6-dimethyl-4-pyridinyl)-N-[2-(4-piperidinyl)ethyl]-benzamide;
27 N-[3-(3,5-dicyano-1,4-dihydro-2,6-dimethyl-4-pyridinyl)phenyl]-acetamide;
32 3-(3,5-dicyano-1,4-dihydro-2,6-dimethyl-4-pyridinyl)-N-[3-(1H-imidazol-1-yl)propyl]-benzamide;
34 [3-(3,5-dicyano-1,4-dihydro-2,6-dimethyl-4-pyridinyl)phenyl]-carbamic acid, methyl ester;
38 N-[3-(3,5-dicyano-1,4-dihydro-2,6-dimethyl-4-pyridinyl)phenyl]-3-pyridinecarboxamide;
43 3-(3,5-dicyano-1,4-dihydro-2,6-dimethyl-4-pyridinyl)-N-2-pyridinyl-benzamide;
45 3-(3,5-dicyano-1,4-dihydro-2,6-dimethyl-4-pyridinyl)-N-(3-ethoxypropyl)-benzamide;
47 2-bromo-N-[3-(3,5-dicyano-1,4-dihydro-2,6-dimethyl-4-pyridinyl)phenyl]-acetamide;
51 3-(3,5-dicyano-1,4-dihydro-2,6-dimethyl-4-pyridinyl)-N-(5-methyl-2-pyridinyl)-benzamide;
57 N-[3-(3,5-dicyano-1,4-dihydro-2,6-dimethyl-4-pyridinyl)phenyl]-4-pyridinecarboxamide;
58 N-[3-(3,5-dicyano-1,4-dihydro-2,6-dimethyl-4-pyridinyl)phenyl]-2-pyridinecarboxamide;
60 3-(3,5-dicyano-1,4-dihydro-2,6-dimethyl-4-pyridinyl)-N-[5-(trifluoromethyl)-2-pyridinyl]-benzamide;
61 3-(3,5-dicyano-1,4-dihydro-2,6-dimethyl-4-pyridinyl)-N-2-thiazolyl-benzamide;
62 3-(3,5-dicyano-1,4-dihydro-2,6-dimethyl-4-pyridinyl)-N-(6-methyl-2-pyridinyl)-benzamide;
63 3-(3,5-dicyano-1,4-dihydro-2,6-dimethyl-4-pyridinyl)-N-[5-(dimethylamino)-2-pyridinyl]-benzamide
65 N-[3-(3,5-dicyano-1,4-dihydro-2,6-dimethyl-4-pyridinyl)phenyl]-1H-imidazole-2-carboxamide;
66 N-[3-(3,5-dicyano-1,4-dihydro-2,6-dimethyl-4-pyridinyl)phenyl]-1H-imidazole-5-carboxamide;
68 N-(6-amino-2-pyridinyl)-3-(3,5-dicyano-1,4-dihydro-2,6-dimethyl-4-pyridinyl)-benzamide;
72 3-(3,5-dicyano-1,4-dihydro-2,6-dimethyl-4-pyridinyl)-N-[5-(hydroxymethyl)-2-pyridinyl]-benzamide;
76 3-(3,5-dicyano-1,4-dihydro-2,6-dimethyl-4-pyridinyl)-N-[5-[(dimethylamino)methyl]-2-pyridinyl]-benzamide;
189 3',5'-dicyano-1',4'-dihydro-N,2',6'-trimethyl-[2,4'-bipyridine]-6-carboxamide;
190 3',5'-dicyano-1',4'-dihydro-2',6'-dimethyl-N-3-pyridinyl-[2,4'-bipyridine]-6-carboxamide;
191 3',5'-dicyano-1',4'-dihydro-N-[3-(1H-imidazol-1-yl)propyl]-2',6'-dimethyl-[2,4'-bipyridine]-6-carboxamide;
192 3',5'-dicyano-1',4'-dihydro-2',6'-dimethyl-N-2-pyridinyl-[2,4'-bipyridine]-6-carboxamide;
219 3-(3,5-dicyano-1,4-dihydro-2-methyl-6-phenyl-4-pyridinyl)-benzoic acid, methyl ester;
229 3-[2-(1-acetyl-3-piperidinyl)-3,5-dicyano-1,4-dihydro-6-methyl-4-pyridinyl]-benzoic acid, methyl ester;
230 3-[2-[1-(aminocarbonyl)-3-piperidinyl]-3,5-dicyano-1,4-dihydro-6-methyl-4-pyridinyl]-benzoic acid, methyl ester;
232 3-[3,5-dicyano-1,4-dihydro-2-methyl-6-(3-nitrophenyl)-4-pyridinyl]-benzoic acid, methyl ester;
233 3-[3,5-dicyano-1,4-dihydro-2-methyl-6-(4-nitrophenyl)-4-pyridinyl]-benzoic acid, methyl ester;

234 3-[3,5-dicyano-1,4-dihydro-2-(4-hydroxyphenyl)-6-methyl-4-pyridinyl]-benzoic acid, methyl ester;
235 3-[2-(3-aminophenyl)-3,5-dicyano-1,4-dihydro-6-methyl-4-pyridinyl]-benzoic acid, methyl ester;
236 3-[2-(4-aminophenyl)-3,5-dicyano-1,4-dihydro-6-methyl-4-pyridinyl]-benzoic acid, methyl ester;
238 3-[2-(4-aminophenyl)-3,5-dicyano-1,4-dihydro-6-methyl-4-pyridinyl]-N-methyl-benzamide;
239 3-[3,5-dicyano-1,4-dihydro-2-(4-hydroxyphenyl)-6-methyl-4-pyridinyl]-N-methyl-benzamide;
240 3-(3,5-dicyano-1,4-dihydro-2-methyl-6-phenyl-4-pyridinyl)-N-methyl-benzamide;
246 3-[2-(3-aminophenyl)-3,5-dicyano-1,4-dihydro-6-methyl-4-pyridinyl]-N-[3-(1H-imidazol-1-yl)propyl]-benzamide;
284 3-(3,5-dicyano-1,4-dihydro-1,2,6-trimethyl-4-pyridinyl)-benzoic acid, methyl ester.

The invention also relates to a process for preparing compounds of the formula I-3

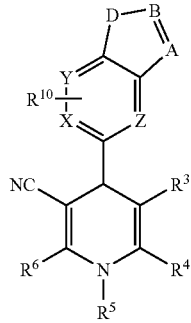

whereby
D, B, X, Y, Z, $R^3$, $R^4$, $R^5$, $R^6$ and $R^{10}$ are as defined for formula I,
comprising the following steps:
(a) conversion of compounds of the formula III

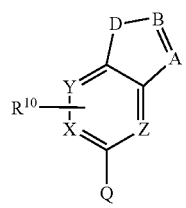

in which
Q is hydrogen, halo, —$CH_2OH$, cyano, or —$CO_2R^{13}$;
$R^{13}$ is hydrogen, $C_{1-4}$-alkyl, or benzyl;
to the intermediate aldehydes of the formula IIa,

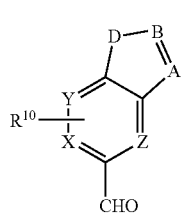

(b) conversion of the aldehydes IIa obtained in step (a) to compounds of formula I-3.

The conversion of III to IIa and IIa to I may involve one or more synthetic steps, including but not limited to protecting group manipulations.

Preferred according to the present invention is a process, in which the intermediate aldehydes of the formula IIa are selected from the group consisting of
3-(4-pyridinyl)-1H-indazole-5-carboxaldehyde;
3-(4-morpholinylmethyl)-1H-indazole-5-carboxaldehyde;
5-formyl-N-methoxy-N-methyl-1H-indazole-3-carboxamide;
3-(1H-benzimidazol-2-yl)-1H-indazole-5-carboxaldehyde;
1H-pyrazolo[4,3-b]pyridine-5-carboxaldehyde;
3-methyl-1H-indazole-5-carbaldehyde;
5-formyl-1H-indazole-3-carboxylic acid methyl ester;
4-fluoro-1H-indazole-5-carbaldehyde.

The present invention also relates to the intermediate aldehyde of the formula IIa mentioned explicitly above.

The invention also relates to a process for preparing compounds of the formula I-3 in which $R^5$ is not hydrogen, comprising the conversion of compounds of the formula IV

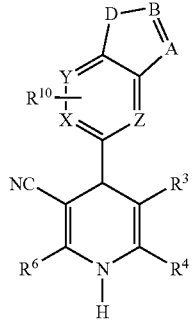

in which
A, D, B, X, Y, Z, $R^3$, $R^4$, $R^6$ and $R^{10}$ have the same meaning as defined in formula I;
to compounds of the formula I-3.

The conversion of IV to I may involve one or more synthetic steps, including but not limited to protecting group manipulations.

The following Reaction Schemes illustrate methods to make compounds of this invention, i.e., compounds of formula I:

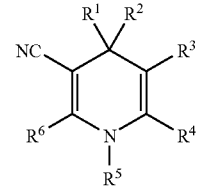

wherein $R^1$, $R^2$, $R^3$, $R^4$, $R^5$ and $R^6$ are defined above for formula I, as single stereoisomers or as mixtures of stereoisomers, or a pharmaceutically acceptable derivative thereof. It is understood that in the following description, combinations of substituents and/or variables of the depicted formulae are permissible only if such contributions result in stable compounds; that is, compounds that are sufficiently robust to survive isolation to a useful degree of purity from a reaction mixture and formulation into an efficacious therapeutic agent.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like, acetoyl, benzoyl, and the like. Suitable protecting groups for mercapto include —C(=O)—R" (where R" is alkyl, aryl or arylalkyl), p-methoxybenzyl, trityl and the like. Suitable protecting groups for carboxylic acid include alkyl, aryl or arylalkyl esters. Suitable protecting groups for the ring NH functionality in heteroaryl moieties, such as, for example, indole, or indazole, include t-butoxycarbonyl, benzyloxycarbonyl, and the like, acetoyl, benzoyl, and the like, 2-trimethylsilanylethoxymethyl (SEM), and the like.

Protecting groups may be added or removed in accordance with standard techniques, which are known to one skilled in the art and as described herein.

The use of protecting groups is described in detail in Greene, T. W. and P. G. M. Wuts, Protective Groups in Organic Synthesis (1999), 3rd Ed., Wiley. As one of skill in the art would appreciate, the protecting group may also be a polymer resin such as a Wang resin, Rink resin or a 2-chlorotritylchloride resin.

It will also be appreciated by those skilled in the art that, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula I not specifically illustrated below by using the appropriate starting components and modifying the parameters of the synthesis as needed, which can be accomplished without undue experimentation. In general, compounds employed as initial starting materials in the synthesis of the compounds of the invention are well known and commercially available, e.g., from Sigma Aldrich, Lancaster Synthesis, Inc., Maybridge, Matrix Scientific, TCI, and Fluorochem USA, etc. To the extent that the compounds employed as initial starting materials are not commercially available, the compounds may be readily synthesized using specific references provided, or by standard procedures commonly employed by those of ordinary skill in the art and/or found in general references text (see, for example, Comprehensive Organic Transformations, VCH Publishers Inc., 1989; Compendium of Organic Synthetic Methods, Volumes 1-10, 1974-2002, Wiley Interscience; Advanced Organic Chemistry Reactions, Mechanisms, and Structure, 5th edition, Wiley Interscience, 2001; Advanced Organic Chemistry, 4th Edition, *Part B, Reactions and Synthesis*, Kluwer Academic/Plenum Publishers, 2000, etc., and references cited therein).

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference.

In the following Reaction Schemes and description thereof, the following common abbreviations are used:
DMF for N,N-dimethylformamide
THF for tetrahydrofuran
TFA for trifluoroacetic acid
EtOAc for ethyl acetate
TMS for trimethylsilyl
TLC for thin layer chromatography
MeOH for methanol
NaOH for sodium hydroxide
Boc for t-butoxycarbonyl
DCM for dichloromethane
DIBAL-H for diisobutylaluminium hydride Additionally, when the following abbreviations are used throughout this disclosure, they have the following meanings:
acac acetylacetonate
$Ac_2O$ acetic anhydride
AcO (or OAc) acetate
anhyd anhydrous
aq aqueous
Ar aryl
atm atmosphere
9-BBN 9-borabicyclo[3.3.1]nonyl
BINAP 2,2'-bis(diphenylphosphino)-1,1'-binaphthyl
Bn benzyl
bp boiling point
br s broad singlet
Bz benzoyl
n-BuOH n-butanol
t-BuOH tert-butanol
t-BuOK potassium tert-butoxide
C Celsius
calcd calculated
CAN ceric ammonium nitrate
Cbz carbobenzyloxy
CDI carbonyl diimidazole
$CD_3OD$ methanol-$d_4$
Celite® diatomaceous earth filter agent, Celite® Corp.
CI-MS chemical ionization mass spectroscopy
$^{13}C$ NMR carbon-13 nuclear magnetic resonance
m-CPBA meta-chloroperoxybenzoic acid
d doublet
dd doublet of doublets
DABCO 1,4-diazabicyclo[2.2.2]octane
DBU 1,8-diazabicyclo[5.4.0]undec-7-ene
DCC N,N'-dicyclohexylcarbodiimide
DEAD diethyl azodicarboxylate
dec decomposition
DIA diisopropylamine
DMAP 4-(N,N-dimethylamino)pyridine
DME 1,2-dimethoxyethane
DMSO dimethylsulfoxide
E entgegen (configuration)
EDCI 1-(3-dimethylaminopropyl)-3-ethylcarbodiimide hydrochloride
ee enantiomeric excess
EI electron impact
ELSD evaporative light scattering detector
equiv equivalent
ES-MS electrospray mass spectroscopy
EtOH ethanol (100%)
EtSH ethanethiol
$Et_2O$ diethyl ether Et₃N triethylamine
Fmoc 9-fluorenylmethoxycarbonyl
GC gas chromatography
GC-MS gas chromatography-mass spectroscopy
h hour, hours
hex hexanes, or hexane
¹H NMR proton nuclear magnetic resonance
HMPA hexamethylphosphoramide
HMPT hexamethylphosphoric triamide
HOBT hydroxybenzotriazole
HPLC high performance liquid chromatography
insol insoluble
IPA isopropylamine
iPrOH isopropylalcohol
IR infrared
L liter
LAH lithium aluminum hydride
LC liquid chromatography
LC-MS liquid chromatography-mass spectrometry
LDA lithium diisopropylamide
M mol L⁻¹ (molar)
m multiplet
m meta
MeCN acetonitrile
MHz megahertz
min minute, minutes
μL microliter
mL milliliter
μM micromolar
mol mole
mp melting point
MS mass spectrum, mass spectrometry
Ms methanesulfonyl
m/z mass-to-charge ratio
N equiv L⁻¹ (normal)
NBS N-bromosuccinimide
nM nanomolar
NMM 4-methylmorpholine
NMR Nuclear Magnetic Resonance
o ortho
obsd observed
p para
p page
pp pages
PdCl₂ dppf [1,1'-bis(diphenylphosphino)ferrocene] dichloropalladium(II)
Pd(OAc)₂ palladium acetate
pH negative logarithm of hydrogen ion concentration
Ph phenyl
pK negative logarithm of equilibrium constant
pK_a negative logarithm of equilibrium constant for association
PPA poly(phosphoric acid)
PS-DIEA Polystyrene-bound diisopropylethylamine
PyBOP benzotriazole-1-yl-oxy-tris-pyrrolidino-phosphonium hexafluorophosphate
q quartet
rac racemic
R rectus (configurational)
R_f retardation factor (TLC)
RT retention time (HPLC)
rt room temperature
s singlet
S sinister (configurational)
t triplet
TBDMS, TBP tert-butyldimethylsilyl
TBDPS, TPS tert-butyldiphenylsilyl TEA triethylamine
Tf trifluoromethanesulfonyl (triflyl)
TFFH Fluoro-N,N,N',N'-tetramethylformamidinium hexafluorophosphate
TMAD N,N,N',N'-tetramethylethylenediamine
TMSCl trimethylsilyl chloride
Ts p-toluenesulfonyl
v/v volume to volume ratio
w/v weight to volume ratio
w/w weight to weight ratio
Z zusammen (configuration)

A. Preparation of Compounds of Formula Ia

Compounds of formula Ia are compounds of formula I wherein $R^1$ and $R^5$ are hydrogen, $R^3$ is cyano, $R^4$ and $R^6$ are $C_{1-3}$ alkyl (designated in Reaction Scheme 1 as R'), and $R^2$ is defined as in the Summary. Compounds of formula Ia can be prepared as described below in Reaction Scheme 1:

REACTION SCHEME 1

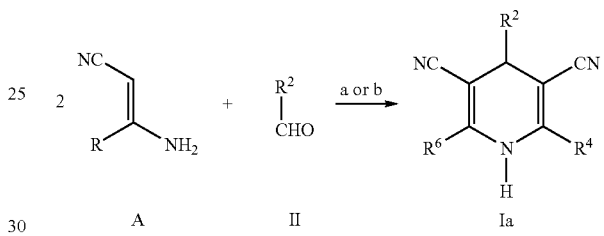

In general, compounds of formula Ia, as set forth above in Reaction Scheme 1, are prepared via Hantzsch reaction [see, Hantzsch, A. *Justus Liebigs Ann. Chem.* 215, 1 (1882); Wehinnger, E., et al. *Angew. Chem. Int Ed. Eng.*, 20, 762-769 (1981)] by reacting 2 equiv. of a suitable amino nitrile A with an aldehyde of formula II either a) in acetic acid at 110° C. for, e.g., 1 hr; or b) in refluxing methanol for 6 hr, followed by treatment with acetic acid at 50° C. for 1 hr. The particular reaction condition is based on the properties of the reactants, which can be determined by one skilled in the art without undue experimentation.

B. Preparation of Compounds of Formula Ib

Compounds of formula Ib are compounds of formula I wherein $R^1$ and $R^5$ are hydrogen, and $R^2$, $R^3$, $R^4$ and $R^6$ are defined as above. Compounds of formula Ib can be prepared as described below in Reaction Scheme 2:

REACTION SCHEME 2

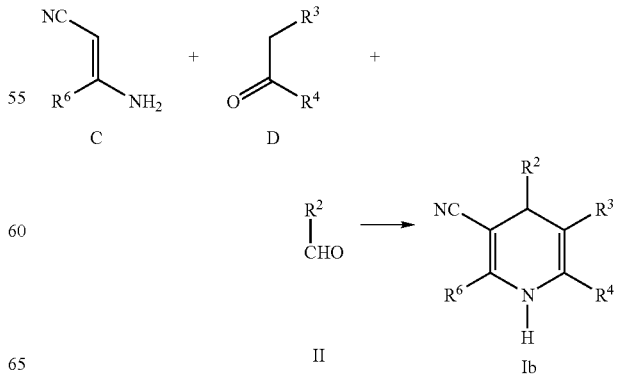

In general, compounds of formula Ib, as set forth above in Reaction Scheme 2, are prepared by mixing together a suitable amino nitrile C, a suitable ketone D and an aldehyde of formula II in ethanol, and heating the mixture to reflux for, e.g., 6 h [see, e.g., Arrowsmith, J. E., et al. *J. Med. Chem.*, 29, 1696-1702 (1986); Alker, D., et al. *J. Med. Chem.*, 33, 1805-1811 (1990)].

C. Preparation of Compounds of Formula Ic

Compounds of formula Ic are compounds of formula I wherein $R^1$ is hydrogen, $R^3$ is cyano, $R^5$ is as defined in the Summary but is not hydrogen, and $R^2$, $R^4$, and $R^6$ are defined as in the Summary. Compounds of formula Ic can be prepared as described below in Reaction Scheme 3, wherein G in G-$R^5$ is a leaving group, such as, for example, Cl, Br, I, tosylate, triflate, mesylate, or the like:

REACTION SCHEME 3

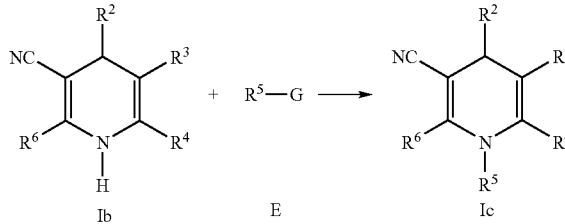

In general, compounds of formula Ic, as set forth above in Reaction Scheme 3, are prepared by deprotonation at the 1-position of the dihydropyridine with a base such as, for example, sodium hydride or $Cs_2CO_3$ and then reacting with a suitable electrophile E, in a suitable solvent such as, for example, DMF or THF.

D. Preparation of Compounds of Formulas Id-1 and Id-2

Compounds of formula Id-1 are compounds of formula I wherein $R^1$ is hydrogen, $R^3$ is cyano, $R^4$ and $R^5$ form an alkylene bridge (shown schematically in Reaction Scheme 4), $R^6$ is $C_{1-3}$alkyl and $R^2$ is defined as in the Summary. Compounds of formula Id-1 can be prepared as described below in Reaction Scheme 4:

REACTION SCHEME 4

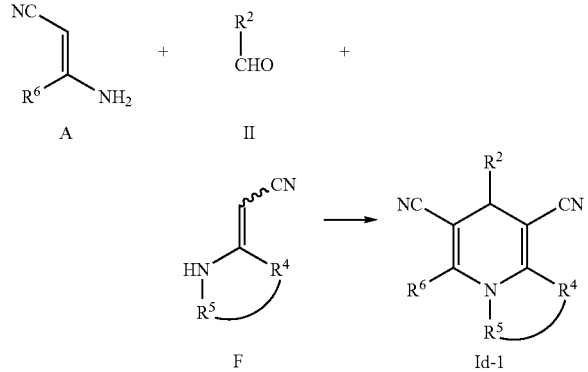

In general, compounds of formula Id-1, as set forth above, are prepared by reacting together an aldehyde of general formula II and a suitable amino nitrile F, at elevated temperature, preferably under reflux, after which a suitable aminonitrile A and acetic acid are added to the reaction, which is then heated at elevated temperature. In a preferred preparation, the amino nitrile F employed is 2-piperidinylidene-ethanenitrile and the amino nitrile A employed is 3-aminocrotononitrile.

Compounds of formula Id-2 are compounds of formula I wherein $R^1$ is hydrogen, $R^2$ is the entity ($R^2$-3), $R^3$ is cyano, $R^4$ and $R^5$ form an alkylene bridge (shown schematically in Reaction Scheme 5), $R^6$ is amino, and $R^2$ is defined as in the Summary. Compounds of formula Id-2 can be prepared as described below in Reaction Scheme 5:

REACTION SCHEME 5

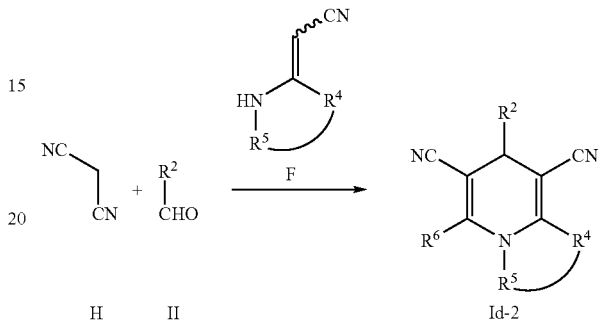

In general, compounds of formula Id-2, as set forth above, are prepared by mixing together an aldehyde of general formula II, malononitrile H and a suitable base, such as, for example, piperidine, after which is added a suitable amino nitrile F and the reaction mixture is then heated at elevated temperature, preferably under reflux. In a preferred preparation, the amino nitrile F employed is 2-piperidinylidene-ethanenitrile.

E. Preparation of Compounds of Formula Ie

Compounds of formula Ie are compounds of formula I wherein $R^1$ is hydrogen, $R^3$ is cyano, $R^4$ and $R^6$ are $C_{1-3}$alkyl (designated in Reaction Scheme 1 as R'), $R^5$ is as defined in the Summary but is not hydrogen, and $R^2$ is defined as in the Summary. Compounds of formula Ie can be prepared as described below in Reaction Scheme 6:

REACTION SCHEME 6

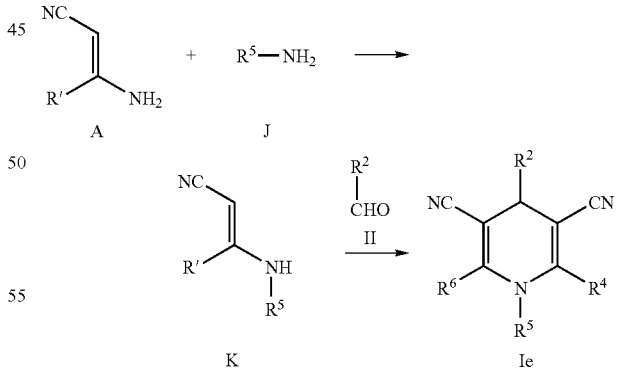

In general, compounds of formula Ie, as set forth above in Reaction Scheme 6, are prepared as follows. A suitable amino nitrile A is reacted with a suitable amine J, in a suitable solvent, such as, for example, ethanol, to produce an amino nitrile K. It will be apparent to the person skilled in the art that salts of amine J may also be suitable for the reaction, as they may be free based in situ by addition of a suitable base, such as, for example, pyridine. Suitable salts of amine J are for example, hydrochloride salts. The amino nitrile K, thus obtained, may be reacted with an aldehyde of general formula II via Hantzsch reaction as described above.

F. Preparation of Intermediates of Formula IIa

As described above, intermediates of formula IIa are used to make preferred compounds of formula I wherein A, B, D, X, Y, Z and $R^{10}$ are defined as in the summary. Intermediates of formula IIa may be be prepared from intermediates of formula III wherein A, B, D, X, Y, Z and $R^{10}$ are defined as in the summary and Q is hydrogen, halo, —$CH_2OH$, cyano, or —$CO_2R^{13}$, wherein $R^{13}$ is hydrogen, $C_{1-4}$-alkyl, or benzyl, as described below in Reaction Scheme 7:

REACTION SCHEME 7

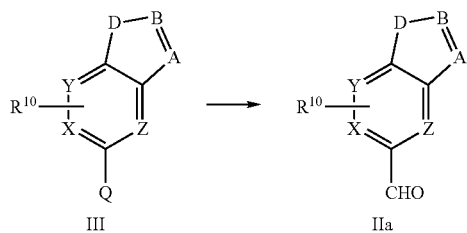

Suitable reaction conditions are based on the properties of the reactant, i.e. the nature of A, B, D, X, Y, Z, $R^{10}$ and Q, and can be determined by one skilled in the art without undue experimentation. In the case that Q is hydrogen, an intermediate of formula IIa may for example be prepared by way of a metalation, for example a de-protonation reaction with a suitable base such as lithium diisopropylamide, followed by quenching of the organometallic intermediate with a suitable formyl source such as DMF or a suitable alkyl formate, such as ethyl formate. In the case that Q is halo, an intermediate of formula IIa may for example be prepared by way of halogen-metal exchange reaction, followed by quenching of the organometallic intermediate with a suitable formyl source such as DMF or a suitable alkyl formate, such as ethyl formate. Alternatively a formylation reaction mediated by a suitable metal complex, such as for example a suitable palladium phosphine complex, such as $PdCl_2(PPh_3)_2$, in the presence of carbon monoxide and a suitable formate salt, such as sodium formate, may be employed. In the case that Q is —$CH_2OH$, a suitable oxidation reaction may be employed, such as, for example, using a suitable oxidizing agent, such as, for example, $MnO_2$, PCC, or $SO_3$-pyridine complex. In the case that Q is cyano, or —$CO_2R^{13}$, a suitable reduction reaction may be employed, such as, for example, using a suitable reducing agent, such as, for example, DIBAL-H, in a suitable solvent, such as THF, at low temperature, such as –100° C. to 0° C.

It is understood that other compounds of the invention not specifically disclosed in the above Reaction Schemes may be similarly prepared by one skilled in the art with the appropriate starting materials.

All compounds of the invention as prepared above that exist in free base or acid form may be converted to their pharmaceutically acceptable salts by treatment with the appropriate inorganic or organic base or acid. Salts of the compounds prepared above may be converted to their free base or acid form by standard techniques.

It is understood that all polymorphs, amorphous forms, anhydrates, hydrates, solvates and salts of the compounds of the invention are intended to be within the scope of the invention. Furthermore, all compounds of the invention which contain an ester group can be converted to the corresponding acid by methods known to one skilled in the art or by methods described herein. Likewise, compounds of the invention that contain a carboxylic acid group can be converted to the corresponding amide by amidation methods known to those skilled in the art. Amides may also be prepared from the corresponding amines by reaction with acid chlorides, or other suitable techniques. Other substitutions on the molecule can be performed by methods (such as hydrogenation, alkylation, reaction with acid chlorides, and the like) known to those of skill in the art without undue experimentation.

To prepare the cyclodextrin clathrates of this invention, the compounds of formula I, as defined above in the Summary of the Invention, can be dissolved in a pharmacologically acceptable solvent, such as, for example (but without limitation thereto) in an alcohol (preferably ethanol), in a ketone, (such as acetone) or in an ether (such as diethyl ether), and mixed with aqueous solutions of α-cyclodextrin, β-cyclodextrin or γ-cyclodextrin, preferably β-cyclodextrin, at 20° C. to 80° C.; or the acids of the compounds of formula I as defined above in the Summary of the Invention in the form of the aqueous solutions of their salts (e.g., sodium or potassium salts) can be admixed with a cyclodextrin and after solution with the equivalent amount of an acid (e.g., HCl or $H_2SO_4$) to afford the corresponding cyclodextrin clathrate.

At this point or after cooling, the corresponding cyclodextrin clathrates separate in the form of crystals. However, it is also possible to convert oily and also crystalline compounds of formula I, as defined above in the Summary of the Invention, by rather long stirring (e.g., for 1 hour to 14 days) at ambient temperature, by treatment with an aqueous solution of cyclodextrins, into the corresponding cyclodextrin clathrate form. The clathrates can then be isolated as solid, free-flowing crystals by suctioning off the solvents and drying. Cyclodextrins used in this invention are commercially available, for example, from Aldrich Chemical Co., or can be prepared by methods known to those skilled in the art. See, for example, Croft, A. P. et al., "Synthesis of Chemically Modified Cyclodextrins", *Tetrahedron* 1983, Vol. 39, No. 9, pp. 1417-1474. Suitable cyclodextrins will include a wide variety of those which produce clathrates of the compounds of formula I as set forth above. See, for example, J. E. F. Reynolds (ed.) Martindale, *The Extra Pharmacopoeia* 28th ed. The Pharmaceutical Press, London 1982, p. 333 and 389-390 and O.-A. Neumueller (ed.), *Roempps Chemie-Lexikon,* 8. Aufl. Franckh'sche Verlagshandlung, Stuttgart 1981, p. 763-764, 841, 1053-1054.

By selection of the suitable amounts of cyclodextrins and water it is possible to obtain the new clathrates in a stoichiometric composition with a reproducible content of effective substance. The clathrates can be used in a dry hygroscopic form or in a water-containing, but less hygroscopic form. A typical molar ratio of cyclodextrin to a compound of formula I is 2:1 (cyclodextrin:compound).

The compounds of the invention are inhibitors of c-Met-mediated diseases or c-Met-mediated conditions. The terms "c-Met-mediated disease" and "c-Met-mediated condition" mean any disease state or other deleterious condition in which c-Met is known to play a role. The terms "c-Met-mediated disease" and "c-Met-mediated condition" also mean those diseases or conditions that are alleviated by treatment with a c-Met inhibitor. Such diseases and conditions include, without limitation, cancers and other proliferative disorders. Accordingly, the compounds are useful in the treatment of, for example, the following diseases or disorders in mammals, particularly humans: esophageal, pancreatic, renal, gastric, colon, thyroid, brain, breast, prostate, lung and other solid-tumor cancers; atherosclerosis; regulation of angiogenesis; thrombosis; and lung fibrosis.

The compounds of this invention are also useful for the study of kinases in biological and pathological phenomena; the study of intracellular signal transduction pathways mediated by such kinases; and the comparative evaluation of new kinase inhibitors.

The compounds of the invention can be tested for their ability to inhibit c-Met kinase by various known in vitro or in vivo assays and by assays described herein. For example, in vitro assays include assays that determine inhibition of either the phosphorylation activity or ATPase activity of activated c-Met. Alternate in vitro assays quantitate the ability of the inhibitor to bind to c-Met. Inhibitor binding may be measured by radiolabelling the inhibitor prior to binding, isolating the inhibitor/c-Met complex and determining the amount of radiolabel bound. Alternatively, inhibitor binding may be determined by running a competition experiment where new inhibitors are incubated with c-Met bound to known radioligands. Detailed conditions for assaying a compound useful in the present invention as an inhibitor of c-Met kinase are set forth in the Biological Examples below.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included. The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term "aerosol" is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, biphasic, or triphasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors and can be determined routinely by one of ordinary skill in the art. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent can be administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

EXAMPLES

The following specific Synthetic Preparations (for the preparation of exemplary starting compounds), Synthetic Examples (for the preparation of the compounds of the invention) and Biological Examples (for the assays used to demonstrate the utility of the compounds of the invention) are provided as a guide to assist in the practice of the invention, and are not intended as a limitation on the scope of the invention. Where one or more NMR's are given for a particular compound, each NMR may represent a single stereoisomer, a non-racemic mixture of stereoisomers or a racemic mixture of the stereoisomers of the compound.

Synthetic Preparation 1

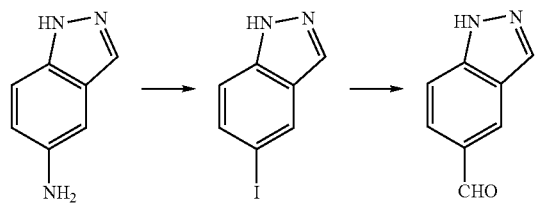

5-Aminoindazole (64.73 g, 486.13 mmol) was suspended in 600 mL water and ca. 600 mL ice, and conc. HCl (200 mL, 5759 mmol) was added. The mixture was cooled in an ice-salt bath to ca. −5° C. To this mixture was added, dropwise, a solution of sodium nitrite (37.34 g, 541.2 mmol) in 200 mL water (took about 1 hr). The internal temperature was kept below ca. +2° C. The resulting brown solution was stirred for a further 15 min at −5° C., then a solution of potassium iodide (97 g, 584.34 mmol) in 250 mL water was slowly added dropwise (took about 30 min). After complete addition, the reaction was heated to 90° C. for 1.5 hr. After allowing to cool, the solution was filtered to give a fine black solid and the filtrate was allowed to sit overnight in the refrigerator. The next day the filtrate was filtered again and the two solids were combined and dried to give 5-iodoindazole (126.63 g, 106%).

A mixture of 5-iodoindazole (10 g, 41 mmol), HCOONa (5.57 g, 82 mmol) and $PdCl_2(PPh_3)_2$ (1.44 g, 2.05 mmol) in DMF (60 mL) was put under vacuum and charged with carbon monoxide (CO). This process was repeated three times, after which the mixture was kept at 110° C. for 6 hr. After cooling to room temperature (rt), the reaction mixture was diluted with brine and extracted with EtOAc. The organic phases were combined, washed with brine, dried, and concentrated. The crude product was purified by column chromatography to afford 1H-indazole-5-carboxaldehyde (3.52 g, 59%) as a white solid.

Synthetic Preparation 2

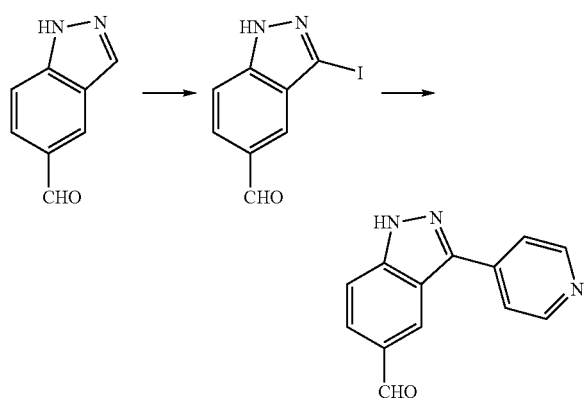

To a solution of 1H-indazole-5-carboxaldehyde (3.75 g, 25.7 mmol) in dioxane (120 mL) was added a solution of NaOH (15.48 g, 384.9 mmol) in water (120 mL). To this solution, iodine (8.2 g, 32 mmol) was added. After 1 hr at rt, more iodine (8.2 g, 32 mmol) was added, and the reaction mixture was stirred for an additional 1 hr at rt. After removal of most of the dioxane in vacuo, the reaction mixture was extracted with EtOAc, washed with brine, dried, and concentrated. The crude product was purified by flash chromatography to afford 3-iodo-1H-indazole-5-carboxaldehyde (4.5 g, 64.5%).

To a suspension of 3-iodo-1H-indazole-5-carboxaldehyde (200 mg, 0.74 mmol) and 4-pyridineboronic acid (110 mg, 0.89 mmol) in toluene/EtOH (1:1, 8 mL) in a sealed tube was added Na$_2$CO$_3$ (2 N, 1 mL) followed by Pd(PPh$_3$)$_4$ (85 mg, 0.074 mmol). The reaction mixture was put under vacuum, and re-charged with N$_2$ three times, then kept at ca. 100-110° C. for ca. 4-5 hr. The reaction mixture was cooled to rt, diluted with water, and extracted with EtOAc. The organic phase was washed with brine, and dried. Concentration followed by purification by flash chromatography afforded 3-(4-pyridinyl)-1H-indazole-5-carboxaldehyde (106 mg, 64%).

Synthetic Preparation 3

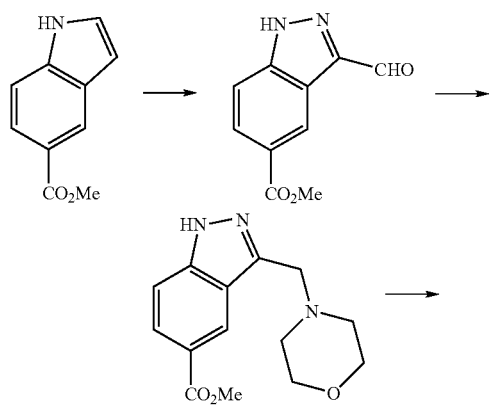

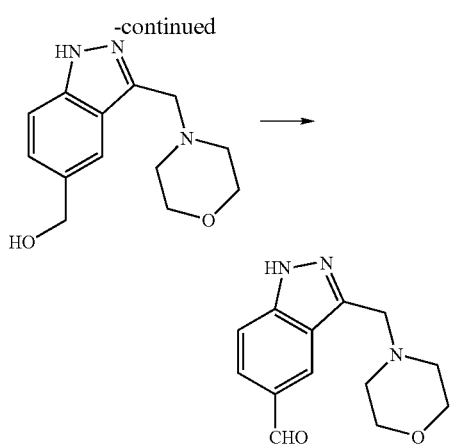

To a suspension of 1H-indole-5-carboxylic acid methyl ester (4 g, 22.83 mmol) in a solution of NaNO$_2$ (15.75 g, 228.33 mmol) in water (400 mL) was added HCl (conc.) dropwise until pH<2 at rt. The resulting mixture was stirred for a further 3 hr. The crude mixture was extracted with EtOAc (3×150 mL), washed with brine, dried, and concentrated. The crude product was purified by flash chromatography to afford 3-formyl-1H-indazole-5-carboxylic acid methyl ester (1.57 g, 32%).

To a solution of 3-formyl-1H-indazole-5-carboxylic acid methyl ester (600 mg, 2.94 mmol) in DCM was added HOAc (0.25 mL, 4.41 mmol) followed by morpholine (0.31 mL, 3.53 mmol) and NaHB(OAc)$_3$ (809.6 mg, 3.62 mmol) at rt. The reaction was stirred at rt overnight, and was quenched with brine. The reaction mixture was extracted with EtOAc, washed with brine, dried, and concentrated in vacuo. Purification by flash column afforded 3-(4-morpholinylmethyl)-1H-indazole-5-carboxylic acid methyl ester (800 mg, 95.7%).

To a suspension of LiAlH$_4$ in THF was added a solution of 3-(4-morpholinylmethyl)-1H-indazole-5-carboxylic acid methyl ester (400 mg, 1.45 mmol) in THF at 0° C. After about 2-3 hr, the reaction mixture was diluted with ether and quenched with 50% NaOH, and the solid was filtered off. The filtrate was concentrated, the residue was purified by column to afford the corresponding alcohol (100 mg). This alcohol (100 mg) was dissolved in DCM (10 mL) and PCC was added (100 mg) at rt. After 2 hr, the reaction was diluted with EtOAc, and the solid was filtered off. The filtrate was concentrated and the residue was purified by column to give 3-(4-morpholinylmethyl)-1H-indazole-5-carboxaldehyde (65 mg, 17% in two steps).

Synthetic Preparation 4

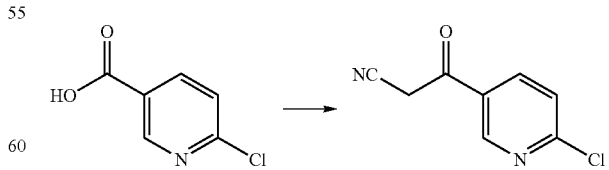

To a suspension of NaH (60%, 2.44 g, 57.72 mmol) in 30 mL of THF at 0° C. was added cyanoacetic acid 1,1-dimethylethyl ester (8.12 g, 57.72 mmol) over about 15 min. After addition, the ice bath was removed and the reaction was stirred for a further 30 min.

Carbonyldiimidazole (8.69 g, 53.59 mmol) was added to a solution of 2-chloro-5-pyridinecarboxylic acid (7.5 g, 47.6 mmol) in 125 mL of THF, and the mixture was stirred for 45 min. After cooling to −78° C., the nitrile solution prepared above was added to this reaction mixture dropwise over 20 min, and it was allowed to warm to rt over the weekend. The reaction was diluted with EtOAc, quenched with 1N NaHSO₄, and extracted. The combined organic phases was dried and concentrated to afford the crude product. This crude product was re-dissolved in formic acid, concentrated, and purified by column to afford 6-chloro-1′-oxo-3-pyridinepropanenitrile as a solid (8 g, 93%).

Synthetic Preparation 5

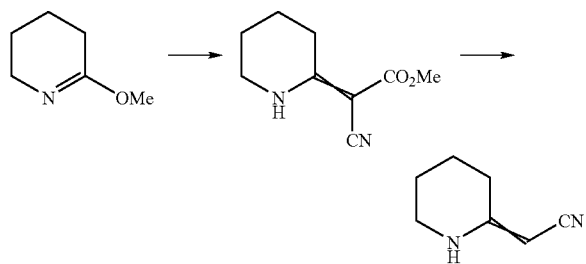

A mixture of 2,3,4,5-tetrahydro-6-methoxypyridine (1.1 g, 9.72 mmol) and cyanoacetic acid methyl ester (1 g, 10.1 mmol) in 40 mL THF was heated at 70° C. overnight. The reaction was cooled, and solvent was removed in vacuo. The resulting residue was purified on flash column to afford cyano-2-piperidinylidene-ethanoic acid methyl ester (1.4 g, 80%).

A suspension of cyano-2-piperidinylidene-ethanoic acid methyl ester (1.4 g, 7.76 mmol) in 25 mL 1M NaOH was heated at 100° C. for 30 mins. The reaction mixture was cooled to 0° C. and acidifed to pH 5-6 by adding conc. HCl, then extracted with 3×50 mL acetate. The organic phases were combined, dried, and concentrated. The crude product was purified on flash column to afford 2-piperidinylidene-ethanenitrile (590 mg, 62%).

Synthetic Preparation 6

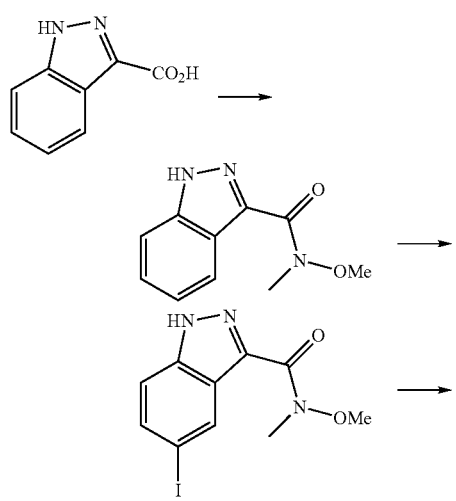

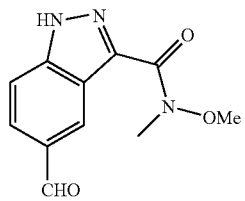

3-Carboxyindazole (10 g, 61.7 mmol) in DMF (100 mL) was treated with carbonyldiimidazole (11 g, 67.84 mmol) at rt with gas evolution for 15 min, after which the reaction mixture was heated up to 65° C. for 2 hours. After cooling to rt, N,O-dimethylhydroxyamine-HCl (4.14 g, 67.8 mmol) was added and the mixture was heated to 65° C. overnight. The reaction was cooled, quenched with water, extracted with CH₂Cl₂ and washed with water. The combined organic phase was dried and concentrated to afford N-methoxy-N-methyl-1H-indazole-3-carboxamide (10.3 g, 81.4%).

To a solution of N-methoxy-N-methyl-1H-indazole-3-carboxamide (12.4 g, 60.42 mmol) in CH₂Cl₂ (200 mL) was added bis(trifluoroacetoxy)iodobenzene (28.78 g, 66.74 mmol), followed by dropwise addition of iodine (9.22 g, 36.33 mmol) in CH₂Cl₂ at rt. The reaction was stirred overnight, after which 300 mL saturated NaHSO₃ was added and a solid began to precipitate, which was then filtered. The filtrate was concentrated and triturated with a small amount of CH₂Cl₂. The combined solids were dried to give 5-iodo-N-methoxy-N-methyl-1H-indazole-3-carboxamide (14.4 g, 72%) as a yellow solid.

A mixture of 5-iodo-N-methoxy-N-methyl-1H-indazole-3-carboxamide (5 g, 15.1 mmol), HCOONa (1.85 g, 30.2 mmol), and PdCl₂(PPh₃)₂ (320 mg, 0.453 mmol) in DMF (20 mL) was put under vacuum, and charged with CO. This process was repeated three times, and the mixture was kept at 110° C. for 6 hr. After cooling to rt, the reaction mixture was diluted with brine and extracted with EtOAc. The organic phases were combined, washed with brine, dried, and concentrated. The crude product was purified by column chromatography to afford 5-formyl-N-methoxy-N-methyl-1H-indazole-3-carboxamide (550 mg, 15.6%) as a white solid.

Synthetic Preparation 7

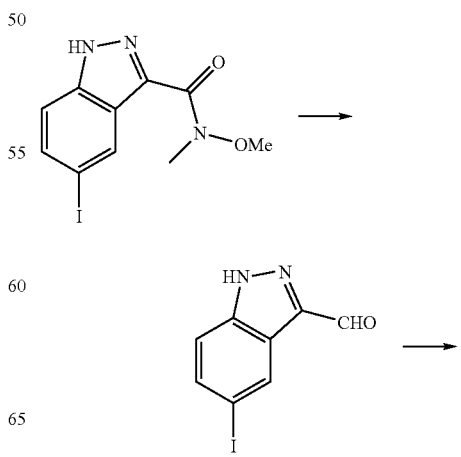

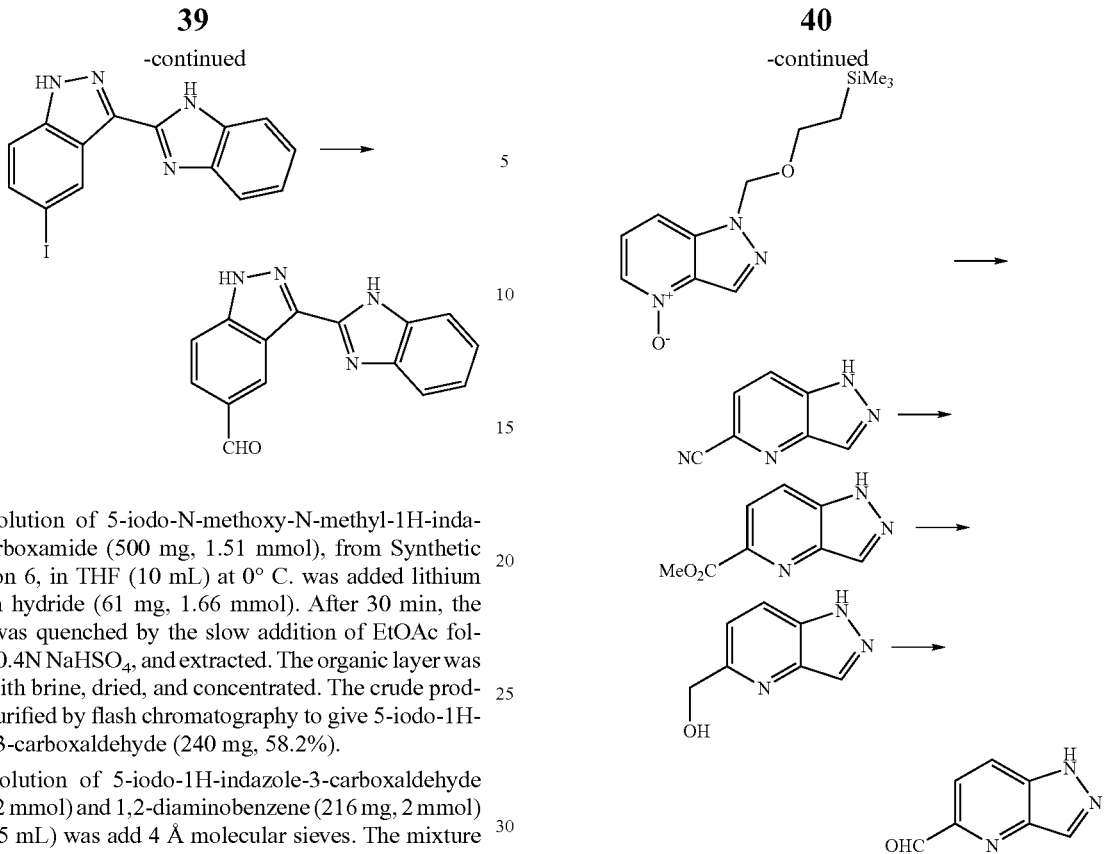

To a solution of 5-iodo-N-methoxy-N-methyl-1H-indazole-3-carboxamide (500 mg, 1.51 mmol), from Synthetic Preparation 6, in THF (10 mL) at 0° C. was added lithium aluminum hydride (61 mg, 1.66 mmol). After 30 min, the reaction was quenched by the slow addition of EtOAc followed by 0.4N $NaHSO_4$, and extracted. The organic layer was washed with brine, dried, and concentrated. The crude product was purified by flash chromatography to give 5-iodo-1H-indazole-3-carboxaldehyde (240 mg, 58.2%).

To a solution of 5-iodo-1H-indazole-3-carboxaldehyde (544 mg, 2 mmol) and 1,2-diaminobenzene (216 mg, 2 mmol) in DMF (5 mL) was add 4 Å molecular sieves. The mixture was kept at 60° C. for 2 hr, then the mixture was heated up to 80° C. overnight under air atmosphere (air balloon). The mixture was diluted with EtOAc, washed with water, dried and concentrated. The crude product was purified by flash chromatography to afford 3-(1H-benzimidazol-2-yl)-5-iodo-1H-indazole (500 mg, 69%).

3-(1H-benzimidazol-2-yl)-5-iodo-1H-indazole (500 mg, 1.39 mmol) was dissolved in DMF (5 mL), then $Pd(PPh_3)_2Cl_2$ (24 mg, 0.034 mmol) and sodium formate (142 mg, 2.1 mmol) were added. The reaction mixture was put under vacuum and recharged with CO three times, then heated up to 90° C. for 4 hr. The mixture was diluted with EtOAc, washed with brine, dried and concentrated. The crude product was purified by flash chromatography to afford 3-(1H-benzimidazol-2-yl)-1H-indazole-5-carboxaldehyde (135 mg, 37%) as yellow solid.

Synthetic Preparation 8

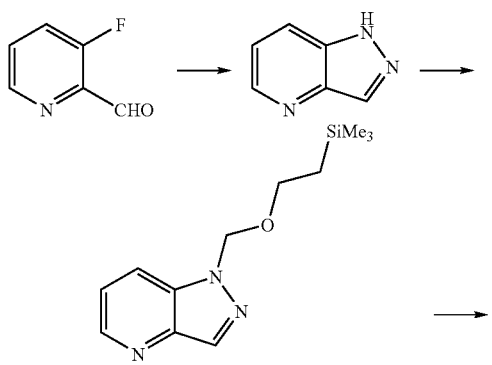

A mixture of 3-fluoro-2-pyridinecarboxaldehyde (4 g, 32 mmol) and hydrazine (20.5 g) was kept at 115° C. for 7 hr, then cooled to rt. The reaction mixture was diluted with water and extracted with EtOAc. The organic phases were combined, washed with brine, and dried. Concentration followed by flash chromatography afforded 1H-pyrazolo[4,3-b]pyridine (2.3 g, 60.4%).

KOtBu (2.38 g, 21.24 mmol) was added to a solution of 1H-pyrazolo[4,3-b]pyridine (2.3 g, 19.3 mmol) in THF (60 mL) at 0° C. After stirring at 0° C. for 1 hr, trimethylsilylethoxymethyl chloride (3.54 g, 21.24 mmol) was added. The reaction mixture was kept at 0° C. for 1 hr with stirring, then 1.5 hr at rt. The mixture was diluted with EtOAc and water and extracted with EtOAc. The combined organic phases were washed with brine, dried with $Na_2SO_4$, and concentrated. The crude product was purified by flash chromatography to afford 1-[[2-(trimethylsilyl)ethoxy]methyl]-1H-pyrazolo[4,3-b]pyridine in (2.32 g, 48%) and the regioisomer.

To a solution of 1-[[2-(trimethylsilyl)ethoxy]methyl]-1H-pyrazolo[4,3-b]pyridine (2.32 g, 9.3 mmol) in DCM (100 mL) at 0° C. was added mCPBA (1.77 g, 10.23 mmol). After 1 hr, the ice-bath was removed and the reaction mixture was stirred at rt overnight. The reaction mixture was diluted with DCM, washed with $NaHCO_3$ (sat.), and dried. Concentration followed by purification with flash chromatography afforded 4-hydroxy-1-[[2-(trimethylsilyl)ethoxy]methyl]-1H-pyrazolo[4,3-b]pyridinium (2.43 g, 98%) as a white solid.

To a solution of 4-hydroxy-1-[[2-(trimethylsilyl)ethoxy]methyl]-1H-pyrazolo[4,3-b]pyridinium (1.59 g, 6 mmol) in DCM (130 mL) was added TMSCN (1.13 mL, 9 mmol). After 5 min at rt, $(Me)_2N(C(O)Cl$ (0.83 mL, 9 mmol) was added. The reaction mixture was stirred at rt for 4 days, after which it was diluted with DCM, washed with brine, and dried.

Concentration followed by purification through column afforded 1H-pyrazolo[4,3-b]pyridine-5-carbonitrile (1 g, 61%).

A suspension of 1H-pyrazolo[4,3-b]pyridine-5-carbonitrile (1.89 g, 6.89 mmol) in MeOH (10 mL) and HCl (conc. 10 mL) was heated to reflux for 6 hr. After cooling to rt, the reaction mixture was concentrated to dryness. This crude product was dried under vacuum overnight, and re-dissolved in MeOH. To this solution, HCl gas was bubbled, and the resulting solution was refluxed for 20 hr. After cooling to rt, most of the solvent was removed under vacuum. The residue was diluted with EtOAc and treated with NaHCO₃ (sat.) to pH 10. The reaction mixture was extracted with EtOAc, washed with brine, and dried. Concentration followed by purification with column afforded 1H-pyrazolo[4,3-b]pyridine-5-carboxylic acid, methyl ester (720 mg, 59%).

1H-pyrazolo[4,3-b]pyridine-5-carboxylic acid, methyl ester (420 mg, 2.37 mmol) was dissolved in THF (30 mL) and cooled to 0° C. LiAlH₄ (360 mg, 9.48 mmol) was added in one portion. The mixture was stirred at 0° C. for 3 hr, and diluted with ether. 50% NaOH (5 mL) was added to quench the reaction, and the solid was filtered off through Celite. The filtrate was concentrated, and the residue was purified by flash chromatography to afford 1H-pyrazolo[4,3-b]pyridine-5-methanol (270 mg, 76.4%).

1H-pyrazolo[4,3-b]pyridine-5-methanol (240 mg, 1.61 mmol) was dissolved in DCM (24 mL) at rt, and DMSO (5.71 mL, 80.45 mmol) and NEt₃ (1.12 mL, 8.05 mmol) were added. After 10 min, SO₃-pyridine was added, and the mixture was stirred at rt for ca. 1.5 hr. The reaction was quenched with sat. NH₄Cl solution, stirred for 10 min, then extracted with DCM, washed with water and with brine, and dried with Na₂SO₄. The crude product (orange oil) was purified by a short manual flash column (hex/EtOAc 1:1) to afford 1H-pyrazolo[4,3-b]pyridine-5-carboxaldehyde (62 mg, 26.2%) as a white solid.

Synthetic Preparation 9

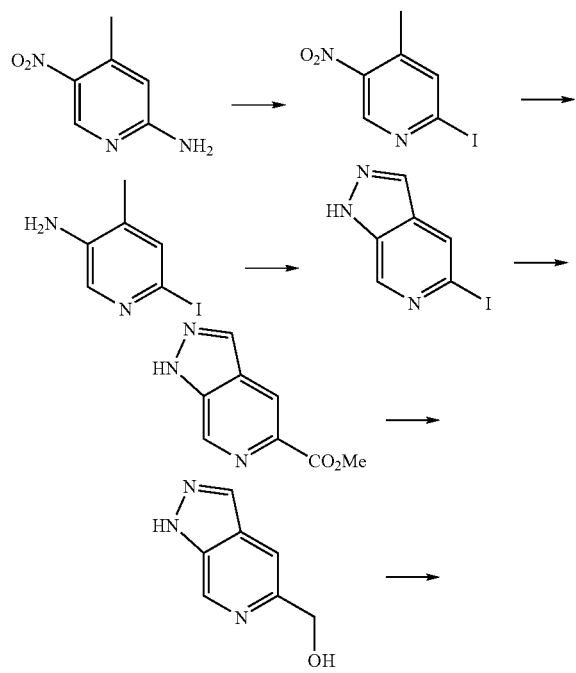

-continued

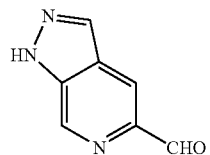

To a solution of 4-methyl-5-nitro-2-pyridinamine (12 g, 78.35 mmol) in diiodomethane (100 mL) was added isoamyl nitrite (22 mL, 160.4 mmol) at rt. After stirring for 30 min, the reaction was kept at 80° C. for 2 hr. The reaction was cooled and concentrated; but most of the diiodomethane remained. The crude mixture was loaded into column directly and eluted with 10% of EtOAc in hexane, and 2-iodo-4-methyl-5-nitropyridine (5.7 g, 28%) was obtained as a yellow solid after the removal of solvents under reduced pressure.

To a solution of SnCl₂.H₂O (20.5 g, 108 mmol) in EtOAc (200 mL) was added 2-iodo-4-methyl-5-nitropyridine (5.7 g, 21.6 mmol) in EtOAc (20 mL). Heat was released, and the reaction mixture was kept at reflux for 2 hr. After cooling to rt, the reaction mixture was treated with 50% NaOH (50 mL). Solid was filtered off and washed with EtOAc. The filtrate was washed with brine, dried, and concentrated to afford 2-iodo-4-methyl-5-pyridinamine (5 g, 99%) as a yellow solid.

To a suspension of 2-iodo-4-methyl-5-pyridinamine (5 g, 21.4 mmol) in toluene (340 mL) was added HOAc (19 mL), and the mixture was stirred vigorously until it became clear. Then KOAc (15.78 g, 160.23 mmol) was added. To this white suspension, isoamyl nitrite (3.16 mL, 23.5 mmol) was added dropwise at rt, and the resulting mixture was stirred for 2 days. The reaction mixture was diluted with EtOAc and treated with NaHCO₃ (sat.) to pH 10. The reaction mixture was extracted with EtOAc, washed with brine, dried, and concentrated in vacuo to afford the crude product. Purification by flash chromatography afforded 5-iodo-1H-pyrazolo[3,4-c]pyridine (4.37 g, 83.5%).

5-Iodo-1H-pyrazolo[3,4-c]pyridine (2.1 g, 8.57 mmol), Pd(PPh₃)₂Cl₂ (600 mg, 0.86 mmol), DMSO (1.92 mL, 27 mmol), and NEt₃ (2.68 mL, 19.4 mmol) were mixed in MeOH (210 mL) in a pressure tube (1 L hydrogenation vessel) and closed with a septum. The mixture was degassed under reduced pressure and recharged with carbon monoxide three times, then sealed. The reaction mixture was kept at 105° C. overnight. The reaction was cooled to rt, and most of the MeOH was removed in vacuo. The resulting residue was diluted with EtOAc, washed with brine, and dried. Concentration followed by purification through flash chromatography afforded 1H-pyrazolo[3,4-c]pyridine-5-carboxylic acid, methyl ester (1.5 g, 99%).

To a solution of 1H-pyrazolo[3,4-c]pyridine-5-carboxylic acid, methyl ester (1.5 g, 8.5 mmol) in THF (350 mL) at 0° C. was added LAH (958 mg) in two portions. The reaction was stirred at 0° C. for 1.5 hr, and at rt for 1 hr. The reaction was quenched with con. NaOH at 0° C., and the solid was filtered off and washed with MeOH. The filtrate was concentrated. Purification by column afforded 1H-pyrazolo[3,4-c]pyridine-5-methanol (1.23 g, 96%).

1H-pyrazolo[3,4-c]pyridine-5-methanol (1.08 g, 7.27 mmol) was dissolved in DCM (120 mL) at rt, and DMSO (30 mL) and NEt₃ (3.01 mL, 21.7 mmol) were added. After stirring for 10 min, SO₃-pyridine (3.45 g, 13.45 mmol) was added. The mixture stirred at rt for ca. 1.5 hr, and quenched with sat. NH₄Cl solution. The reaction mixture was extracted with DCM, washed with water and with brine, and dried with Na₂SO₄. The crude product was purified by a flash column to afford 1H-pyrazolo[3,4-c]pyridine-5-carboxaldehyde (220 mg, 21%).

Synthetic Preparation 10

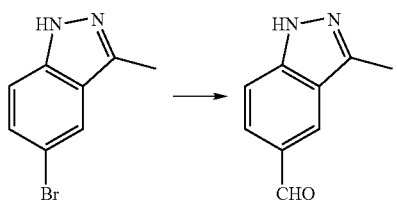

To chilled tetrahydrofuran (600 mL) at −78° C., under Argon, was added 200 mL of a 1.7M solution of tert-butyl-lithium in n-pentane. After 15 minutes at −78° C., a solution of 22.4 g (106.13 mmol) 5-bromo-3-methyl-1H-indazole (commercially available, or see WO 2006/081230, 68-69) in 300 mL tetrahydrofuran was added dropwise at such a rate that the temperature of the solution did not exceed −70° C. The mixture was stirred for 30 minutes before 24.5 mL N,N-dimethylformamide was added dropwise. After 20 minutes the cooling bath was removed and stirring continued for 1 hour before 41 mL water was added carefully. A further 201 mL water was added and the mixture was extracted with ethyl acetate. The organic extract was washed with saturated sodium chloride solution and dried over sodium sulfate. The solvents were distilled off to give 18.5 g crude 3-methyl-1H-indazole-5-carbaldehyde, which was used without purification. 1H-NMR (DMSO-d6): δ=13.13 (br s, 1H), 10.01 (s, 1H), 8.40 (s, 1H), 7.81 (d, 1H), 7.58 (d, 1H), 2.56 (s, 3H) ppm. MS (ES+): 161.34 (M⁺+1, 100%).

Synthetic Preparation 11

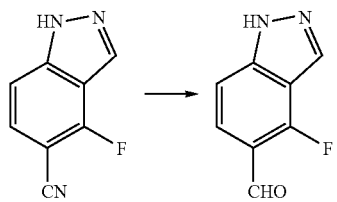

805 mg (5 mmols) 4-fluoro-1H-indazole-5-carbonitrile (see EP 1510516, Example 85) were suspended in 25 mL toluene and cooled to −40° C. During 15 minutes 8 mL of a 1.5 M solution of diisobutylaluminium hydride in toluene (12 mmols) were added dropwise. The mixture was stirred for 2 hours at −40° C. At this temperature 5 mL ethyl acetate were added and the mixture was stirred for 20 minutes. 5 mL of a 1 M aqueous solution of tartaric acid were added and the mixture was stirred for 30 minutes at −20 to 0° C. The insolubles were removed by filtration. A small amount of dilute aqueous citric acid was added and the mixture was extracted with ethyl acetate. The extracts were washed with saturated sodium chloride and sodium hydrogen carbonate solutions and dried over sodium sulfate. The crude product was purified with column chromatography to yield 4-fluoro-1H-indazole-5-carbaldehyde 762 mg (92.9%). 1H-NMR (DMSO-d6): 13.82 (br s, 1H); 10.32 (s, 1H); 8.44 (s, 1H); 7.74 (dd, 1H); 7.49 (d, 1H) ppm.

Synthetic Example 1

2-Fluoro-5-formylbenzonitrile (30 g, 201.17 mmol) and 3-aminocrotononitrile (35.01 g, 431.63 mmol) were dissolved in acetic acid and heated to 90° C. After 4 hr, the reaction mixture was cooled to rt, concentrated, neutralized with a saturated solution of sodium bicarbonate, and extracted with ethyl acetate. The organic extracts were dried over sodium sulfate and concentrated. The solid were dissolved into ethyl acetate, and hexane was added. The solid precipitated, and was filtered to afford 4-(3-cyano-4-fluorophenyl)-1,4-dihydro-2,6-dimethyl-3,5-pyridinedicarbonitrile (44.9 g, 80.2%) as a pale yellow solid. 1H-NMR (400 MHZ, DMSO-D6): δ=9.61 (br. s, 1H), 7.97 (dd, 1H), 7.48 (dd, 1H), 7.35 (dd, 1H), 4.64 (s, 1H), 2.01 (s, 6H) ppm.

Synthetic Example 2

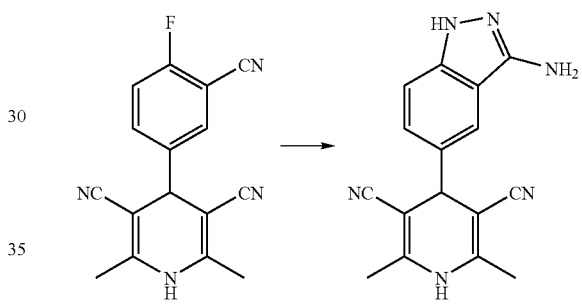

A mixture of 4-(3-cyano-4-fluorophenyl)-1,4-dihydro-2,6-dimethyl-3,5-pyridinedicarbonitrile (9.5 g, 34.14 mmol), from Synthetic Example 1, and hydrazine hydrate (10 g, 312 mmol) in n-butyl alcohol (75 mL) was kept at 80° C. for 5 hr. The mixture was cooled and concentrated. Sodium bicarbonate solution (sat.) was added to the residue, and the mixture was extracted with ethyl acetate. The organic phases were combined, dried, and concentrated to afford 4-(3-amino-1H-indazol-5-yl)-1,4-dihydro-2,6-dimethyl-3,5-pyridinedicarbonitrile (5.6 g, 57.01%) as a pale yellow solid (Cpd. No. 82, Table 2). 1H-NMR (300 MHZ, DMSO-D6): δ=11.39 (br. s, 1H), 9.47 (br. s, 1H), 7.50 (m, 1H), 7.20 (d, 1H), 7.11 (dd, 1H), 5.34 (br. s, 2H), 4.34 (s, 1H), 2.01 (s, 6H) ppm.

Synthetic Example 3

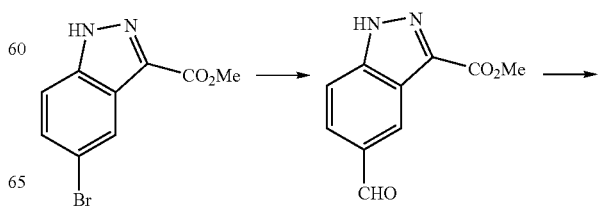

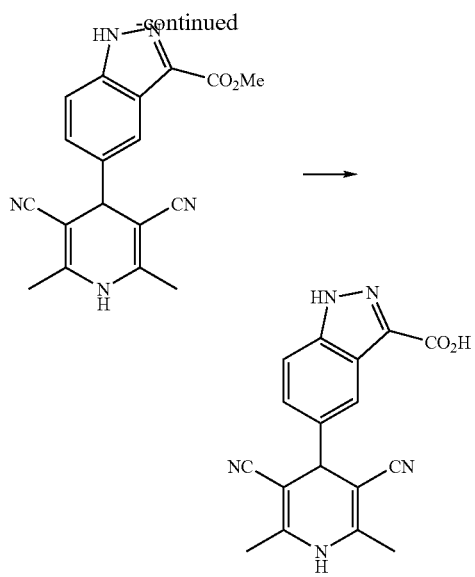

A: A mixture of 5-bromo-1H-indazole-3-carboxylic acid methyl ester (1 g, 3.92 mmol), HCOONa (400 mg, 5.88 mmol), and PdCl$_2$(PPh$_3$)$_2$ (138 mg, 0.2 mmol) in DMF (10 mL) was put under vacuum, and charged with CO. This process was repeated three times, and the mixture was kept at 110° C. for 6 hr. The reaction mixture was cooled to rt, diluted with EtOAc and water, and extracted. The organic phase was dried and concentrated. Purification via flash chromatography afforded 5-formyl-1H-indazole-3-carboxylic acid methyl ester (430 mg, 54%).

A mixture of 5-formyl-1H-indazole-3-carboxylic acid methyl ester (92 mg, 0.45 mmol) and aminocrotononitrile (74 mg, 0.9 mmol) in HOAc (1 mL) was kept at 110° C. for 15 mins. After cooling to rt, the reaction mixture was diluted with EtOAc, washed with brine, dried, and concentrated. The crude product was purified by TLC to afford 5-(3,5-dicyano-1,4-dihydro-2,6-dimethyl-4-pyridinyl)-1H-indazole-3-carboxylic acid methyl ester (133 mg, 89%) (Cpd. No. 85, Table 2). 1H-NMR (400 MHz, DMSO-D6): δ=8.04 (s, 1H), 7.72 (s, 1H), 7.49 (d, 1H), 4.58 (s, 1H), 4.02 (s, 3H), 2.0 (s, 6H) ppm.

B: To 5-(3,5-dicyano-1,4-dihydro-2,6-dimethyl-4-pyridinyl)-1H-indazole-3-carboxylic acid methyl ester (110 mg, 0.33 mmol) in MeOH—H$_2$O (1:1, 8 mL) was added LiOH (1.08 g, 26.4 mmol) at rt. The reaction mixture was heated up to 70° C. for 2 days. After cooling to rt, the solution was acidified to pH 7 with 1 N HCl. After the removal of MeOH, the residue was purified by HPLC to afford 5-(3,5-dicyano-1,4-dihydro-2,6-dimethyl-4-pyridinyl)-1H-indazole-3-carboxylic acid (98 mg, 93%) (Cpd. No. 86, Table 2). 1H-NMR (400 MHz, DMSO-D6): δ=8.04 (s, 1H), 7.78 (s, 1H), 7.41 (d, 1H), 4.62 (s, 1H), 2.1 (s, 6H) ppm.

Synthetic Example 4

A mixture of 1H-indazole-5-carboxaldehyde from Synthetic Preparation 1 (447 mg, 3.1 mmol) and 3-aminocrotononitrile (526.4 mg, 6.41 mmol) in HOAc (10 mL) was kept at 110° C. for 1.5 hr, after which it was cooled to rt. The reaction was treated with NaHCO$_3$ (sat.) to pH 10, and extracted with EtOAc. The organic phases were combined, washed with brine, and dried. Concentration followed by purification with flash chromatography afforded 1,4-dihydro-4-(1H-indazol-5-yl)-2,6-dimethyl-3,5-pyridinedicarbonitrile (370 mg, 44%) (Cpd. No. 80, Table 2). 1H-NMR (400 MHz, CDCl$_3$): δ=8.07 (s, 1H), 7.64 (s, 1H), 7.53 (d, 1H), 7.35 (d, 1H), 4.48 (s, 1H), 2.03 (s, 6H) ppm.

Synthetic Example 5

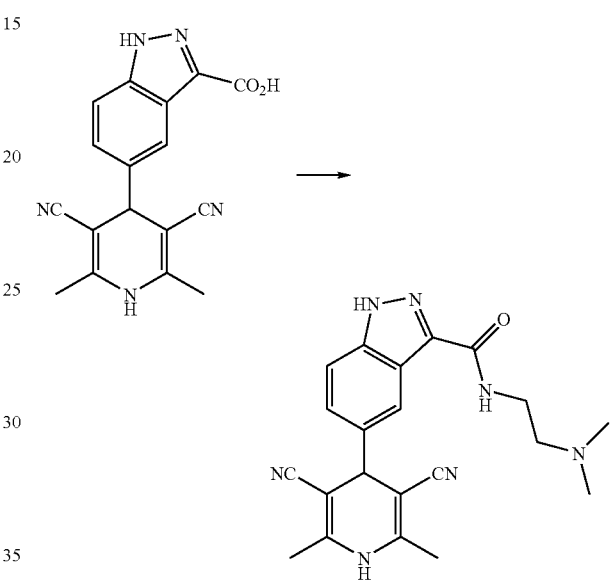

To a solution of 5-(3,5-dicyano-1,4-dihydro-2,6-dimethyl-4-pyridinyl)-1H-indazole-3-carboxylic acid (300 mg, 0.94 mmol), from Synthetic Example 3, in DMF (5 mL) was added Et$_3$N (476 mg, 4.7 mmol) and HATU (430 mg, 1.13 mmol). The mixture was stirred at rt for 30 min, then N,N-dimethylethylenediamine (167.2 mg, 1.9 mmol) was added. The mixture was kept at rt overnight, and then quenched with water. The reaction mixture was extracted with CH$_2$Cl$_2$, dried, and concentrated. The residue was purified by flash chromatography followed by HPLC to afford 5-(3,5-dicyano-1,4-dihydro-2,6-dimethyl-4-pyridinyl)-N-[2-(dimethylamino)ethyl]-1H-indazole-3-carboxamide (121 mg, 33.7%) (Cpd. No. 103.2, Table 2). 1H-NMR (400 MHz, DMSO-D6): δ=8.16 (s, 1H), 7.63 (d, 1H), 7.41 (d, 1H), 4.55 (s, 1H), 3.82 (t, 2H), 3.43 (t, 2H), 3.01 (s, 6H), 2.14 (s, 6H) ppm.

Synthetic Example 6

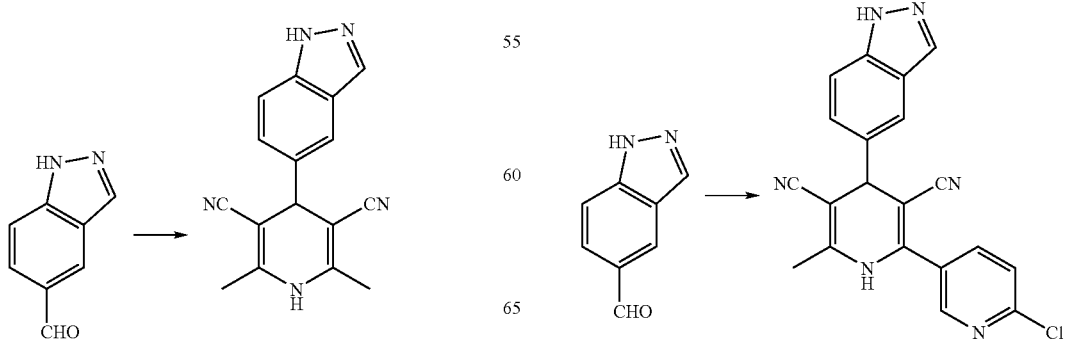

A mixture of 6-chloro-2'-oxo-3-pyridinepropanenitrile (1.2 g, 6.64 mmol), from Synthetic Preparation 4, and 1H-indazole-5-carboxaldehyde (0.81 g, 5.54 mmol) was kept at reflux in EtOH (50 mL) for 15 min, and 3-aminocrotononitrile (475 mg, 5.79 mmol) was added. The reaction mixture was kept at reflux for 2 hr, then HOAc was added. The reaction mixture was heated to reflux for 1.5 hr, and cooled to rt. All solvents were removed under vacuum, and the crude product was purified by column to afford 1,4-dihydro-2-(4-chloropyrid-3-yl)-6-methyl-4-(1H-indazol-5-yl)-3,5-pyridinedicarbonitrile (974 mg, 39.3%) (Cpd. No. 270, Table 5). 1H-NMR (400 MHz, DMSO-D6): δ=13.10 (s, 1H), 9.70 (s, 1H), 8.32 (s, 1H), 8.10 (s, 1H), 7.75 (m, 2H), 7.60 (m, 1H), 7.39 (m, 1H), 6.95 (m, 1H), 4.64 (s, 1H), 3.70 (m, 4H), 3.55 (m, 4H), 2.13 (s, 3H) ppm.

Synthetic Example 7

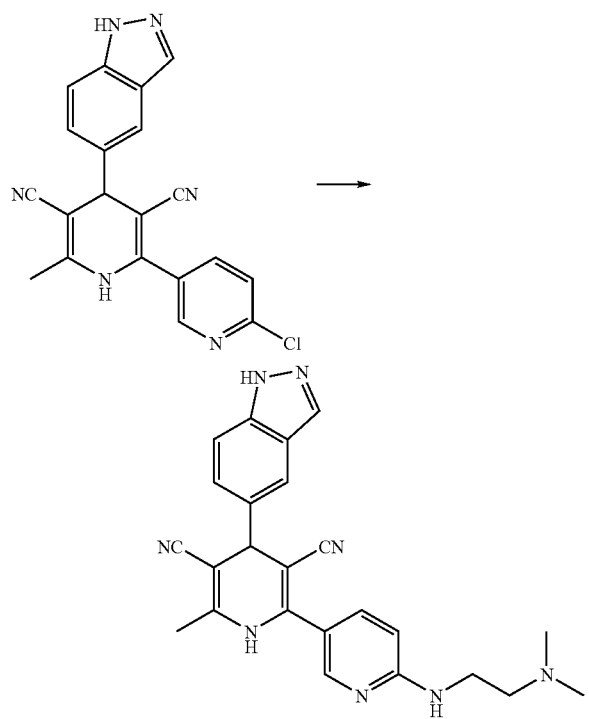

A mixture of 1,4-dihydro-2-(4-chloropyrid-3-yl)-6-methyl-4-(1H-indazol-5-yl)-3,5-pyridinedicarbonitrile from Synthetic Example 6 (160 mg, 0.43 mmol) and 2-N,N-dimethylethylenediamine (5 mL, 45.55 mmol) was heated to reflux for 5 hr, and cooled to rt. The reaction mixture was diluted with EtOAc, washed with 1N NaHSO$_4$ and brine, and dried. Concentration followed by purification through column afforded the product 1,4-dihydro-2-[4-(2-dimethylamino)ethylamino-pyrid-3-yl]-6-methyl-4-(1H-indazol-5-yl)-3,5-pyridinedicarbonitrile (29.1 mg, 16%) (Cpd. No. 275, Table 5). 1H-NMR (400 MHz, DMSO-D6): δ=13.10 (s, 1H), 9.60 (s, 1H), 8.19 (m, 1H), 8.10 (s, 1H), 7.75 (s, 1H), 7.60 (m, 1H), 7.52 (m, 1H), 7.39 (m, 1H), 7.00 (m, 1H), 6.58 (m, 1H), 4.60 (s, 1H), 3.40 (m, 2H), 2.40 (m, 2H), 2.20 (s, 6H), 2.10 (s, 3H) ppm.

Synthetic Example 8

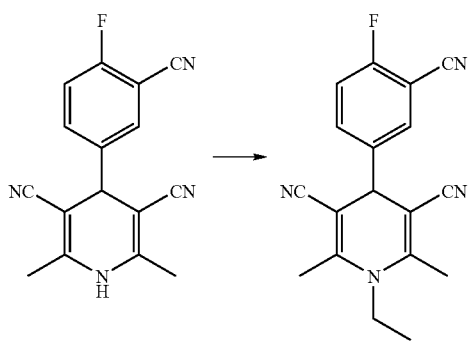

To a solution of 4-(3-cyano-4-fluorophenyl)-1,4-dihydro-2,6-dimethyl-3,5-pyridinedicarbonitrile (1 eq), from Synthetic Example 1, in DMF was added either NaH or Cs$_2$CO$_3$ (1.2 eq) at 0° C. After 30 min, ethyl chloride was introduced. The reaction mixture was stirred at rt overnight, and quenched with brine. The reaction mixture was extracted with EtOAc, washed with brine, and dried. Concentration followed by flash chromatography gave 1-ethyl-4-(3-cyano-4-fluorophenyl)-1,4-dihydro-2,6-dimethyl-3,5-pyridinedicarbonitrile. 1H-NMR (400 MHz, DMSO-D6): δ=7.86 (dd, 1H), 7.69 (m, 1H), 7.55 (t, 1H), 4.57 (s, 1H), 3.12 (q, 2H), 2.1 (s, 6H), 1.4 (t, 3H) ppm.

Synthetic Example 9

A mixture of 1-ethyl-4-(3-cyano-4-fluorophenyl)-1,4-dihydro-2,6-dimethyl-3,5-pyridinedicarbonitrile (1 eq), from Synthetic Example 8, and hydrazine hydrate (110 eq) in n-butyl alcohol (75 mL) was kept at 80° C. for 5 hr. The mixture was cooled and concentrated. To the residue, sodium bicarbonate solution (sat.) was added and the mixture was extracted with ethyl acetate. The organic phases were combined, dried, and concentrated to afford 1-ethyl-4-(3-amino-1H-indazol-5-yl)-1,4-dihydro-2,6-dimethyl-3,5-pyridinedicarbonitrile (Cpd. No. 294, Table 7). 1H-NMR (400 MHz, DMSO-D6): δ=11.43 (s, 1H), 7.51 (s, 1H), 7.26 (d, 1H), 7.12 (d, 1H), 5.37 (s, 2H), 4.32 (s, 1H), 3.67 (q, 2H), 2.27 (s, 6H), 1.18 (t, 3H) ppm.

Synthetic Example 10

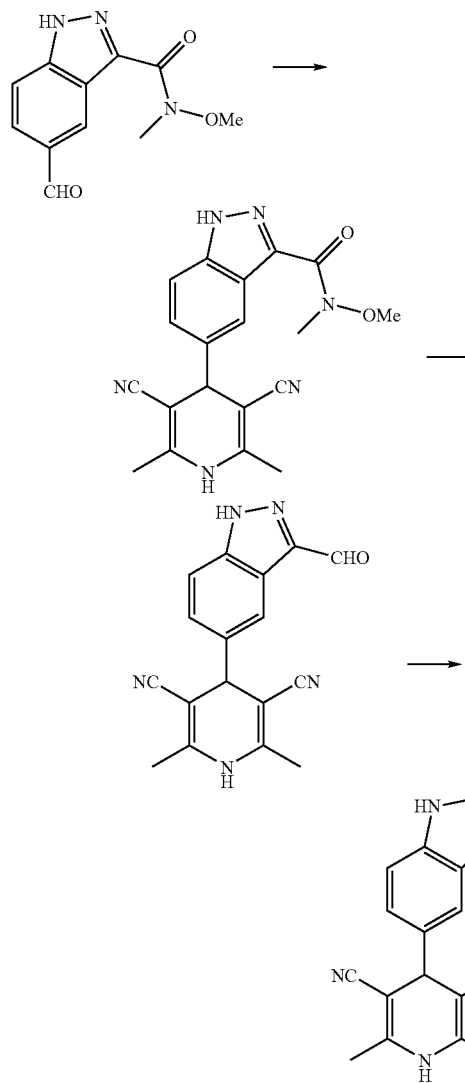

A: A mixture of 5-formyl-N-methoxy-N-methyl-1H-indazole-3-carboxamide (400 mg, 1.72 mmol) from Synthetic Preparation 6, and 3-aminocrotononitrile (299 mg, 2.12 mmol) in HOAc (5 mL) was kept at 110° C. for 2 hr. After cooling to rt, the reaction mixture was diluted with EtOAc, washed with brine, dried, and concentrated. The crude product was purified by flash chromatography to afford 5-(3,5-dicyano-1,4-dihydro-2,6-dimethyl-4-pyridinyl)-N-methoxy-N-methyl-1H-indazole-3-carboxamide (500 mg, 80.5%) (Cpd. No. 143, Table 2). 1H-NMR (400 MHz, DMSO-D6): δ=9.65 (s, 1H), 7.85 (s, 1H), 7.65 (d, 1H), 7.38 (d, 1H), 4.58 (s, 1H), 3.78 (s, 3H), 3.44 (s, 3H), 2.03 (s, 6H) ppm.

B: Lithium aluminum hydride (45 mg, 1.2 mmol) was added portion-wise to a cooled solution of 5-(3,5-dicyano-1,4-dihydro-2,6-dimethyl-4-pyridinyl)-N-methoxy-N-methyl-1H-indazole-3-carboxamide (340 mg, 0.94 mmol) in THF (20 mL). After 30 min, the mixture was heated up to 60° C. After 2 hr, the reaction was quenched by the slow addition of ethyl acetate at 5° C. and 0.4 N NaHSO$_4$. The organic layer was washed with brine, dried with Na$_2$SO$_4$, and concentrated. The crude product was purified by column to give 4-(3-formyl-1H-indazol-5-yl)-1,4-dihydro-2,6-dimethyl-3,5-pyridinedicarbonitrile (200 mg, 70%) (Cpd. No. 145, Table 2). 1H-NMR (400 MHz, DMSO-D6): δ=10.18 (s, 1H), 9.58 (s, 1H), 7.98 (d, 1H), 7.76 (d, 1H), 7.46 (d, 1H), 4.65 (s, 1H), 2.03 (s, 6H) ppm.

C: To a suspension of 4-(3-formyl-1H-indazol-5-yl)-1,4-dihydro-2,6-dimethyl-3,5-pyridinedicarbonitrile (200 mg, 0.66 mmol) in MeOH was added NaBH$_4$ (50 mg) at rt. After 1 hr, the reaction was diluted with brine, extracted with EtOAc, washed with water, and dried. Concentration followed by purification through flash chromatography afforded 1,4-dihydro-4-[3-(hydroxymethyl)-1H-indazol-5-yl]-2,6-dimethyl-3,5-pyridinedicarbonitrile (100 mg, 50%) as a yellow solid (Cpd. No. 144, Table 2). 1H-NMR (400 MHz, DMSO-D6): δ=9.55 (s, 1H), 7.68 (s, 1H), 7.52 (d, 1H), 7.26 (d, 1H), 5.24 (t, 1H), 4.78 (d, 2H), 4.55 (s, 1H), 2.03 (s, 6H) ppm.

Synthetic Example 11

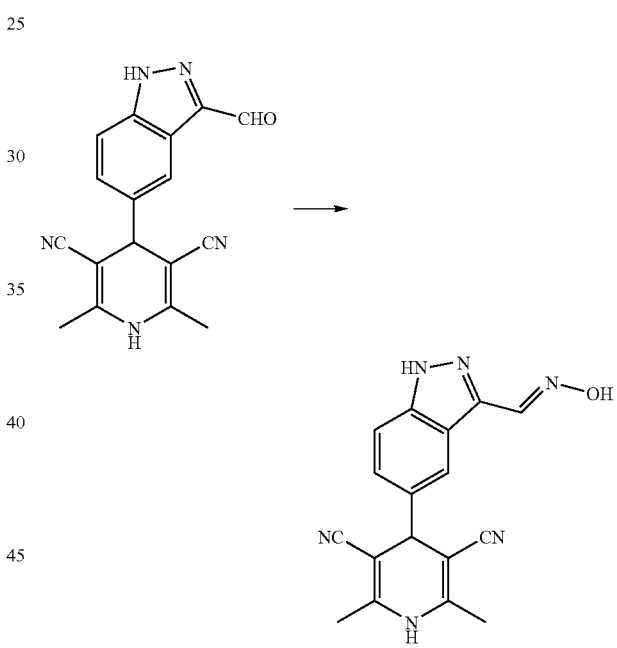

A mixture of NH$_2$OH.HCl (229 mg, 3.3 mmol) and 4-(3-formyl-1H-indazol-5-yl)-1,4-dihydro-2,6-dimethyl-3,5-pyridinedicarbonitrile (200 mg, 0.66 mmol), from Synthetic Example 10B, in pyridine (5 mL) was stirred at rt overnight. After removal of pyridine under vacuum, the residue was treated with a saturated solution of NaHCO$_3$ and extracted with CH$_2$Cl$_2$. The organic phases were combined, washed with brine, and concentrated. The residue was purified by column to give 1,4-dihydro-4-[3-[(E)-(hydroxyimino)methyl]-1H-indazol-5-yl]-2,6-dimethyl-3,5-pyridinedicarbonitrile (143 mg, 68%) as a powder (Cpd. No. 149, Table 2). 1H-NMR (400 MHz, DMSO-D6): δ=11.42 (s, 1H), 9.55 (s, 1H), 8.36 (s, 1H), 7.85 (s, 1H), 7.60 (d, 1H), 7.38 (d, 1H), 4.58 (s, 1H), 2.03 (s, 6H) ppm.

Synthetic Example 12

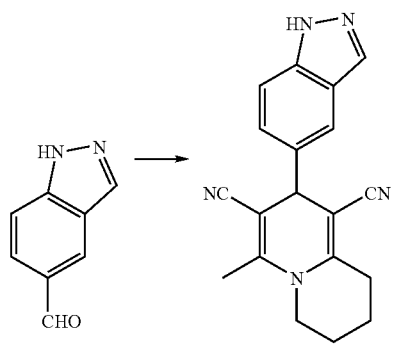

1H-indazole-5-carboxaldehyde (146 mg, 1 mmol), from Synthetic Preparation 1, and 2-piperidinylidene-ethanenitrile (122 mg, 1 mmol), from Synthetic Preparation 5, were mixed in 5 mL EtOH. The mixture was heated at 90° C. overnight. After removal of solvent in vacuo, the residue was dissolved in 5 mL acetic acid, and 3-aminocrotononitrile (82 mg, 1 mmol) was added. The mixture was heated at 115° C. for 10 min. After cooling, the acetic acid was removed in vacuo. The resulting residue was dissolved in 20 mL acetate, washed with 10 mL 1M $K_2CO_3$, dried, and concentrated in vacuo. The crude mixture was purified on flash column (silica gel) to afford a mixture (52 mg), which was further purified on HPLC. The fractions were collected and were neutralized with 2N $Na_2CO_3$ to pH 11.

This mixture was extracted with 40 mL ethyl acetate, dried, and concentrated. The product was re-dissolved in 2 mL $CH_3CN$ and 2 mL water, and dried under vacuum to afford 6,7,8,9-tetrahydro-2-(1H-indazol-5-yl)-4-methyl-2H-quinolizine-1,3-dicarbonitrile (40 mg, 13%) (Cpd. No. 304). 1H-NMR (400 MHz, DMSO-D6): δ=8.08 (s, 1H), 7.61 (s, 1H), 7.56 (d, 1H), 7.30 (d, 1H), 4.46 (s, 1H), 3.60 (d, 2H), 2.63 (m, 2H), 2.22 (s, 3H), 1.80 (m, 2H), 1.65 (m, 2H) ppm.

Synthetic Example 13

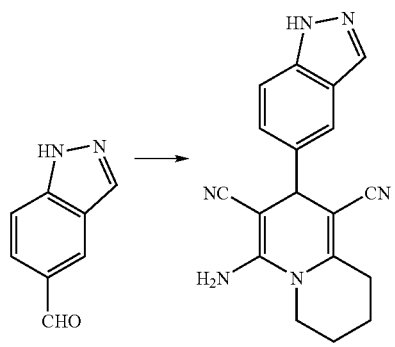

To a mixture of 1H-indazole-5-carboxaldehyde (200 mg, 1.37 mmol), from Synthetic Preparation 1, and malononitrile (100 mg, 1.51 mmol) in EtOH (5 mL) was added piperidine (0.2 mL). The mixture was stirred at rt for 2 hr, after which the solid (140 mg) was collected by filtration. This solid and 2-piperidinylidene-ethanenitrile (100 mg, 0.82 mmol; per Synthetic Preparation 5) were combined in EtOH (5 mL). The resulting mixture was kept at 90° C. for 1 hr. After cooling to rt, the solvent was removed in vacuo. The residue was purified on flash column (silica gel) and crystallized further in acetate to afford 4-amino-6,7,8,9-tetrahydro-2-(1H-indazol-5-yl)-2H-quinolizine-1,3-dicarbonitrile (110 mg, 25.4%) (Cpd. No. 305). 1H-NMR (400 MHz, CD3OD): δ=8.02 (s, 1H), 7.58 (s, 1H), 7.53 (d, 1H), 7.34 (d, 1H), 4.53 (s, 1H), 3.63 (d, 2H), 2.72 (m, 2H), 1.95 (m, 1H), 1.73-1.88 (m, 3H) ppm.

Synthetic Example 14

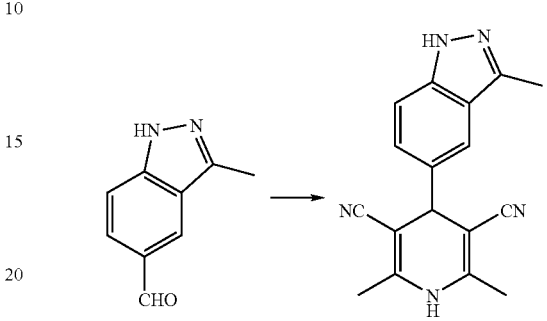

A mixture of 17.0 g (106.13 mmol) 3-methyl-1H-indazole-5-carbaldehyde, from Synthetic Preparation 10, and 17.86 g (217.57 mmol) 3-aminocrotononitrile were dissolved in 340 mL acetic acid and refluxed for 3 hours. After stirring overnight at room temperature the mixture was cooled with an ice bath, filtered and washed with a small amount of acetic acid. The product was dried under vacuum at 60° C. to afford 1,4-dihydro-2,6-dimethyl-4-(3-methyl-1H-indazol-5-yl)-3,5-pyridinedicarbonitrile (17.7 g, 57.6%) (Cpd. No. 81, Table 2). 1H-NMR (DMSO-D6): δ=12.68 (s, 1H), 9.51 (s, 1H), 7.53 (s, 1H), 7.49 (d, 1H), 7.27 (d, 1H), 4.50 (s, 1H), 2.49 (s, 3H), 2.05 (s, 6H) ppm. MS (ES+): 290.42 ($M^+$+1, 100%).

Synthetic Example 15

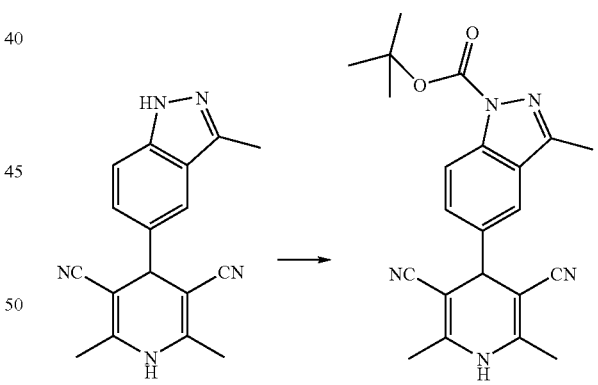

9.18 g (31.73 mmol) 2,6-dimethyl-4-(3-methyl-1H-indazol-5-yl)-1,4-dihydro-pyridine-3,5-dicarbonitrile, from Synthetic Example 14, were suspended in 289 mL tetrahydrofuran and 9.34 mL (67.4 mmol) triethylamine, 775.22 mg (6.35 mmol) 4-dimethylaminopyridine and 7.62 g (34.9 mmol) di-tert-butyl dicarbonate were added. The mixture was stirred for 3 hours, diluted with DCM and washed successively with water and saturated sodium chloride solution. The organic phase was dried over magnesium sulfate and concentrated under vacuum to yield 5-(3,5-dicyano-2,6-dimethyl-1,4-dihydro-pyridin-4-yl)-3-methyl-indazole-1-carboxylic acid tert-butyl ester (15.39 g). 1H-NMR (DMSO-D6): δ=9.57 (s, 1H), 8.08 (d, 1H), 7.69 (s, 1H), 7.56 (d, 1H), 4.61 (s, 1H), 2.54 (s, 3H), 2.05 (s, 6H), 1.64 (s, 9H) ppm.

Synthetic Example 16

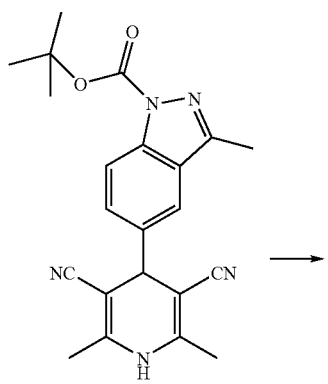

12.36 g (3173 mmol) 5-(3,5-dicyano-2,6-dimethyl-1,4-dihydro-pyridin-4-yl)-3-methyl-indazole-1-carboxylic acid tert-butyl ester, from Synthetic Example 15, were dissolved in 158 mL N,N-dimethylformamide. 1.62 g (40.61 mmol) sodium hydride (as a dispersion in mineral oil) were added and the mixture stirred for 20 minutes. 2.37 mL (38.08 mmol) methyl iodide were added and the mixture stirred for 2.5 hours. The solvent was distilled off under vacuum and the residue was taken up in ethyl acetate, washed with water and saturated sodium chloride solution and dried over sodium sulfate. Purification with column chromatography afforded 5-(3,5-dicyano-1,2,6-trimethyl-1,4-dihydro-pyridin-4-yl)-3-methyl-indazole-1-carboxylic acid tert-butyl ester (10.56 g, 82.5%). 1H-NMR (DMSO-D6): δ=8.06 (d, 1H), 7.67 (s, 1H), 7.56 (d, 1H), 4.56 (s, 1H), 3.22 (s, 3H), 2.54 (s, 3H), 2.25 (s, 6H), 1.64 (s, 9H) ppm. MS (ES+): 404.45 ($M^+$+1, 75%).

Synthetic Example 17

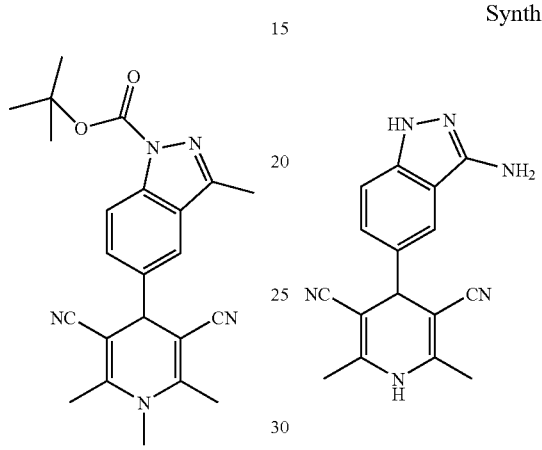

10.56 g (26.17 mmol) 5-(3,5-dicyano-1,2,6-trimethyl-1,4-dihydro-pyridin-4-yl)-3-methyl-indazole-1-carboxylic acid tert-butyl ester, from Synthetic Example 16, were dissolved in 70 mL dioxane. 350 mL of a 4 M solution of hydrochloric acid in dioxane was added. The mixture was stirred for 2 hours and then concentrated under vacuum. The residue was dissolved in ethyl acetate, washed with saturated sodium hydrogen carbonate solution and dried over magnesium sulfate. Purification with column chromatography gave 1,4-dihydro-1,2,6-trimethyl-4-(3-methyl-1H-indazol-5-yl)-3,5-pyridinedicarbonitrile (5.46 g, 68.8%). (Cpd. No. 306, Table 7). 1H-NMR (DMSO-D6): δ=12.67 (br s, 1H), 7.50 (s, 1H), 7.48 (d, 1H), 7.26 (d, 1H), 4.44 (s, 1H), 3.21 (s, 3H), 2.48 (s, 3H), 2.24 (s, 6H) ppm. MS (ES+): 304.45 ($M^+$+1, 100%).

Synthetic Example 18

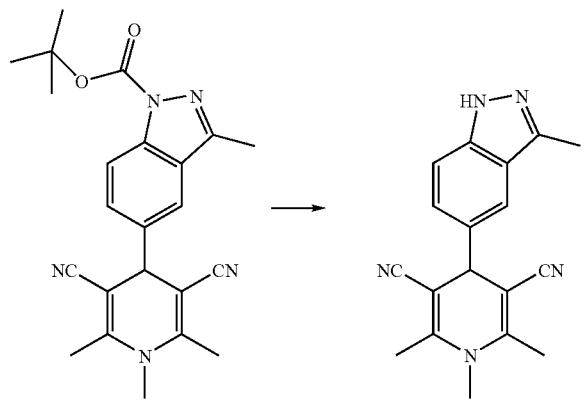

A mixture of 15.00 g (51.67 mmol) 4-(3-amino-1H-indazol-5-yl)-1,4-dihydro-2,6-dimethyl-3,5-pyridinedicarbonitrile, from Synthetic Example 2, 11.24 mL triethylamine (81.11 mmol), 1.51 g 4-dimethylaminopyridine (12.4 mmol) and 16.91 g di-tert-butyldicarbonate (77.5 mmol) in 756 mL dry tetrahydrofuran was stirred overnight at room temperature. The reaction mixture was partitioned between EtOAc and water and the extracted organic phase washed with saturated aqueous sodium chloride solution, concentrated to about 100 mL rest volume and cooled with stirring in an ice bath. The resulting suspension was filtered and the crude product washed with a small amount of cold EtOAc. The product was dried under vacuum to afford 3-amino-5-(3,5-dicyano-1,4-dihydro-2,6-dimethyl-4-pyridinyl)-1H-indazole-1-carboxylic acid tert-butyl ester (13.26 g, 65.7%) (Cpd. No. 92, Table 2). 1H-NMR (DMSO-D6, 300 MHz): δ=9.53 (br s, 1H), 7.91 (d, 1H), 7.71 (m, 1H), 7.41 (dd, 1H), 6.34 (br s, 2H), 4.47 (s, 1H), 2.02 (s, 6H), 1.55 (s, 9H) ppm.

Synthetic Example 19

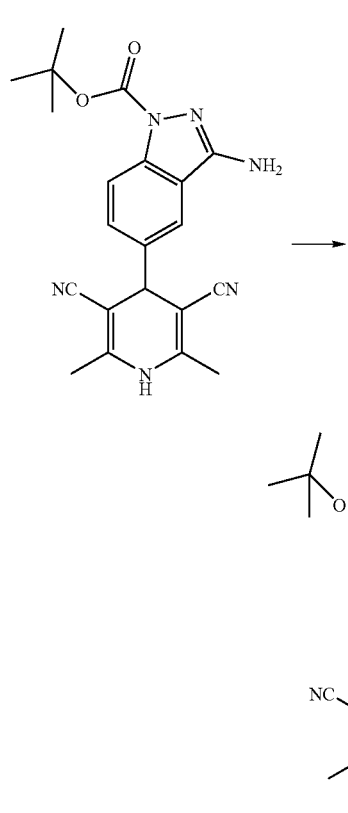

To a stirred mixture of 13.40 g (25.74 mmol) 3-amino-5-(3,5-dicyano-1,4-dihydro-2,6-dimethyl-4-pyridinyl)-1H-indazole-1-carboxylic acid tert-butyl ester, from Synthetic Example 18, in 335 mL dry methanol, was added 2.19 mL acetaldehyde and 2.06 mL glacial acetic acid and the resulting mixture was stirred overnight at room temperature. The reaction was cooled (ice bath) before 3.24 g sodium cyanoborohydride was added in three portions. The mixture was stirred overnight at room temperature before the reaction was concentrated to roughly half volume under vacuum. The residue was partitioned between EtOAc and saturated aqueous sodium hydrogen carbonate solution and the organic extract washed with saturated aqueous sodium chloride solution and concentrated under vacuum. The residue was taken up in hot EtOAc and allowed to cool to room temperature before being triturated with diisopropyl ether. The stirred suspension was cooled (ice bath), filtered and the crude product washed with diisopropyl ether. The product was dried under vacuum to afford 5-(3,5-dicyano-1,4-dihydro-2,6-dimethyl-4-pyridinyl)-3-(ethylamino)-1H-indazole-1-carboxylic acid tert-butyl ester (8.25 g, 76.6%) (Cpd. No. 117, Table 2). 1H-NMR (DMSO-D6, 300 MHz): δ=9.54 (br s, 1H), 7.86 (d, 1H), 7.73 (m, 1H), 7.41 (dd, 1H), 6.82 (t, 1H), 4.47 (s, 1H), 3.26-3.34 (partially obscured by solvent, m, 2H), 2.02 (s, 6H), 1.57 (s, 9H), 1.21 (t, 3H) ppm.

Synthetic Example 20

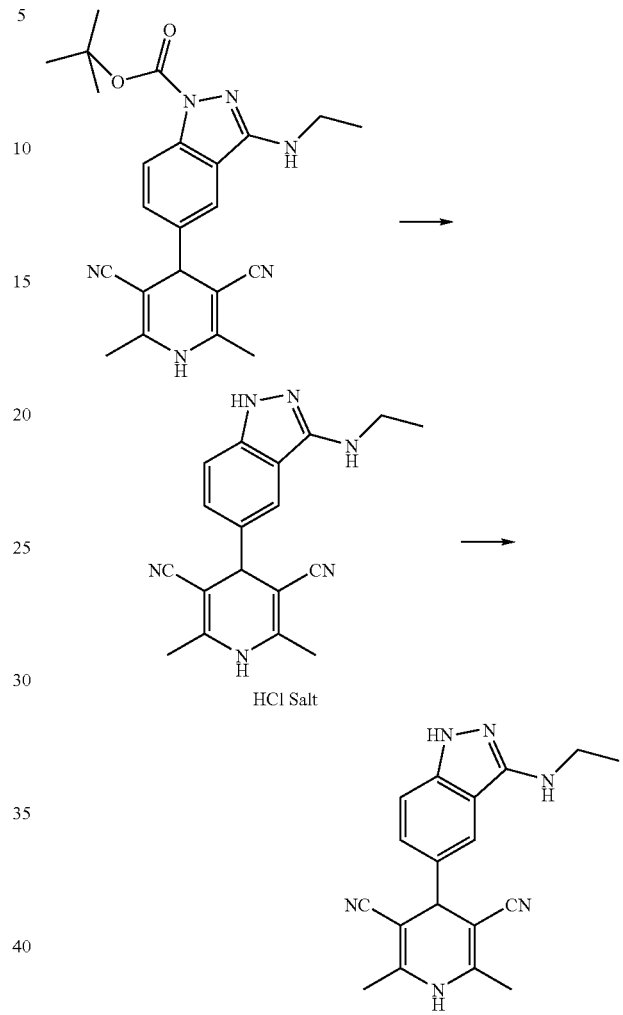

8.2 g (19.59 mmol) 5-(3,5-dicyano-1,4-dihydro-2,6-dimethyl-4-pyridinyl)-3-(ethylamino)-1H-indazole-1-carboxylic acid tert-butyl ester, from Synthetic Example 19, was stirred in 147 mL of a 4 M solution of HCl in dioxane, at 55° C. (bath temperature) for 2 hours. On cooling, the volatiles were removed under vacuum to furnish 4-[3-(ethylamino)-1H-indazol-5-yl]-1,4-dihydro-2,6-dimethyl-3,5-pyridinedicarbonitrile, hydrochloride salt (Cpd. No. 161, Table 2). The hydrochloride salt was converted to the free base as follows: the hydrochloride salt was suspended in a mixture of EtOAc and 2 M aqueous sodium hydroxide and heated on a steam bath until the solid completely dissolved. On cooling, the mixture was extracted and the organic phase was washed successively with saturated aqueous sodium chloride solution, dried over magnesium sulfate and concentrated under vacuum. The resulting crude product was purified by extracting twice with hot EtOAc (each time stirred in hot EtOAc, allowed to cool and filtered). The product was dried under vacuum to afford 4-[3-(ethylamino)-1H-indazol-5-yl]-1,4-dihydro-2,6-dimethyl-3,5-pyridinedicarbonitrile (4.6 g, 73.7%) (Cpd. No. 121, Table 2). 1H-NMR (DMSO-D6, 400 MHz): δ=11.38 (br s, 1H), 9.44 (br s, 1H), 7.51 (m, 1H), 7.20

(d, 1H), 7.12 (dd, 1H), 5.91 (t, 1H), 4.34 (s, 1H), 3.21-3.27 (m, 2H), 2.01 (s, 6H), 1.19 (t, 3H) ppm. m.p.=247.6° C.

Synthetic Example 21

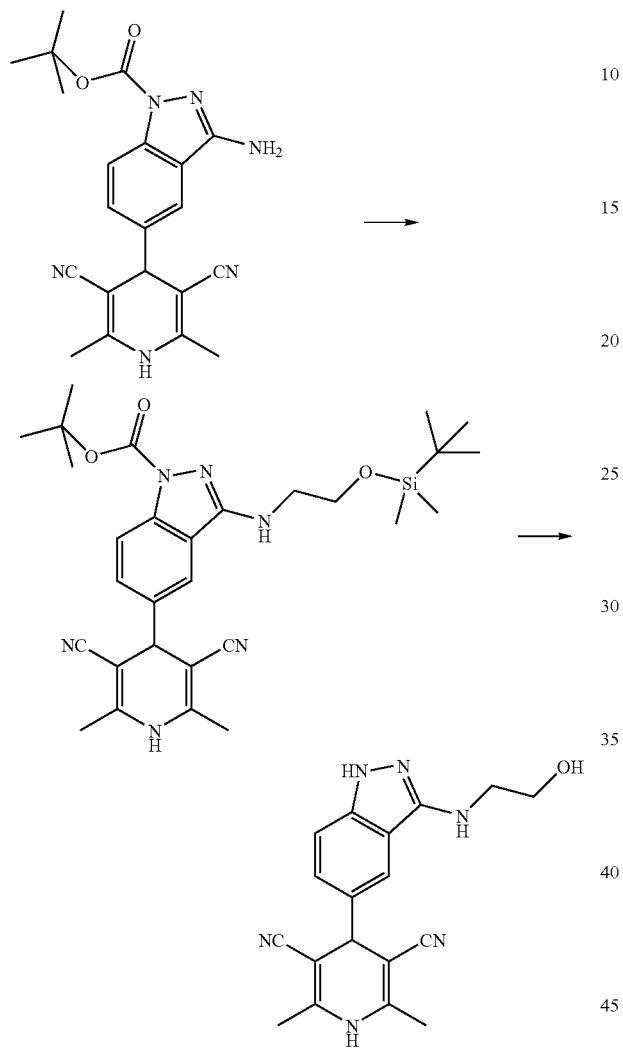

A: 3-Amino-5-(3,5-dicyano-1,4-dihydro-2,6-dimethyl-4-pyridinyl)-1H-indazole-1-carboxylic acid tert-butyl ester (16.1 g, 41.23 mmol), from Synthetic Example 18, was reacted with (tert-butyl-dimethyl-silanyloxy)-acetaldehyde (CAS 102191-92-4, obtained from Aldrich, 10.06 g, 58 mmol), according to the procedure detailed in Synthetic Example 19. The crude 3-[2-(tert-butyl-dimethyl-silanyloxy)-ethylamino]-5-(3,5-dicyano-2,6-dimethyl-1,4-dihydro-pyridin-4-yl)-indazole-1-carboxylic acid tert-butyl ester thus obtained was used without further purification in the next step.

B: A mixture of crude 3-[2-(tert-butyl-dimethyl-silanyloxy)-ethylamino]-5-(3,5-dicyano-2,6-dimethyl-1,4-dihydro-pyridin-4-yl)-indazole-1-carboxylic acid tert-butyl ester (165 mg) and HCl (4M solution in THF, 2 mL) was stirred overnight at room temperature. The mixture was partitioned between dilute aqueous sodium hydrogen carbonate solution (0.5%, 40 mL) and EtOAc (40 mL). The organic extract was dried (Na$_2$SO$_4$), concentrated and the residue purified by chromatography on silica gel to give 1,4-dihydro-4-[3-[(2-hydroxyethyl)amino]-1H-indazol-5-yl]-2,6-dimethyl-3,5-pyridinedicarbonitrile (66 mg) (Cpd. No. 118, Table 2).

Synthetic Example 22

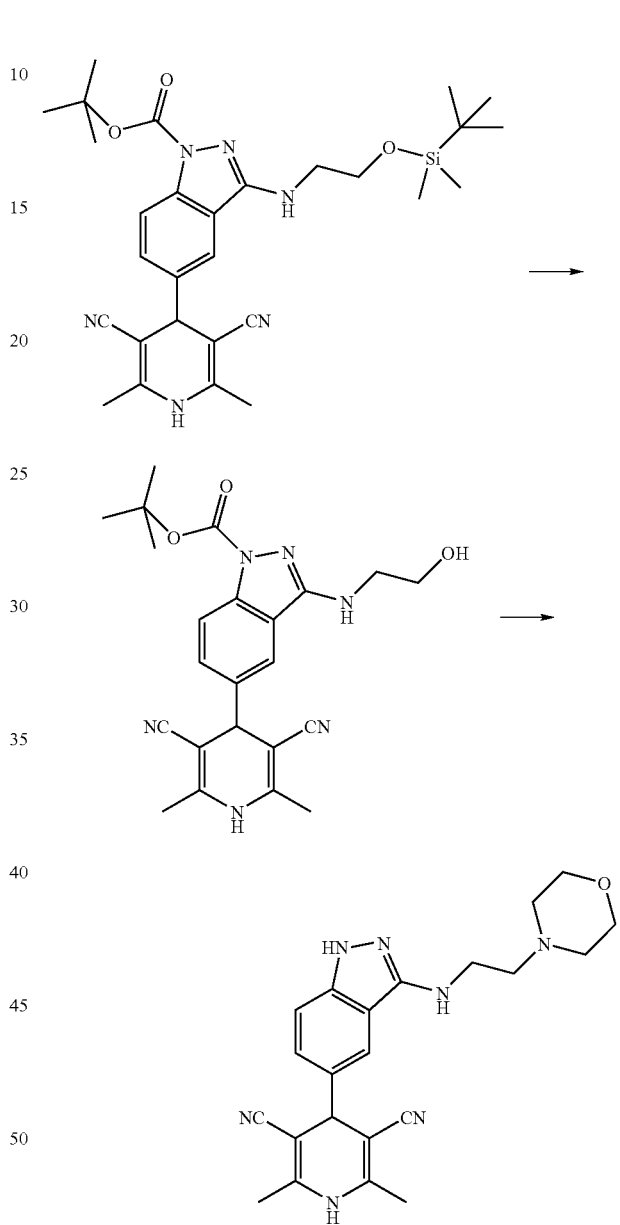

A: Crude 3-[2-(tert-butyl-dimethyl-silanyloxy)-ethylamino]-5-(3,5-dicyano-2,6-dimethyl-1,4-dihydro-pyridin-4-yl)-indazole-1-carboxylic acid tert-butyl ester (6.58 g), from Synthetic Example 21, was dissolved in THF (350 mL), under Argon, and a solution of TBAF in THF (1M, 28.5 mL) was added. The mixture was stirred overnight at room temperature. The mixture was quenched with saturated ammonium chloride solution, diluted with water and extracted with EtOAc. The combined organic extracts were washed with brine, dried and concentrated to give crude 5-(3,5-dicyano-2,6-dimethyl-1,4-dihydro-pyridin-4-yl)-3-(2-hydroxy-ethylamino)-indazole-1-carboxylic acid tert-butyl ester which was used in the next step without further purification.

B: To a stirred and chilled (ice/water bath) solution of crude 5-(3,5-dicyano-2,6-dimethyl-1,4-dihydro-pyridin-4-yl)-3-(2-hydroxy-ethylamino)-indazole-1-carboxylic acid tert-butyl ester (1 g) in THF (157 mL), under argon, was added sequentially 4-methylmorpholine (5.2 mL) and mesyl chloride (MsCl, CH₃SO₂Cl, 0.89 mL) dropwise. The mixture was allowed to warm to room temperature overnight before morpholine (41 mL) was added. Stirring was continued overnight before heating to 35° C. On cooling, triethylamine was added, the mixture concentrated to ca. one third the volume and the residue cooled (ice/water bath). The mixture was quenched with ice and aqueous sodium carbonate solution and the extracted with EtOAc. The combined organic extracts were dried and concentrated. The residue was taken up in THF (15 mL), HCl (15 mL) was added and the mixture was heated for 1.5 h at 60° C. (bath temperature). On cooling, the mixture was poured carefully onto aqueous sodium hydrogencarbonate solution and extracted with EtOAc. The combined organic extracts were dried and concentrated. The residue was purified by preparative reverse phase HPLC to give 1,4-dihydro-2,6-dimethyl-4-[3-[[2-(4-morpholinyl)ethyl]amino]-1H-indazol-5-yl]-3,5-pyridinedicarbonitrile (60 mg) (Cpd. No. 307, Table 8). 1H-NMR (DMSO-D6, 300 MHz): δ=11.46 (br s, 1H), 9.50 (br s, 1H), 7.56 (s, 1H), 7.25 (d, 1H), 7.17 (dd, 1H), 5.93 (t, 1H), 4.40 (s, 1H), 3.60 (m, 4H), 3.40 (partially obscured by solvent, 2H), 2.59 (t, 2H), 2.44 (m, 4H), 2.05 (s, 6H) ppm.

Synthetic Example 23

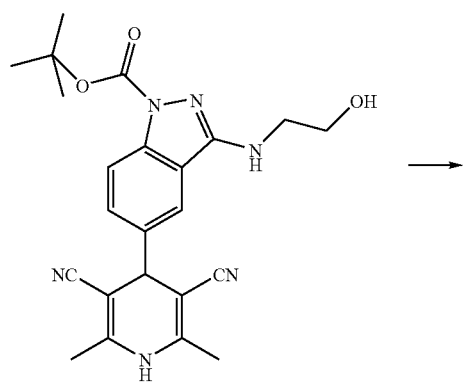

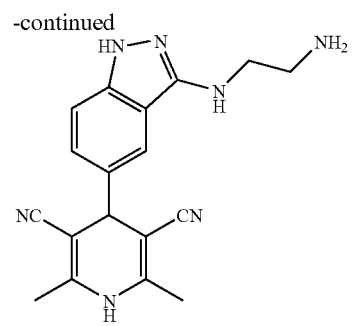

A: To a stirred solution of crude 5-(3,5-dicyano-2,6-dimethyl-1,4-dihydro-pyridin-4-yl)-3-(2-hydroxy-ethylamino)-indazole-1-carboxylic acid tert-butyl ester (0.6 g), from Synthetic Example 22, in THF (14.3 mL), under Argon, was added sequentially triphenylphosphine (1.08 g, 4.13 mmol), phthalamide (0.21 g, 1.45 mmol), followed by diisopropyl azadicarboxylate (DIAD, 0.31 g, 1.52 mmol) dropwise over 30 minutes. The mixture was stirred overnight at room temperature. The mixture was quenched with saturated sodium hydrogencarbonate solution and extracted with EtOAc. The combined organic extracts were washed with brine, dried and concentrated. The residue was partially purified by chromatography on silica gel, followed by preparative reverse phase HPLC to give 5-(3,5-dicyano-2,6-dimethyl-1,4-dihydro-pyridin-4-yl)-3-[2-(1,3-dioxo-1,3-dihydro-isoindol-2-yl)-ethylamino]-indazole-1-carboxylic acid tert-butyl ester (131 mg) which was used directly in the next step.

B: A mixture of crude 5-(3,5-dicyano-2,6-dimethyl-1,4-dihydro-pyridin-4-yl)-3-[2-(1,3-dioxo-1,3-dihydro-isoindol-2-yl)-ethylamino]-indazole-1-carboxylic acid tert-butyl ester (110 mg), hydrazine hydrate (80%, 0.039 mL, 0.62 mmol) and ethanol (1 mL), was heated at reflux for 2 hours. On cooling the reaction mixture was concentrated and the residue taken up in THF and aqueous HCl (4M) and heated at reflux for 1 hour. On cooling the reaction mixture was concentrated and the residue purified by preparative reverse phase HPLC to give 4-[3-[(2-aminoethyl)amino]-1H-indazol-5-yl]-1,4-dihydro-2,6-dimethyl-3,5-pyridinedicarbonitrile (38 mg) (Cpd. No. 308, Table 8). 1H-NMR (DMSO-D6, 300 MHz): δ=11.38 (br s, 1H), 9.46 (br s, 1H), 7.52 (s, 1H), 7.20 (d, 1H), 7.12 (dd, 1H), 5.93 (t, 1H), 4.34 (s, 1H), 3.21 (m, 2H), 2.75 (t, 2H), 2.01 (s, 6H) ppm.

Synthetic Example 24

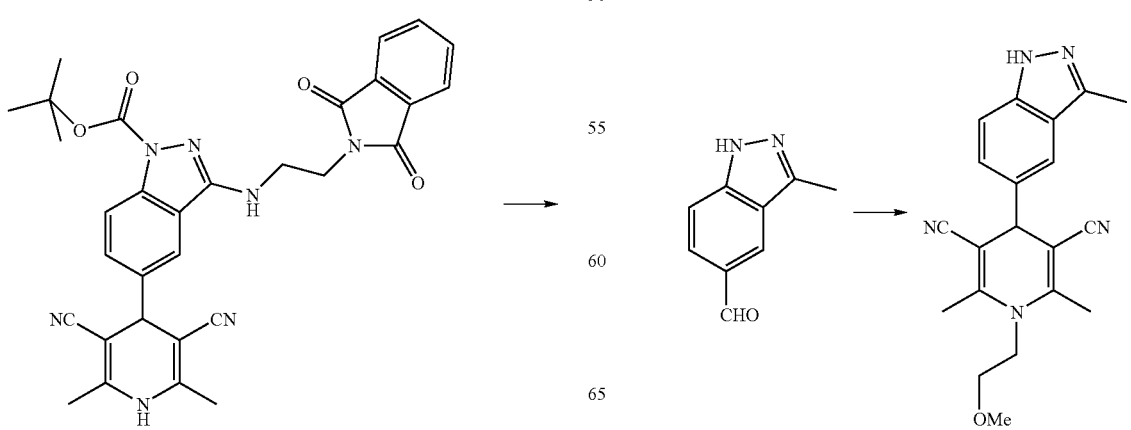

164.2 mg (2 mmols) 3-aminocrotononitrile and 150.2 mg (2 mmols) 2-methoxyethylamine were dissolved in 8 mL ethanol and refluxed under argon for 3 hours. The solvent was distilled off under vacuum and the residue dissolved in 10 mL acetic acid. 160.2 mg (1 mmol) 3-methyl-1H-indazole-5-carbaldehyde (from Synthetic Preparation 10) were added. The mixture was stirred for 3 hours at 100° C. and then concentrated under vacuum. Purification by column chromatography gave 1-(2-methoxy-ethyl)-2,6-dimethyl-4-(3-methyl-1H-indazol-5-yl)-1,4-dihydro-pyridine-3,5-dicarbonitrile (22 mg) (Cpd. No. 310). 1H-NMR (DMSO-d6): δ=12.68 (br s, 1H), 7.51 (s, 1H), 7.47 (d, 1H), 7.26 (d, 1H), 4.40 (s, 1H), 3.86 (t, 2H), 3.52 (t, 2H), 3.37 (s, 3H), 2.50 (s, 3H; covered by DMSO), 2.25 (s, 6H) ppm.

Synthetic Example 25

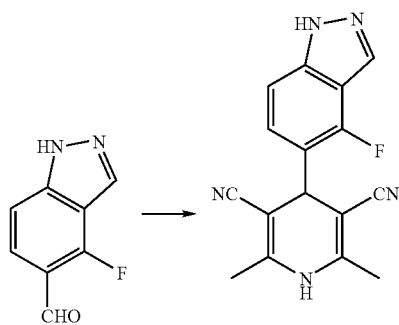

250 mg (1.52 mmols) 4-fluoro-1H-indazole-5-carbaldehyde (Synthetic Preparation 11) and 250.1 mg (3.05 mmols) 3-aminocrotononitrile were dissolved in 1.74 mL acetic acid and refluxed for 1.5 hours. The mixture was allowed to cool to room temperature, filtered and washed with a little amount of acetic acid. The product was dried under vacuum at 40° C. to yield a first crop. The mother liquors were diluted with ethyl acetate, washed with water and saturated sodium hydrogen carbonate solution and dried over sodium sulfate to yield a second crop. Together 232 mg (51, 9%) 4-(4-fluoro-1H-indazol-5-yl)-2,6-dimethyl-1,4-dihydro-pyridine-3,5-dicarbonitrile were obtained (Cpd. No. 311). 1H-NMR (DMSO-d6): δ=13.42 (br s, 1H), 9.58 (br s, 1H), 8.21 (s, 1H), 7.44 (d, 1H), 7.32 (dd, 1H), 4.86 (s, 1H), 2.04 (s, 6H) ppm.

Synthetic Example 26

Further Compounds of Formula I

Following the general procedures described herein and exemplified in Synthetic Examples 1-25, compounds of Formula I in Tables 1-8, as well as other compounds encompassed within Formula I can be synthesized utilizing the appropriate starting materials.

TABLE 1

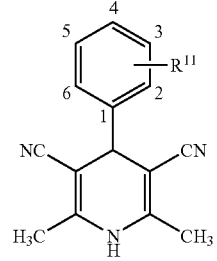

| Cpd No. | $R^{11}$ | 1H NMR | Name |
|---|---|---|---|
| 4 | 4, —OH and 3, —Cl | (DMSO-D6, 400 MHz): δ = 9.4 (s, 1H), 8.92 (s, 1H), 6.75 (m, 2H), 6.58 (m, 1H), 4.2 (s, 1H), 3.98 (q, 2H), 2.0 (s, 6H), 1.3 (t, 3H) ppm | 4-(3-chloro-4-hydroxyphenyl)-1,4-dihydro-2,6-dimethyl-3,5-pyridinedicarbonitrile |
| 5 | 4, —OH and 3, —Br | (DMSO-D6, 400 MHz): δ = 10.33 (s, 1H), 9.50 (s, 1H), 7.34 (s, 1H), 7.08 (d, 1H), 6.96 (d, 1H), 4.34 (s, 1H), 2.03 (s, 6H) ppm | 4-(3-bromo-4-hydroxyphenyl)-1,4-dihydro-2,6-dimethyl-3,5-pyridinedicarbonitrile |
| 6 | 4, —OH and 3, —CH₃ | (DMSO-D6, 400 MHz): δ = 9.40 (s, 1H), 9.33 (s, 1H), 6.92 (s, 1H), 6.85 (d, 1H), 6.75 (d, 1H), 4.20 (s, 1H), 2.11 (s, 3H), 2.02 (s, 6H) ppm | 1,4-dihydro-4-(4-hydroxy-3-methylphenyl)-2,6-dimethyl-3,5-pyridinedicarbonitrile |
| 7 | 4, —OH and 3, —F | (DMSO-D6, 400 MHz): δ = 9.89 (s, 1H), 9.47 (s, 1H), 7.00 (dd, 1H), 6.93 (t, 1H), 6.86 (dd, 1H), 4.29 (s, 1H), 2.00 (s, 6H) ppm | 4-(3-fluoro-4-hydroxyphenyl)-1,4-dihydro-2,6-dimethyl-3,5-pyridinedicarbonitrile |
| 8 | 4, —OH and 3, —CO₂CH₃ | (DMSO-D6, 400 MHz): δ = 7.64 (s, 1H), 7.44 (d, 1H), 7.04 (d, 1H), 4.46 (s, 1H), 3.90 (s, 3H), 3.17 (s, 1H), 2.03 (s, 6H) ppm | 5-(3,5-dicyano-1,4-dihydro-2,6-dimethyl-4-pyridinyl)-2-hydroxy-benzoic acid, methyl ester |

TABLE 1-continued

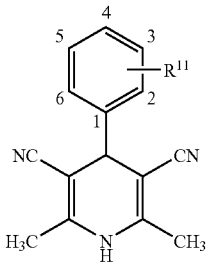

| Cpd No. | R¹¹ | 1H NMR | Name |
|---|---|---|---|
| 9 | 4, —OH and 3, —I | (DMSO-D6, 400 MHz): δ = 10.39 (s, 1H), 9.48 (s, 1H), 7.52 (s, 1H), 7.09 (d, 1H), 6.89 (d, 1H), 4.32 (s, 1H), 2.03 (s, 6H) ppm | 1,4-dihydro-4-(4-hydroxy-3-iodophenyl)-2,6-dimethyl-3,5-pyridinedicarbonitrile |
| 10 | 3, —CO₂CH₃ | (DMSO-D6, 400 MHz): δ = 2.10 (s, 6H), 3.85 (s, 3H), 4.60 (s, 1H), 7.60 (m, 2H), 7.90 (s, 1H), 7.95 (d, 1H), 9.60 (s 1H) ppm | 3-(3,5-dicyano-1,4-dihydro-2,6-dimethyl-4-pyridinyl)-benzoic acid, methyl ester |
| 11 | 3, —Br | δ = 2.06 (s, 6H), 4.44 (s, 1H), 7.21 (t, 1H), 7.19-7.32 (dt, 1H), 7.61 (t, 1H), 7.66-7.69 (dt, 1H), 9.55 (s, 1H) ppm | 4-(3-bromophenyl)-1,4-dihydro-2,6-dimethyl-3,5-pyridinedicarbonitrile |
| 12 | 3, —C(O)NHCH₃ TFA salt | (DMSO-D6, 400 MHz): δ = 2.00 (s, 6H), 2.78 (d, 3H), 4.47 (s, 1H), 7.42 (d, 1H), 7.48 (dd, 1H), 7.72 (s, 1H), 7.77 (d, 1H), 8.52 (q, 1H), 9.60 (s, 1H) ppm | (AutoNom 2000 name) 3-(3,5-dicyano-2,6-dimethyl-1,4-dihydro-pyridin-4-yl)-N-methyl-benzamide, TFA salt |
| 13 | 3, 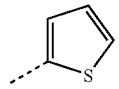 | (DMSO-D6, 400 MHz): δ = 2.2 (s, 6H), 4.45 (s, 1H), 7.14 (dd, 1H), 7.22 (d, 1H), 4.44 (dd, 1H), 7.50 (m, 2H), 7.56 (dd, 1H), 7.59 (d, 1H), 9.60 (s 1H) ppm. | 1,4-dihydro-2,6-dimethyl-4-[3-(2-thienyl)phenyl]-3,5-pyridinedicarbonitrile |
| 14 | 3, 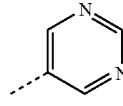 | (DMSO-D6, 400 MHz): δ = 2.02 (s, 6H), 4.50 (s, 1H), 7.38 (d, 1H), 7.55 (m, 1H), 7.67 (s, 1H), 7.75 (d, 1H), 9.10 (s, 2H), 9.20 (s, 1H), 9.55 (s, 1H). | 1,4-dihydro-2,6-dimethyl-4-[3-(5-pyrimidinyl)phenyl]-3,5-pyridinedicarbonitrile |
| 16 | 3, —I | δ = 2.03 (s, 6H), 4.44 (s, 1H), 7.21 (t, 1H), 7.19-7.32 (dt, 1H), 7.61 (t, 1H), 7.66-7.69 (dt, 1H), 9.55 (s, 1H) ppm | 1,4-dihydro-4-(3-iodophenyl)-2,6-dimethyl-3,5-pyridinedicarbonitrile |
| 17 | 3, —C(O)NH₂ | (DMSO-D6, 400 MHz): δ = 2.2 (s, 6H), 4.40 (s, 1H), 7.40 (m, 3H), 7.74 (s, 1H), 7.80 (d, 1H), 9.55 (s 1H) ppm | 3-(3,5-dicyano-1,4-dihydro-2,6-dimethyl-4-pyridinyl)-benzamide |
| 18 | 3,  | (DMSO-D6, 400 MHz): δ = 9.58 (s, 1H), 7.91 (m, 1H), 7.80 (m, 1H), 7.58 (m, 2H), 4.57 (s, 1H), 2.59 (s, 3H), 2.05 (s, 6H) ppm | 4-(3-acetylphenyl)-1,4-dihydro-2,6-dimethyl-3,5-pyridinedicarbonitrile |
| 19 | 3, 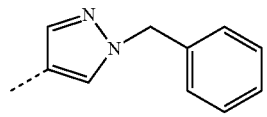 | (DMSO-D6, 400 MHz): δ = 2.04 (s, 6H), 4.40 (s, 1H), 5.34 (s, 2H), 7.08-7.11 (d, 1H), 7.24-7.30 (m, 3H), 7.32-7.35 (m, 2H), 7.36-7.42 (m, 2H), 7.50-7.53 (dt, 1H), 7.91 (s, 1H), 8.30 (s, 1H), 9.50 (s, 1H) ppm | 1,4-dihydro-2,6-dimethyl-4-[3-[1-(phenylmethyl)-1H-pyrazol-4-yl]phenyl]-3,5-pyridinedicarbonitrile |

TABLE 1-continued

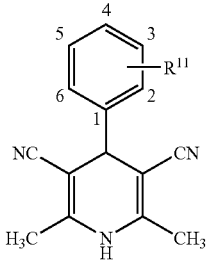

| Cpd No. | R[11] | 1H NMR | Name |
|---|---|---|---|
| 20 | 3, —C(O)NHOH | (DMSO-D6, 400 MHz): δ = 11.27 (s, 1H), 9.54 (s, 1H), 7.63 (m, 2H), 7.41 (m, 2H), 4.47 (s, 1H), 2.02 (s, 6H) ppm | 3-(3,5-dicyano-1,4-dihydro-2,6-dimethyl-4-pyridinyl)-N-hydroxy-benzamide |
| 21 | 3, —C(O)NHPy | (DMSO-D6, 400 MHz): δ = 2.10 (s, 6H), 3.85 (s, 3H), 4.60 (s, 1H), 7.60 (m, 2H), 7.90 (s, 1H), 7.95 (d, 1H), 9.60 (s 1H) ppm. | 3-(3,5-dicyano-1,4-dihydro-2,6-dimethyl-4-pyridinyl)-N-3-pyridinyl-benzamide |
| 22 | 3, —C(O)NHCH$_3$ | (DMSO-D6, 400 MHz): δ = 2.00 (s, 6H), 2.78 (d, 3H), 4.47 (s, 1H), 7.42 (d, 1H), 7.48 (dd, 1H), 7.72 (s, 1H), 7.77 (d, 1H), 8.52 (q, 1H), 9.60 (s, 1H) ppm | 3-(3,5-dicyano-1,4-dihydro-2,6-dimethyl-4-pyridinyl)-N-methyl-benzamide |
| 23 | 3, —C(O)NH(CH$_2$)$_2$Py | (DMSO-D6, 400 MHz): δ = 1.00 (m, 2H), 1.40 (m, 3H), 1.60 (m, 2H), 2.03 (s, 6H), 2.40 (t, 2H), 2.88 (d, 2H), 3.25 (m, 2H), 4.43 (s, 1H), 7.40 (m, 1H), 7.45 (dd, 1H), 7.70 (s, 1H), 7.75 (d, 1H), 8.45 (t, 1H) ppm | 3-(3,5-dicyano-1,4-dihydro-2,6-dimethyl-4-pyridinyl)-N-[2-(4-pyridinyl)ethyl]-benzamide |
| 24 | 3, 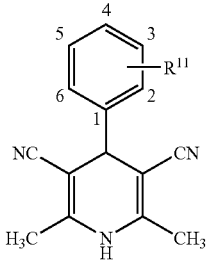 | (DMSO-D6, 400 MHz): δ = 2.02 (s, 6H), 2.18 (s, 6H), 2.40 (m, 2H), 3.35 (m, 2H), 4.48 (s, 1H), 5.75 (s, 1H), 7.40 (m, 1H), 7.48 (m, 1H), 7.70 (s, 1H), 7.75 (m, 1H), 8.43 (t, 1H), 9.54 (s, 1H) ppm | 3-(3,5-dicyano-1,4-dihydro-2,6-dimethyl-4-pyridinyl)-N-[2-(dimethylamino)ethyl]-benzamide |
| 25 | 3, 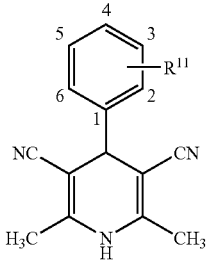 | (DMSO-D6, 400 MHz): δ = 0.98 (m, 2H), 1.34 (s, 9H), 1.44 (m, 4H), 1.64 (m, 2H), 2.02 (s, 6H), 2.64 (m, 2H), 3.88 (m, 2H), 4.48 (s, 1H), 7.40 (m, 1H), 7.45 (m, 1H), 7.70 (s, 1H), 7.75 (m, 1H), 8.43 (t, 1H), 9.54 (s, 1H) ppm | 4-[2-[[3-(3,5-dicyano-1,4-dihydro-2,6-dimethyl-4-pyridinyl)benzoyl]amino]ethyl]-piperidinecarboxylic acid, 1,1-dimethylethyl ester |
| 26 | 3, 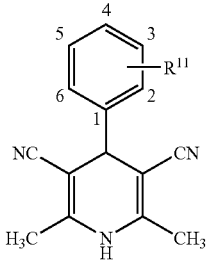 | (DMSO-D6, 400 MHz): δ = 1.00 (m, 2H), 1.40 (m, 3H), 1.60 (m, 2H), 2.03 (s, 6H), 2.40 (t, 2H), 2.88 (d, 2H), 3.25 (m, 2H), 4.43 (s, 1H), 7.40 (m, 1H), 7.45 (dd, 1H), 7.70 (s, 1H), 7.75 (d, 1H), 8.45 (t, 1H) ppm | 3-(3,5-dicyano-1,4-dihydro-2,6-dimethyl-4-pyridinyl)-N-[2-(4-piperidinyl)ethyl]-benzamide |
| 27 | 3, —NH(CO)CH$_3$ | (DMSO-D6, 400 MHz): δ = 2.00 (s, 9H), 4.31 (s, 1H), 6.90 (d, 1H), 7.26 (dd, 1H), 7.40 (s, 1H), 7.58 (d, 1H), 9.48 (s, 1H), 9.95 (s, 1H) ppm | N-[3-(3,5-dicyano-1,4-dihydro-2,6-dimethyl-4-pyridinyl)phenyl]-acetamide |
| 28 | 3, —NH(CO)NHCH$_3$ | (DMSO-D6, 400 MHz): δ = 2.00 (s, 6H), 2.60 (d, 3), 4.27 (s, 1H), 5.94 (m, 1H), 6.75 (d, 2H), 7.20 (dd, 1H), | N-[3-(3,5-dicyano-1,4-dihydro-2,6-dimethyl-4-pyridinyl)phenyl]-N'-methyl-urea |

TABLE 1-continued

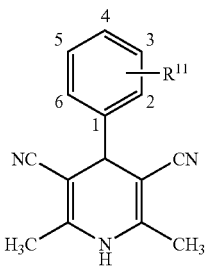

| Cpd No. | R11 | 1H NMR | Name |
|---|---|---|---|
| | | 7.22 (s, 1H), 7.34 (d, 1H), 8.55 (s, 1H), 9.25 (s, 1H) ppm | |
| 29 | 3, ![acetone hydrazide] | (DMSO-D6, 400 MHz): δ = 10.49 (s, 1H), 9.60 (s, 1H), 7.77 (m, 1H), 7.69 (m, 1H), 7.48 (m, 2H), 4.52 (s, 1H), 2.08 (s, 6H), 2.00 (m, 6H) ppm | 3-(3,5-dicyano-1,4-dihydro-2,6-dimethyl-4-pyridinyl)-benzoic acid, 2-(1-methylethylidene)hydrazide |
| 30 | 3, ![hydrazide] | (DMSO-D6, 400 MHz): δ = 9.85 (s, 1H), 9.56 (s, 1H), 7.74 (m, 2H), 7.47 (m, 1H), 7.40 (m, 1H), 4.49 (m, 3H), 2.05 (s, 3H) ppm | 3-(3,5-dicyano-1,4-dihydro-2,6-dimethyl-4-pyridinyl)-benzoic acid, hydrazide |
| 31 | 3, NHSO2CH3 | (DMSO-D6, 400 MHz): δ = 2.00 (s, 6H), 2.89 (s, 3), 4.35 (s, 1H), 6.98 (d, 1H), 7.12 (m, 2H), 7.34 (dd, 1H), 9.50 (s, 1H), 9.80 (s, 1H) ppm | N-[3-(3,5-dicyano-1,4-dihydro-2,6-dimethyl-4-pyridinyl)phenyl]-methanesulfonamide |
| 32 | 3, ![imidazole propyl benzamide] | (DMSO-D6, 400 MHz): δ = 9.55 (s, 1H), 8.56 (t, 1H), 7.78 (d, 1H), 7.70 (s, 1H), 7.64 (s, 1H), 7.48 (t, 1H), 7.42 (d, 1H), 7.18 (s, 1H), 6.86 (s, 1H), 4.48 (s, 1H), 3.99 (t, 2H), 3.22 (m, 2H), 2.03 (s, 6H), 1.94 (t, 2H) ppm | 3-(3,5-dicyano-1,4-dihydro-2,6-dimethyl-4-pyridinyl)-N-[3-(1H-imidazol-1-yl)propyl]-benzamide |
| 33 | 3, ![bis urea structure] | (DMSO-D6, 400 MHz): δ = 2.02 (s, 6H), 4.30 (s, 2H), 6.82 (m, 2H), 7.25 (m, 4H), 7.41 (m, 2H), 8.75 (s, 2H), 9.50 (s, 2H) ppm | N,N'-bis[3-(3,5-dicyano-1,4-dihydro-2,6-dimethyl-4-pyridinyl)phenyl]-urea |
| 34 | 3, —NH(CO)OCH3 | (DMSO-D6, 400 MHz): δ = 2.02 (s, 6H), 3.62 (s, 3H), 4.30 (s, 1H), 6.85 (m, 1H), 7.25 (t, 1H), 7.40 (m, 2H), 9.50 (s, 1H), 9.68 (s, 1H) ppm | [3-(3,5-dicyano-1,4-dihydro-2,6-dimethyl-4-pyridinyl)phenyl]-carbamic acid, methyl ester |
| 35 | 3, ![N-benzyl piperidinyl benzamide] | (DMSO-D6, 400 MHz): δ = 1.55 (q, 2H), 1.75 (m, 2H), 2.02 (m, 8H), 2.80 (d, 2H), 3.45 (s, 2H), 3.75 (m, 1H), 4.48 (s, 1H), 7.22 (m, 1H), 7.30 (m, 4H), 7.40 (d, 2H), 7.45 (t, 1H), 7.68 (s, 1H), 7.75 (d, 1H), 8.28 (d, 1H), 9.54 (s, 1H) ppm | 3-(3,5-dicyano-1,4-dihydro-2,6-dimethyl-4-pyridinyl)-N-[1-(phenylmethyl)-4-piperidinyl]-benzamide |

TABLE 1-continued

| Cpd No. | R11 | 1H NMR | Name |
|---|---|---|---|
| 36 | 3, -C(O)NH-CH2CH2-C6H4-SO2NH2 (para) | (DMSO-D6, 400 MHz): δ = 2.02 (s, 6H), 2.80 (t, 2H), 3.45 (q, 2H), 4.48 (s, 1H), 7.22 (s, 2H) 7.42 (m, 4H), 7.70 (m, 4H), 8.64 (t, 1H), 9.54 (s, 1H) ppm | N-[2-[4-(aminosulfonyl)phenyl]ethyl]-3-(3,5-dicyano-1,4-dihydro-2,6-dimethyl-4-pyridinyl)-benzamide |
| 37 | 3, -C(O)NH-(CH2)3-CO2Et | (DMSO-D6, 400 MHz): δ = 1.04 (t, 3H), 1.75 (m, 2H), 2.02 (s, 6H), 2.40 (m, 2H), 3.40 (m, 2H), 4.10 (q, 2H), 4.48 (s, 1H), 7.40 (m, 1H), 7.45 (m, 1H), 7.70 (s, 1H), 7.75 (m, 1H), 8.43 (t, 1H), 9.54 (s, 1H) ppm | 4-[[3-(3,5-dicyano-1,4-dihydro-2,6-dimethyl-4-pyridinyl)benzoyl]amino]-butanoic acid, ethyl ester |
| 38 | 3, -NH-C(O)-(3-pyridyl) | (DMSO-D6, 400 MHz): δ = 2.00 (s, 6H), 4.40 (s, 1H), 7.00 (d, 1H), 7.35 (dd, 1H), 7.55 (dd, 1H), 7.68 (s, 1H), 7.75 (d, 1H), 8.26 (d, 1H), 8.74 (d, 1H), 9.08 (s, 1H), 9.52 (s, 1H), 10.47 (s, 1H) ppm | N-[3-(3,5-dicyano-1,4-dihydro-2,6-dimethyl-4-pyridinyl)phenyl]-3-pyridinecarboxamide |
| 39 | 3, -C(O)NH-CH2CH2-(1-methyl-2-pyrrolidinyl) | (400 MHz, CD3OD): δ = 7.75 (m, 2H), 7.46 (m, 2H), 4.43 (s, 1H), 3.42 (m, 1H), 3.14 (m, 2H), 2.43 (s, 3H), 2.38 (m, 2H), 2.2 (m, 2H), 1.81 (m, 2H), 1.63 (m, 2H) ppm | 3-(3,5-dicyano-1,4-dihydro-2,6-dimethyl-4-pyridinyl)-N-[2-(1-methyl-2-pyrrolidinyl)ethyl]-benzamide |
| 40 | 3, -C(O)NH-(CH2)3-(4-morpholinyl) | (400 MHz, CD3OD): δ = 7.76 (m, 2H0, 7.47 (m, 2H), 3.62 (m, 4H), 3.44 (m, 2H), 2.56 (m, 6H), 2.08 (s, 6H), 1.91 (m, 2H) ppm | 3-(3,5-dicyano-1,4-dihydro-2,6-dimethyl-4-pyridinyl)-N-[3-(4-morpholinyl)propyl]-benzamide |
| 41 | 3, -C(O)-[4-(1,3-benzodioxol-5-ylmethyl)-1-piperazinyl] | (DMSO-D6, 400 MHz): δ = 2.02 (s, 6H), 2.30-2.40 (m, 4H), 3.38 (s, 2H), 3.58 (m, 2H), 4.48 (s, 1H), 5.95 (s, 2H), 6.72 (d, 1H), 6.82 (m, 2H), 7.22 (s, 1H), 7.33 (d, 1H), 7.37 (d, 1H), 7.46 (t, 1H), 9.54 (s, 1H) ppm | 4-[3-[[4-(1,3-benzodioxol-5-ylmethyl)-1-piperazinyl]carbonyl]phenyl]-1,4-dihydro-2,6-dimethyl-3,5-pyridinedicarbonitrile |
| 42 | 3, -C(O)NH-(4-pyridyl) | (DMSO-D6, 400 MHz): δ = 2.00 (s, 6H), 4.53 (s, 1H), 7.53 (d, 1H), 7.58 (t, 1H), 7.76 (m, 3H), 7.92 (d, 1H), 8.46 (d, 2H), 9.58 (s, 1H), 10.62 (s, 1H) ppm | 3-(3,5-dicyano-1,4-dihydro-2,6-dimethyl-4-pyridinyl)-N-4-pyridinyl-benzamide |
| 43 | 3, -C(O)NH-(2-pyridyl) | (DMSO-D6, 400 MHz): δ = 2.00 (s, 6H), 4.52 (s, 1H), 7.15 (d, 1H), 7.50 (m, 2H), 7.82 (dd, 1H), 7.88 (s, 1H), 7.98 (d, 1H), 8.18 (d, 1H), 8.38 (d, 1H), 9.60 (s, 1H), 10.83 (s, 1H) ppm | 3-(3,5-dicyano-1,4-dihydro-2,6-dimethyl-4-pyridinyl)-N-2-pyridinyl-benzamide |

TABLE 1-continued

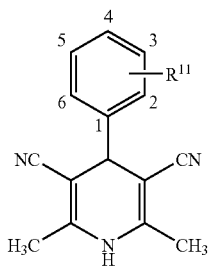

| Cpd No. | R[11] | 1H NMR | Name |
|---|---|---|---|
| 44 | 3, (acetamide linked to hexahydro-2-oxo-1H-azepin-3-yl) | (DMSO-D6, 400 MHz): δ = 1.21 (q, 1H), 1.52 (m, 1H), 1.63 (m, 1H), 1.75 (m, 1H), 1.87 (m, 1H), 2.02 (s, 6H), 3.08 (m, 1H), 3.20 (m, 1H), 4.48 (s, 1H), 4.59 (m, 1H), 7.42 (d, 1H), 7.50 (t, 1H), 7.72 (s, 1H), 7.80 (d, 1H), 7.85 (t, 1H), 8.28 (d, 1H), 9.54 (s, 1H) ppm | 3-(3,5-dicyano-1,4-dihydro-2,6-dimethyl-4-pyridinyl)-N-(hexahydro-2-oxo-1H-azepin-3-yl)-benzamide |
| 45 | 3, (C(O)NH-CH2CH2CH2-OEt) | (DMSO-D6, 400 MHz): δ = 1.14 (t, 3H), 1.70-1.78 (m, 2H), 2.04 (s, 6H), 3.23-3.32 (m, 2H), 3.36-3.42 (m, 2H), 4.45 (s, 1H), 7.38-7.42 (dt, 1H), 7.46 (t, 1H), 7.68-7.71 (m, 1H), 7.73-7.77 (dt, 1H), 8.46-8.51 (br t, 1H), 9.36 (br s, 1H) ppm | 3-(3,5-dicyano-1,4-dihydro-2,6-dimethyl-4-pyridinyl)-N-(3-ethoxypropyl)-benzamide |
| 46 | 3, (C(O)NH-CH2-4-pyridinyl) | (DMSO-D6, 400 MHz): δ = 2.02 (s, 6H), 4.48 (m, 3H), 7.30 (d, 1H), 7.45 (d, 1H), 7.50 (t, 1H), 7.78 (s, 1H), 7.84 (d, 1H), 8.43 (m, 2H), 9.18 (t, 1H), 9.54 (s, 1H) ppm | 3-(3,5-dicyano-1,4-dihydro-2,6-dimethyl-4-pyridinyl)-N-(4-pyridinylmethyl)-benzamide |
| 47 | 3, (NHC(O)CH2Br) | (DMSO-D6, 400 MHz): δ = 10.45 (s, 1H), 9.55 (s, 1H), 7.61 (m, 1H), 7.47 (m, 1H), 7.36 (m, 1H), 7.00 (m, 1H), 4.39 (s, 1H), 4.04 (s, 2H), 2.04 (s, 6H) ppm | 2-bromo-N-[3-(3,5-dicyano-1,4-dihydro-2,6-dimethyl-4-pyridinyl)phenyl]-acetamide |
| 48 | 3, (C(O)NH-CH2CH2-imidazol-1-yl) | (DMSO-D6, 400 MHz): δ = 2.00 (s, 6H), 3.55 (m, 2H), 4.15 (m, 2H), 4.47 (s, 1H), 6.90 (s, 1H), 7.18 (s, 1H), 7.41 (d, 1H), 7.47 (t, 1H), 7.66 (m, 2H), 7.70 (d, 1H), 8.65 (t, 1H), 9.55 (s, 1H) ppm | 3-(3,5-dicyano-1,4-dihydro-2,6-dimethyl-4-pyridinyl)-N-[2-(1H-imidazol-1-yl)ethyl]-benzamide |
| 49 | 3, (C(O)NH-6-(trifluoromethyl)-3-pyridinyl) | (DMSO-D6, 400 MHz): δ = 2.00 (s, 6H), 4.53 (s, 1H), 7.53 (d, 1H), 7.58 (t, 1H), 7.80 (s, 1H), 7.92 (d, 1H), 7.96 (d, 1H), 8.42 (d, 1H), 9.08 (s, 1H), 9.58 (br s, 1H), 10.85 (br s, 1H) ppm | 3-(3,5-dicyano-1,4-dihydro-2,6-dimethyl-4-pyridinyl)-N-[6-(trifluoromethyl)-3-pyridinyl]-benzamide |
| 50 | 3, (C(O)NH-CH2CH2CH2-OH) | (DMSO-D6, 400 MHz): δ = 1.64-1.71 (m, 2H), 2.04 (s, 6H), 3.28-3.33 (m, 2H), 3.43-3.48 (m, 2H), 4.55-4.82 (m, 2H), 7.40-7.43 (dt, 1H), 7.46-7.50 (1H), 7.71-7.72 (m, 1H), 7.76-7.78 (dt, 1H), 8.48-8.51 (br t, 1H), 9.56 (br s, 1H) ppm | 3-(3,5-dicyano-1,4-dihydro-2,6-dimethyl-4-pyridinyl)-N-(3-hydroxypropyl)-benzamide |

TABLE 1-continued

| Cpd No. | R¹¹ | 1H NMR | Name |
|---|---|---|---|
| 51 | 3, -C(O)NH-(5-methyl-2-pyridinyl) | (DMSO-D6, 400 MHz): δ = 8.17 (s, 1H), 8.12 (d, 1H), 7.91 (m, 2H), 7.66 (d, 1H), 7.55 (m, 2H), 4.5 (s, 1H), 2.3 (s, 3H), 2.0 (s, 6H) ppm | 3-(3,5-dicyano-1,4-dihydro-2,6-dimethyl-4-pyridinyl)-N-(5-methyl-2-pyridinyl)-benzamide |
| 52 | 3, -C(O)NH-(4-methyl-2-pyridinyl) | (DMSO-D6, 400 MHz): δ = 9.57 (1H, s), 7.83 (m, 1H), 7.81 (s, 1H), 7.72 (d, 1H), 7.55 (d, 1H), 6.3 (m, 1H), 6.21 (s, 1H), 4.56 (s, 1H), 2.12 (s, 3H), 2.01 (s, 6H) ppm | 3-(3,5-dicyano-1,4-dihydro-2,6-dimethyl-4-pyridinyl)-N-(4-methyl-2-pyridinyl)-benzamide |
| 53 | 3, -(3-pyridinyl) | (DMSO-D6, 400 MHz): δ = 2.02 (s, 6H), 4.50 (s, 1H), 7.33 (d, 1H), 7.55 (m, 3H), 7.65 (d, 1H), 8.05 (d, 1H), 8.55 (d, 1H), 8.86 (s, 1H), 9.55 (s, 1H) ppm | 1,4-dihydro-2,6-dimethyl-4-[3-(3-pyridinyl)phenyl]-3,5-pyridinedicarbonitrile |
| 54 | 3, -NHC(O)CH₂NHCH₂CH₂-(1H-imidazol-5-yl) | (DMSO-D6, 400 MHz): δ = 9.93 (s, 1H), 9.53 (s, 1H), 7.59 (m, 1H), 7.50 (m, 2H), 7.32 (m, 1H), 6.95 (m, 1H), 6.78 (m, 1H), 4.36 (s, 1H), 4.10 (m, 1H), 3.30 (m, 1H), 3.17 (m, 2H), 2.78 (m, 2H), 2.66 (m, 2H), 2.04 (s, 6H) ppm | N-[3-(3,5-dicyano-1,4-dihydro-2,6-dimethyl-4-pyridinyl)phenyl]-2-[[2-(1H-imidazol-5-yl)ethyl]amino]-acetamide |
| 55 | 3, -C(O)NH-(5-chloro-2-pyridinyl) | (DMSO-D6, 400 MHz): δ = 2.00 (s, 6H), 4.53 (s, 1H), 7.50 (m, 2H), 7.86 (s, 1H), 7.98 (m, 2H), 8.20 (d, 1H), 8.40 (s, 1H), 9.58 (s, 1H), 11.08 (s, 1H) ppm | N-(5-chloro-2-pyridinyl)-3-(3,5-dicyano-1,4-dihydro-2,6-dimethyl-4-pyridinyl)-benzamide |
| 56 | 3, -(1H-pyrazol-5-yl) | (DMSO-D6, 400 MHz): δ = 9.52 (s, 1H), 8.2 (s, 1H), 7.88 (s, 1H), 7.53 (d, 1H), 7.42 (s, 1H), 3.37 (t, 1H), 7.06 (d, 1H), 4.39 (s, 1H), 2.03 (s, 6H) ppm | 1,4-dihydro-2,6-dimethyl-4-[3-(1H-pyrazol-5-yl)phenyl]-3,5-pyridinedicarbonitrile |
| 57 | 3, -NHC(O)-(4-pyridinyl) | (DMSO-D6, 400 MHz): δ = 2.04 (s, 6H), 4.40 (s, 1H), 7.03-7.05 (d, 1H), 7.37-7.41 (t, 1H), 7.69 (m, 1H), 7.78-7.79 (d, 1H), 7.85-7.87 (dd, 2H), 8.77-8.78 (dd, 2H), 9.54 (s, 1H), 10.56 (s, 1H) ppm | N-[3-(3,5-dicyano-1,4-dihydro-2,6-dimethyl-4-pyridinyl)phenyl]-4-pyridinecarboxamide |
| 58 | 3, -NHC(O)-(2-pyridinyl) | (DMSO-D6, 400 MHz): δ = 2.05 (s, 6H), 4.38 (s, 1H), 7.01-7.03 (d, 1H), 7.35-7.39 (t, 1H), 7.66-7.69 (m, 1H), 7.88-7.90 (m, 2H), 8.05-8.09 (m, 1H), 8.14-8.16 (dd, 1H), 8.73-8.75 (m, 1H), 9.54 (s, 1H), 10.68 (s, 1H) ppm | N-[3-(3,5-dicyano-1,4-dihydro-2,6-dimethyl-4-pyridinyl)phenyl]-2-pyridinecarboxamide |

TABLE 1-continued

| Cpd No. | R[11] | 1H NMR | Name |
|---|---|---|---|
| 59 | 3, -C(O)NH-(6-methyl-3-pyridinyl) | (DMSO-D6, 400 MHz): δ = 2.02 (s, 6H), 2.41 (s, 3H), 4.55 (s, 1H), 7.22 (d, 1H), 7.50 (d, 1H), 7.55 (t, 1H), 7.80 (s, 1H), 7.90 (d, 1H), 8.03 (d, 1H), 8.77 (s, 1H), 9.58 (s, 1H), 10.40 (s, 1H) ppm | 3-(3,5-dicyano-1,4-dihydro-2,6-dimethyl-4-pyridinyl)-N-(6-methyl-3-pyridinyl)-benzamide |
| 60 | 3, -C(O)NH-(5-CF3-2-pyridinyl) | (DMSO-D6, 400 MHz): δ = 2.00 (s, 6H), 4.53 (s, 1H), 7.55 (m, 2H), 7.88 (s, 1H), 8.00 (d, 1H), 8.24 (d, 1H), 8.38 (d, 1H), 8.76 (s, 1H), 9.58 (s, 1H), 11.35 (s, 1H) ppm | 3-(3,5-dicyano-1,4-dihydro-2,6-dimethyl-4-pyridinyl)-N-[5-(trifluoromethyl)-2-pyridinyl]-benzamide |
| 61 | 3, -C(O)NH-(2-thiazolyl) | (DMSO-D6, 400 MHz): δ = 2.00 (s, 6H), 4.53 (s, 1H), 7.25 (s, 1H), 7.55 (m, 3H), 7.95 (s, 1H), 8.05 (d, 1H), 9.58 (s, 1H), 12.70 (br s, 1H) ppm | 3-(3,5-dicyano-1,4-dihydro-2,6-dimethyl-4-pyridinyl)-N-2-thiazolyl-benzamide |
| 62 | 3, -C(O)NH-(6-methyl-2-pyridinyl) | 1H NMR (DMSO-d6, 400 MHz): d/ppm = 2.00 (2, 6H), 2.43 (s, 2H), 4.53 (s, 1H), 7.00 (d, 1H), 7.50 (m, 2H), 7.70 (t, 1H), 7.88 (s, 1H), 7.98 (m, 2H), 9.58 (s, 1H), 10.75 (s, 1H) ppm | 3-(3,5-dicyano-1,4-dihydro-2,6-dimethyl-4-pyridinyl)-N-(6-methyl-2-pyridinyl)-benzamide |
| 63 | 3, -C(O)NH-(5-dimethylamino-2-pyridinyl) | (DMSO-D6, 400 MHz): δ = 2.02 (s, 6H), 2.86 (s, 6H), 4.50 (s, 1H), 7.20 (dd, 1H), 7.45 (d, 1H), 7.50 (t, 1H), 7.87 (m, 2H), 7.95 (m, 1H), 9.55 (s, 1H), 10.56 (s, 1H) ppm | 3-(3,5-dicyano-1,4-dihydro-2,6-dimethyl-4-pyridinyl)-N-[5-(dimethylamino)-2-pyridinyl]-benzamide |
| 64 | 3, -C(O)NH-(1H-pyrazol-3-yl) | (DMSO-D6, 400 MHz): δ = 2.02 (s, 6H), 4.50 (s, 1H), 6.62 (s, 1H), 7.45 (m, 2H), 7.63 (s, 1H), 7.84 (s, 1H), 7.95 (m, 1H), 9.58 (s, 1H), 10.87 (s, 1H), 12.40 (s, 1H) ppm | 3-(3,5-dicyano-1,4-dihydro-2,6-dimethyl-4-pyridinyl)-N-1H-pyrazol-3-yl-benzamide |
| 65 | 3, -NHC(O)-(1H-imidazol-2-yl) | (DMSO-D6, 400 MHz): δ = 2.04 (s, 6H), 4.34 (s, 1H), 6.97-6.99 (d, 1H), 7.16 (s, 1H), 7.31-7.37 (m, 2H), 7.82-7.84 (m, 2H), 9.52 (s, 1H), 10.41 (s, 1H) ppm | N-[3-(3,5-dicyano-1,4-dihydro-2,6-dimethyl-4-pyridinyl)phenyl]-1H-imidazole-2-carboxamide |
| 66 | 3, -NHC(O)-(1H-imidazol-5-yl) | (DMSO-D6, 400 MHz): δ = 2.04 (s, 6H), 4.33 (s, 1H), 6.93-6.95 (d, 1H), 7.29-7.33 (t, 1H), 7.78-7.82 (m, 4H), 9.51 (s, 1H), 9.85 (br s, 1H) ppm | N-[3-(3,5-dicyano-1,4-dihydro-2,6-dimethyl-4-pyridinyl)phenyl]-1H-imidazole-5-carboxamide |

TABLE 1-continued

| Cpd No. | R[11] | 1H NMR | Name |
|---|---|---|---|
| 67 | 3, -C(O)NH-(1H-tetrazol-5-yl) | (DMSO-D6, 400 MHz): δ = 1.10 (t, 9H), 2.02 (s, 6H), 2.96 (q, 6H), 3.30 (br, 2H), 4.50 (s, 1H), 7.45 (m, 2H), 7.83 (s, 1H), 7.94 (d, 1H), 9.58 (s, 1H) ppm | (AutoNom 2000 name) 3-(3,5-dicyano-2,6-dimethyl-1,4-dihydro-pyridin-4-yl)-N-(1H-tetrazol-5-yl)-benzamide |
| 68 | 3, -C(O)NH-(6-amino-2-pyridinyl) | (DMSO-D6, 400 MHz): δ = 2.02 (s, 6H), 4.50 (s, 1H), 5.78 (br s, 1H), 6.20 (d, 1H), 7.30 (d, 1H), 7.40 (t, 1H), 7.46 (m, 1H), 7.50 (t, 1H), 7.80 (s, 1H), 7.90 (d, 1H), 9.55 (s, 1H), 10.18 (s, 1H) ppm | N-(6-amino-2-pyridinyl)-3-(3,5-dicyano-1,4-dihydro-2,6-dimethyl-4-pyridinyl)-benzamide |
| 69 | 4, -(2H-tetrazol-5-yl) | (DMSO-D6, 400 MHz): δ = 9.55 (s, 1H), 7.99 (d, 2H), 7.33 (d, 2H), 4.41 (s, 1H), 2.02 (s, 6H) ppm | 1,4-dihydro-2,6-dimethyl-4-[4-(2H-tetrazol-5-yl)phenyl]-3,5-pyridinedicarbonitrile |
| 70 | 4, -C(=NOCH₃)CH₃ (3-substituted phenyl) | (DMSO-D6, 400 MHz): δ = 9.53 (s, 1H), 7.57 (d, 1H), 7.51 (s, 1H), 7.43 (t, 1H), 7.30 (d, 1H), 4.46 (s, 1H), 3.92 (s, 3H), 2.18 (s, 3H), 2.01 (s, 6H) ppm | 1,4-dihydro-4-[3-[(1E)-1-(methoxyimino)ethyl]phenyl]-2,6-dimethyl-3,5-pyridinedicarbonitrile |
| 71 | 4, -C(=NOH)CH₃ (3-substituted phenyl) | (DMSO-D6, 400 MHz): δ = 11.26 (s, 1H), 9.51 (s, 1H), 7.55 (s, 1H), 7.54 (d, 1H), 7.41 (t, 1H), 7.25 (d, 1H), 4.43 (s, 1H), 2.14 (s, 3H), 2.01 (s, 6H) ppm | 1,4-dihydro-4-[3-[(1E)-1-(hydroxyimino)ethyl]phenyl]-2,6-dimethyl-3,5-pyridinedicarbonitrile |
| 72 | 4, -C(O)NH-[5-(hydroxymethyl)-2-pyridinyl] | (DMSO-D6, 400 MHz): δ = 2.02 (s, 6H), 4.48 (d, 2H), 4.50 (s, 1H), 5.25 (t, 1H), 7.48 (m, 1H), 7.52 (t, 1H), 7.76 (dd, 1H), 7.89 (s, 1H), 7.98 (m, 1H), 8.13 (d, 1H), 8.32 s, 1H), 9.55 (s, 1H), 10.82 (s, 1H) ppm | 3-(3,5-dicyano-1,4-dihydro-2,6-dimethyl-4-pyridinyl)-N-[5-(hydroxymethyl)-2-pyridinyl]-benzamide |

TABLE 1-continued

| Cpd No. | R11 | 1H NMR | Name |
|---|---|---|---|
| 73 | 3, -CH(NH2)- (aminomethyl, stereo) | (DMSO-D6, 400 MHz): δ = 9.46 (s, 1H), 7.30 (m, 3H), 7.17 (s, 1H), 7.06 (d, 1H), 4.37 (s, 1), 3.71 (s, 1H), 2.01 (s, 6H) ppm | 4-[3-(aminomethyl)phenyl]-1,4-dihydro-2,6-dimethyl-3,5-pyridinedicarbonitrile |
| 74 | 3, -CH2-NH-C(O)-(1H-imidazol-4-yl) | (CD3OD, 400 MHz): δ = 7.38 (t, 1H), 7.35 (m, 3H), 7.28 (s, 1H), 7.22 (d, 1H), 4.60 (s, 2), 4.37 (s, 1H), 2.04 (s, 6H) ppm | |
| 75 | 3, -C(O)-NH-(pyrazin-2-yl) | (DMSO-D6, 400 MHz): δ = 2.02 (s, 6H), 4.50 (s, 1H), 7.53 (m, 2H), 7.84 (s, 1H), 7.95 (m, 1H), 8.40 (s, 1H), 8.45 (s, 1H), 9.40 (s, 1H), 9.55 (s, 1H), 11.20 (s, 1H) ppm | 3-(3,5-dicyano-1,4-dihydro-2,6-dimethyl-4-pyridinyl)-N-pyrazinyl-benzamide |
| 76 | 3, -C(O)-NH-(5-[(dimethylamino)methyl]pyridin-2-yl) | (DMSO-D6, 400 MHz): δ = 2.02 (s, 6H), 2.13 (s, 6H), 3.38 (s, 2H), 4.50 (s, 1H), 5.25 (t, 1H), 7.50 (m, 2H), 7.72 (d, 1H), 7.89 (s, 1H), 7.98 (d, 1H), 8.13 (d, 1H), 8.27 (s, 1H), 9.55 (s, 1H), 10.82 (s, 1H) ppm | 3-(3,5-dicyano-1,4-dihydro-2,6-dimethyl-4-pyridinyl)-N-[5-[(dimethylamino)methyl]-2-pyridinyl]-benzamide |
| 77 | 3, —F and 4, —CN | (DMSO-D6, 400 MHz): δ = 9.57 (br. s, 1H), 7.99 (dd, 1H), 7.52 (dd, 1H), 7.41 (dd, 1H), 4.6 (s, 1H), 2.1 (s, 6H) ppm | 4-(4-cyano-3-fluorophenyl)-1,4-dihydro-2,6-dimethyl-3,5-pyridinedicarbonitrile |
| 78 | 3, —CN and 4, —F | (DMSO-D6, 400 MHz): δ = 9.61 (br. s, 1H), 7.97 (dd, 1H), 7.48 (dd, 1H), 7.35 (dd, 1H), 4.64 (s, 1H), 2.01 (s, 6H) ppm | 4-(3-cyano-4-fluorophenyl)-1,4-dihydro-2,6-dimethyl-3,5-pyridinedicarbonitrile |
| 79 | 3, —OCF3 and 4, —OH | (DMSO-D6, 400 MHz): δ = 10.22 (s, 1H), 9.47 (s, 1H), 7.08 (d, 2H), 7.02 (s, 1H), 4.37 (s, 1H), 2.01 (s, 6H) ppm | 1,4-dihydro-4-][4-hydroxy-3-(trifluoromethoxy)phenyl]-2,6-dimethyl-3,5-pyridinedicarbonitrile |

TABLE 2

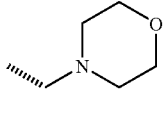

| Cpd No. | R[11] | R[12] | 1H NMR | Name |
|---|---|---|---|---|
| 80 | H | H | (400 MHz, CDCl3): δ = 8.07 (s, 1H), 7.64 (s, 1H), 7.53 (d, 1H), 7.35 (d, 1H), 4.48 (s, 1H), 2.03 (s, 6H) ppm | 1,4-dihydro-4-(1H-indazol-5-yl)-2,6-dimethyl-3,5-pyridinedicarbonitrile |
| 81 | CH$_3$ | H | (DMSO-D6, 400 MHz): δ = 12.68 (s, 1H), 9.51 (s, 1H), 7.53 (s, 1H), 7.49 (d, 1H), 7.27 (d, 1H), 4.50 (s, 1H), 2.49 (s, 3H), 2.05 (s, 6H) ppm | 1,4-dihydro-2,6-dimethyl-4-(3-methyl-1H-indazol-5-yl)-3,5-pyridinedicarbonitrile |
| 82 | NH$_2$ | H | (DMSO-D6, 300 MHz): δ = 11.39 (br. s, 1H), 9.47 (br. s, 1H), 7.50 (m, 1H), 7.20 (d, 1H), 7.11 (dd, 1H), 5.34 (br. s, 2H), 4.34 (s, 1H), 2.01 (s, 6H) ppm | 4-(3-amino-1H-indazol-5-yl)-1,4-dihydro-2,6-dimethyl-3,5-pyridinedicarbonitrile |
| 83 | 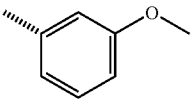 | H | (DMSO-D6, 400 MHz): δ = 9.54 (s, 1H), 7.75 (s, 1H), 7.48 (d, 1H), 7.24 (d, 1H), 4.47 (s, 1H), 3.52 (m, 4H), 2.41 (m, 4H), 2.02 (s, 6H) ppm | 1,4-dihydro-2,6-dimethyl 4-[3-(4-morpholinylmethyl)-1H-indazol-5-yl]-3,5-pyridinedicarbonitrile |
| 84 | 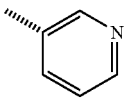 | H | (DMSO-D6, 400 MHz): δ = 13.3 (s, 1H), 9.54 (s, 1H), 7.88 (s, 1H), 7.63 (d, 1H), 7.57 (d, 1H), 7.45 (m, 2H), 7.37 (d, 1H), 6.98 (d, 1H), 4.62 (s, 1H), 3.83 (s, 3H), 2.04 (s, 6H) ppm | 1,4-dihydro-4-[3-(3-methoxyphenyl)-1H-indazol-5-yl]-2,6-dimethyl-3,5-pyridinedicarbonitrile |
| 85 | —CO$_2$CH$_3$ | H | (DMSO-D6, 400 MHz): δ = 8.04 (s, 1H), 7.72 (s, 1H), 7.49 (d, 1H), 4.58 (s, 1H), 4.02 (s, 3H), 2.0 (s, 6H) ppm | 5-(3,5-dicyano-1,4-dihydro-2,6-dimethyl-4-pyridinyl)-1H-indazole-3-carboxylic acid methyl ester |
| 86 | —CO$_2$H | H | (DMSO-D6, 400 MHz): δ = 8.04 (s, 1H), 7.78 (s, 1H), 7.41 (d, 1H), 4.62 (s, 1H), 2.1 (s, 6H) ppm. | 5-(3,5-dicyano-1,4-dihydro-2,6-dimethyl-4-pyridinyl)-1H-indazole-3-carboxylic acid |
| 87 | 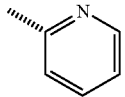 | H | (DMSO-D6, 400 MHz): δ = 9.51 (br. S, 1H), 9.18 (s, 1H), 8.61 (d, 1H), 8.34 (d, 1H), 7.91 (s, 1H), 7.65 (d, 1H), 7.56 (dd, 1H), 7.4 (d, 1H), 4.62 (s, 1H), 2.01 (s, 6H) ppm | 1,4-dihydro-2,6-dimethyl-4-[3-(3-pyridinyl)-1H-indazol-5-yl]-3,5-pyridinedicarbonitrile |
| 88 |  | H | (DMSO-D6, 400 MHz): δ = 8.76 (d, 2H), 8.17 (d, 1H), 7.79 (d, 1H), 7.58 (d, 1H), 4.71 (s, 1H), 2.12 (s, 6H) ppm | 1,4-dihydro-2,6-dimethyl-4-[3-(2-pyridinyl)-1H-indazol-5-yl]-3,5-pyridinedicarbonitrile |

TABLE 2-continued

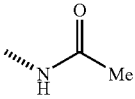

| Cpd No. | R11 | R12 | 1H NMR | Name |
|---|---|---|---|---|
| 89 | 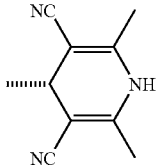 | H | | N-[5-(3,5-dicyano-1,4-dihydro-2,6-dimethyl-4-pyridinyl)-1H-indazol-3-yl]-acetamide |
| 90 | 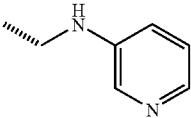 | H | (DMSO-D6, 400 MHz): δ = 12.9 (s, 1H), 9.62 (s, 1H), 9.44 (s, 1HO, 7.55 (d, 1H), 7.33 (s, 1H), 7.21 (d, 1H), 4.78 (s, 1H), 4.42 (s, 1H), 2.0 (m, 12H) ppm | |
| 91 | 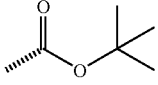 | H | (DMSO-D6, 400 MHz): δ = 9.47 (s, 1H), 8.04 (s, 1H), 7.72 (s, 1H), 7.64 (s, 1H), 7.46 (d, 1H), 7.22 (d, 1H), 7.01 (m, 2H), 6.47 (m, 1H), 4.59 (m, 2H), 4.42 (s, 1H), 2.0 (s, 6H) ppm | 1,4-dihydro-2,6-dimethyl-4-[3-[(3-pyridinylamino)methyl]-1H-indazol-5-yl]-3,5-pyridinedicarbonitrile |
| 92 | $NH_2$ | 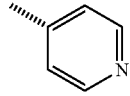 | (DMSO-D6, 300 MHz): δ = 9.53 (br s, 1H), 7.91 (d, 1H), 7.71 (m, 1H), 7.41 (dd, 1H), 6.34 (br s, 2H), 4.47 (s, 1H), 2.02 (s, 6H), 1.55 (s, 9H) ppm | 3-amino-5-(3,5-dicyano-1,4-dihydro-2,6-dimethyl-4-pyridinyl)-1H-indazole-1-carboxylic acid tert-butyl ester |
| 93 | I | H | (DMSO-D6, 400 MHz): δ = 9.54 (s, 1H), 9.4 (s, 1H), 7.6 (d, 1H), 7.41 (d, 1H), 7.24 (s, 1H), 4.6 (s, 1H), 2.01 (s, 6H) ppm | 1,4-dihydro-4-(3-iodo-1H-indazol-5-yl)-2,6-dimethyl-3,5-pyridinedicarbonitrile |
| 94.1 | 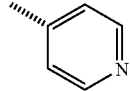 | H | | (AutoNom 2000 name) 2,6-dimethyl-4-(3-pyridin-4-yl-1H-indazol-5-yl)-1,4-dihydro-pyridine-3,5-dicarbonitrile |
| 94.2 | 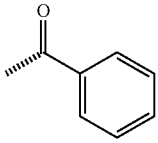<br>Acetic acid salt | H | (DMSO-D6, 400 MHz): δ = 8.76 (d, 2H), 8.17 (d, 2H), 7.79 (d, 1H), 7.58 (d, 1H), 4.71 (s, 1H), 2.12 (s, 6H) ppm | (AutoNom 2000 name) 2,6-dimethyl-4-(3-pyridin-4-yl-1H-indazol-5-yl)-1,4-dihydro-pyridine-3,5-dicarbonitrile, acetic acid salt |
| 95 | $NH_2$ |  | | 4-(3-amino-1-benzoyl-1H-indazol-5-yl)-1,4-dihydro-2,6-dimethyl-3,5-pyridinedicarbonitrile |

TABLE 2-continued

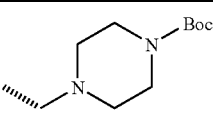

| Cpd No. | R11 | R12 | 1H NMR | Name |
|---|---|---|---|---|
| 96 | 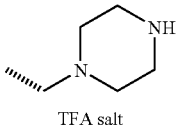 | H | (DMSO-D6, 400 MHz): δ = 9.58 (s, 1H), 7.79 (s, 1H), 7.63 (d, 1H), 7.38 (d, 1H), 4.52 (s, 1H), 3.4 (m, 4H), 3.12 (m, 4H), 2.1 (s, 6H), 1.38 (s, 9H) ppm | (AutoNom 2000 name) 4-[5-(3,5-dicyano-2,6-dimethyl-1,4-dihydro-pyridin-4-yl)-1H-indazol-3-ylmethyl]-piperazine-1-carboxylic acidtert-butyl ester, TFA salt |
| 97.1 | 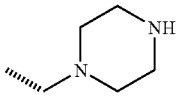<br>TFA salt | H | (DMSO-D6, 400 MHz): δ = 9.56 (s, 1H), 7.75 (s, 1H), 7.59 (d, 1H), 7.33 (d, 1H), 4.52 (s, 1H), 3.55 (m, 4H), 3.17 (m, 4H), 2.03 (s, 6H) ppm | (AutoNom 2000 name) 2,6-dimethyl-4-(3-piperazin-1-ylmethyl-1H-indazol-5-yl)-1,4-dihydro-pyridine-3,5-dicarbonitrile, TFA salt |
| 97.2 | 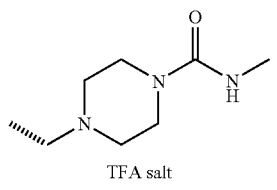 | H |  | (AutoNom 2000 name) 2,6-dimethyl-4-(3-piperazin-1-ylmethyl-1H-indazol-5-yl)-1,4-dihydro-pyridine-3,5-dicarbonitrile |
| 98.1 | 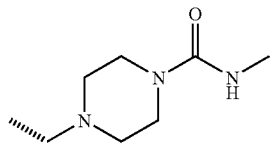<br>TFA salt | H | (DMSO-D6, 400 MHz): δ = 9.5 (s, 1H), 7.71 (s, 1H), 7.62 (d, 1H), 7.36 (d, 1H), 4.58 (s, 1H), 3.51 (m, 4H), 3.27 (m, 4H), 2.03 (s, 6H) ppm | 4-[[5-(3,5-dicyano-1,4-dihydro-2,6-dimethyl-4-pyridinyl)-1H-indazol-3-yl]methyl]-N-methyl-1-piperazinecarboxamide, TFA salt |
| 98.2 | 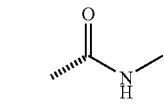 | H |  | 4-[[5-(3,5-dicyano-1,4-dihydro-2,6-dimethyl-4-pyridinyl)-1H-indazol-3-yl]methyl]-N-methyl-1-piperazinecarboxamide |
| 99.1 | 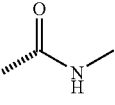<br>TFA salt | H |  | 5-(3,5-dicyano-1,4-dihydro-2,6-dimethyl-4-pyridinyl)-N-methyl-1H-indazole-3-carboxamide, TFA salt |
| 99.2 |  | H | (DMSO-D6, 400 MHz): δ = 9.52 (s, 1H), 8.3 (br. s, 1H), 7.97 (s, 1H), 7.56 (d, 1H), 7.28 (d, 1H), 4.51 (s, 1H), 2.78 (d, 3H), 1.98 (s, 6H) ppm | 5-(3,5-dicyano-1,4-dihydro-2,6-dimethyl-4-pyridinyl)-N-methyl-1H-indazole-3-carboxamide |
| 100 | —NH2 | CH3 |  | 4-(3-amino-1-methyl-1H-indazol-5-yl)-1,4-dihydro-2,6-dimethyl-3,5-pyridinedicarbonitrile |

TABLE 2-continued

| Cpd No. | R11 | R12 | 1H NMR | Name |
|---|---|---|---|---|
| 101 | N(C(=O)Ph)₂ | Boc | | 3-(dibenzoylamino)-5-(3,5-dicyano-1,4-dihydro-2,6-dimethyl-4-pyridinyl)-1H-indazole-1-carboxylic acid 1,1-dimethylethyl ester |
| 102 | NHC(=O)Ph | CH₃ | | N-[5-(3,5-dicyano-1,4-dihydro-2,6-dimethyl-4-pyridinyl)-1-methyl-1H-indazol-3-yl]-benzamide |
| 103.1 | NHC(=O)CH₂CH₂N(CH₃)₂ TFA salt | H | | 5-(3,5-dicyano-1,4-dihydro-2,6-dimethyl-4-pyridinyl)-N-[2-(dimethylamino)ethyl]-1H-indazole-3-carboxamide, TFA salt |
| 103.2 | NHC(=O)CH₂CH₂N(CH₃)₂ | H | (DMSO-D6, 400 MHz): δ = 8.16 (s, 1H), 7.63 (d, 1H), 7.41 (d, 1H), 4.55 (s, 1H), 3.82 (t, 2H), 3.43 (t, 2H), 3.01 (s, 6H), 2.14 (s, 6H) ppm | 5-(3,5-dicyano-1,4-dihydro-2,6-dimethyl-4-pyridinyl)-N-[2-(dimethylamino)ethyl]-1H-indazole-3-carboxamide |
| 104 | NHCH₂Ph | Boc | (DMSO-D6, 400 MHz): δ = 1.60 (s, 9H), 2.00 (s, 6H), 4.48 (m, 3H), 7.25 (t, 1H), 7.32 (t, 2H), 7.43 (m, 4H), 7.80 (s, 1H), 7.87 (d, 1H), 9.57 (s, 1H) ppm | 5-(3,5-dicyano-1,4-dihydro-2,6-dimethyl-4-pyridinyl)-3-[(phenylmethyl)amino]-1H-indazole-1-carboxylic acid 1,1-dimethylethyl ester |
| 105 | NHCH₂Ph | H | (DMSO-D6, 400 MHz): δ = 2.00 (s, 6H), 4.35 (s, 1H), 4.45 (dm, 2H), 6.57 (t, 1H), 7.14 (m, 1H), 7.20 (dd, 2H), 7.28 (dd, 1H), 7.38 (m, 2H), 7.60 (s, 1H), 9.43 (s, 1H), 11.42 (s, 1H). | 1,4-dihydro-2,6-dimethyl-4-[3-[(phenylmethyl)amino]-1H-indazol-5-yl]-3,5-pyridinedicarbonitrile |
| 106.1 | NHC(=O)CH₂CH₂CH₂N(CH₃)₂ TFA salt | H | (DMSO-D6, 400 MHz): δ = 9.55 (br. S, 1H), 8.22 (br. S, 1H), 8.02 (s, 1H), 7.63 (d, 1H), 7.36 (d, 1H), 4.56 (s, 1H), 3.41 (m, 2H), 3.31 (m, 4H), 2.59 (m, 2H), 2.04 (s, 6H), 1.7 (m, 4H) ppm | (AutoNom 2000 name) 5-(3,5-dicyano-2,6-dimethyl-1,4-dihydro-pyridin-4-yl)-1H-indazole-3-carboxylic acid (3-dimethylamino-propyl)-amide, TFA salt |

TABLE 2-continued

| Cpd No. | R11 | R12 | 1H NMR | Name |
|---|---|---|---|---|
| 106.2 | [structure: -NH-C(=O)-CH2-NH-CH2CH2CH2-N(CH3)2] | H | | (AutoNom 2000 name) 5-(3,5-dicyano-2,6-dimethyl-1,4-dihydro-pyridin-4-yl)-1H-indazole-3-carboxylic acid (3-dimethylamino-propyl)-amide |
| 107 | H | CH3 | (DMSO-D6, 400 MHz): δ = 9.51 (s, 1H), 8.33 (s, 1H), 7.61 (d, 1H), 7.52 (m, 1H), 7.17 (d, 1H), 4.42 (s, 1H), 4.16 (s, 3H), 2.04 (s, 6H) ppm | 1,4-dihydro-2,6-dimethyl-4-(1-methyl-1H-indazol-5-yl)-3,5-pyridinedicarbonitrile |
| 108 | [structure: =N-CH=3-pyridyl] | [structure: -CH(OMe)-3-pyridyl] | (DMSO-D6, 400 MHz): δ = 2.00 (s, 6H), 3.38 (s, 3H), 4.60 (s, 1H), 7.00 (s, 1H), 7.40 (d, 1H), 7.58 (dd, 1H), 7.76 (d, 1H), 7.80 (m, 2H), 8.44 (d, 1H), 8.54 (d, 1H), 8.65 (s, 1H), 8.72 (d, 1H), 9.18 (s, 1H), 9.24 (s, 1H), 9.57 (s, 1H) ppm | 1,4-dihydro-4-[1-(methoxy-3-pyridinylmethyl)-3-[[(1E)-3-pyridinylmethylene]amino]-1H-indazol-5-yl]-2,6-dimethyl-3,5-pyridinedicarbonitrile |
| 109 | [structure: =N-CH=3-pyridyl] | H | (DMSO-D6, 400 MHz): δ = 2.00 (s, 6H), 4.60 (s, 1H), 7.38 (d, 1H), 7.58 (m, 2H), 7.76 (s, 1H), 8.44 (d, 1H), 8.70 (d, 1H), 9.16 (s, 1H), 9.28 (s, 1H), 9.53 (br s, 1H), 13.15 (br s, 1H) ppm | 1,4-dihydro-2,6-dimethyl-4-[3-[[(1E)-3-pyridinylmethylene]amino]-1H-indazol-5-yl]-3,5-pyridinedicarbonitrile |
| 110 | NH2 | [structure: -CH(OMe)-3-pyridyl] | (DMSO-D6, 400 MHz): δ = 2.00 (s, 6H), 3.24 (s, 3H), 4.35 (s, 1H), 5.70 (m, 2H), 6.67 (s, 1H), 7.20 (d, 1H), 7.35 (dd, 1H), 7.52 (d, 1H), 7.58 (s, 1H), 7.74 (d, 1H), 8.48 (d, 1H), 8.56 (s, 1H), 9.43 (s, 1H). | 4-[3-amino-1-(methoxy-3-pyridinylmethyl)-1H-indazol-5-yl]-1,4-dihydro-2,6-dimethyl-3,5-pyridinedicarbonitrile |
| 111 | [structure: 4-(piperazin-1-yl)phenyl] | H | (DMSO-D6, 400 MHz): δ = 9.55 (s, 1H), 7.81 (m, 3H), 7.58 (s, 1H), 7.33 (d, 1H), 7.05 (d, 2H), 4.58 (s, 1H), 3.16 (m, 4H), 2.91 (m, 4H), 2.02 (s, 6H) ppm | 1,4-dihydro-2,6-dimethyl-4-[3-[4-(1-piperazinyl)phenyl]-1H-indazol-5-yl]-3,5-pyridinedicarbonitrile |
| 112 | [structure: 4-(NHBoc)phenyl] | H | (400 MHz, CD3OD): δ = 8.13 (d, 2H), 8.05 (d, 2H), 7.91 (s, 1H), 7.63 (d, 1H), 7.43 (d, 1H), 6.25 (m, 1H), 4.57 (s, 1H), 2.12 (s, 6H), 1.4 (s, 9H) ppm | [4-[5-(3,5-dicyano-1,4-dihydro-2,6-dimethyl-4-pyridinyl)-1H-indazol-3-yl]phenyl]-carbamic acid 1,1-dimethylethyl ester |

TABLE 2-continued

| Cpd No. | R11 | R12 | 1H NMR | Name |
|---|---|---|---|---|
| 113 | 4-(4-Boc-piperazin-1-yl)phenyl | -CH2CH2-O-SiMe3 (SEM) | (400 MHz, CDCl3): δ = 8.18 (d, 2H), 8.03 (d, 2H), 7.85 (s, 1H), 7.64 (d, 1H), 7.42 (d, 1H), 6.06 (s, 1H), 5.8 (s, 2H0, 4.6 (s, 1H), 3.65 (t, 2H), 2.2 (s, 6H), 0.96 (t, 2H), 0.1 (s, 9H) ppm | [4-[5-(3,5-dicyano-1,4-dihydro-2,6-dimethyl-4-pyridinyl)-1-[[2-(trimethylsilyl)ethoxy]methyl]-1H-indazol-3-yl]phenyl]-carbamic acid 1,1-dimethylethyl ester |
| 114.1 | -C(O)N(CH3)2 (TFA salt) | H | (DMSO-D6, 400 MHz): δ = 13.5 (s, 1H), 9.46 (s, 1H), 7.78 (s, 1H), 7.57 (d, 1H), 7.33 (d, 1H), 4.53 (s, 1H), 3.02 (s, 6H), 1.97 (s, 6H) ppm | 5-(3,5-dicyano-2,6-dimethyl-1,4-dihydro-pyridin-4-yl)-1H-indazole-3-carboxylic acid dimethylamide, TFA salt |
| 114.2 | -C(O)N(CH3)2 | H |  | 5-(3,5-dicyano-2,6-dimethyl-1,4-dihydro-pyridin-4-yl)-1H-indazole-3-carboxylic acid dimethylamide |
| 115 | -NHC(O)NHCH3 | -NHC(O)CH3 |  | 5-(3,5-dicyano-1,4-dihydro-2,6-dimethyl-4-pyridinyl)-N-methyl-3-[[(methylamino)carbonyl]amino]-1H-indazole-1-carboxamide |
| 116 | -NH-CH2CH2-OTBS | Boc | (DMSO-D6, 400 MHz): δ = 0.00 (s, 6H), 0.80 (t, 6H), 1.58 (s, 9H), 2.00 (s, 6H), 3.38 (m, 2H), 3.77 (t, 2H), 4.48 (s, 1H), 6.78 (t, 1H), 7.42 (d, 1H), 7.73 (s, 1H), 7.87 (d, 1H), 9.57 (s, 1H) ppm | 5-(3,5-dicyano-1,4-dihydro-2,6-dimethyl-4-pyridinyl)-3-[[2-[1-methyl-1-(trimethylsilyl)ethoxy]ethyl]amino]-1H-indazole-1-carboxylic acid 1,1-dimethylethyl ester |
| 117 | -NH-CH2CH3 | Boc | (DMSO-D6, 400 MHz): δ = 1.22 (t, 3H), 1.60 (s, 9H), 2.00 (s, 6H), 3.60 (m, 2H), 4.48 (s, 1H), 6.80 (m, 1H), 7.42 (d, 1H), 7.78 (s, 1H), 7.87 (d, 1H), 9.57 (s, 1H) ppm | 5-(3,5-dicyano-1,4-dihydro-2,6-dimethyl-4-pyridinyl)-3-(ethylamino)-1H-indazole-1-carboxylic acid tert-butyl ester |
| 118 | -NH-CH2CH2-OH | H | (DMSO-D6, 400 MHz): δ = 2.00 (s, 6H), 3.40 (m, 2H), 3.63 (m, 2H), 4.50 (s, 1H), 7.45 (d, 1H), 7.55 (d, 1H), 8.00 (s, 1H), 9.57 (s, 1H) ppm | 1,4-dihydro-4-[3-[(2-hydroxyethyl)amino]-1H-indazol-5-yl]-2,6-dimethyl-3,5-pyridinedicarbonitrile |

TABLE 2-continued

| Cpd No. | R11 | R12 | 1H NMR | Name |
|---|---|---|---|---|
| 119 | ″″N(H)–CH2CH2–OH | Boc | (DMSO-D6, 400 MHz): δ = 1.60 (s, 9H), 2.00 (s, 6H), 3.35 (m, 2H), 3.60 (m, 2H), 4.48 (s, 1H), 4.75 (t, 1H), 6.90 9t, 1H), 7.22 (d, 1H), 7.78 (s, 1H), 7.87 (d, 1H), 9.57 (s, 1H) ppm | 5-(3,5-dicyano-1,4-dihydro-2,6-dimethyl-4-pyridinyl)-3-[(2-hydroxyethyl)amino]-1H-indazole-1-carboxylic acid 1,1-dimethylethyl ester |
| 120 | ″″N(H)–CH2–(3-pyridyl) | H | (DMSO-D6, 400 MHz): δ = 2.00 (s, 6H), 4.35 (s, 1H), 4.45 (d, 2H), 6.67 (t, 1H), 7.14 (d, 1H), 7.24 (d, 1H), 7.30 (dd, 1H), 7.56 (s, 1H), 7.78 (d, 1H), 8.40 (d, 1H), 8.60 (s, 1H), 9.43 (s, 1H), 11.44 (s, 1H) ppm | 1,4-dihydro-2,6-dimethyl-4-[3-[(3-pyridinylmethyl)amino]-1H-indazol-5-yl]-3,5-pyridinedicarbonitrile |
| 121 | ″″N(H)–CH2CH3 | H | (DMSO-D6, 400 MHz): δ = 1.20 (t, 3H), 2.00 (s, 6H), 3.25 (q, 2H), 4.35 (s, 1H), 5.90 (t, 1H), 7.10 (d, 1H), 7.20 (d, 1H), 7.50 (s, 1H), 9.25 (s, 1H), 11.38 (s, 1H) ppm | 4-[3-(ethylamino)-1H-indazol-5-yl]-1,4-dihydro-2,6-dimethyl-3,5-pyridinedicarbonitrile |
| 122 | ″″-(4-NHC(O)OCH3-phenyl) | —CH2OH | (400 MHz, CDCl3): δ = 9.52 (s, 1H), 8.13 (m, 4H), 8 (s, 1H), 7.91 (d, 1H), 7.46 (d, 1H), 5.8 (s, 2H), 4.63 (s, 1H), 3.92 (s, 3H), 2.03 (s, 6H) ppm | [4-[5-(3,5-dicyano-1,4-dihydro-2,6-dimethyl-4-pyridinyl)-1-(hydroxymethyl)-1H-indazol-3-yl]phenyl]-carbamic acid methyl ester |
| 123 | ″″-(4-NHC(O)OCH3-phenyl) | H | (DMSO-D6, 400 MHz): δ = 8.14 (d, 2H), 8.08 (d, 2H), 7.9 (s, 1H), 7.63 (d, 1H), 7.44 (d, 1H), 4.57 (s, 1H), 3.96 (s, 3H), 2.1 (s, 6H) ppm | [4-[5-(3,5-dicyano-1,4-dihydro-2,6-dimethyl-4-pyridinyl)-1H-indazol-3-yl]phenyl]-carbamic acid methyl ester |
| 124 | ″″-C(O)NH–CH2CH2-(1-pyrrolidinyl) | H | (DMSO-D6, 400 MHz): δ = 9.55 (br. S, 1H), 8.22 (br. S, 1H), 8.02 (s, 1H), 7.63 (d, 1H), 7.36 (d, 1H), 4.56 (s, 1H), 3.41 (m, 2H), 3.31 (m, 4H), 2.59 (m, 2H), 2.04 (s, 6H), 1.7 (m, 4H) ppm | 5-(3,5-dicyano-1,4-dihydro-2,6-dimethyl-4-pyridinyl)-N-[2-(1-pyrrolidinyl)ethyl]-1H-indazole-3-carboxamide |
| 125 | ″″-C(O)NH–CH2CH2-(1-methyl-2-pyrrolidinyl) | H | (DMSO-D6, 400 MHz): δ = 9.56 (s, 1H), 8.47 (m, 1H), 8.02 (s, 1H), 7.63 (d, 1H), 7.38 (d, 1H), 4.56 (s, 1H), 2.94 (m, 1H), 2.21 (s, 3H), 2.01 (s, 6H), 1.94 (m, 2H), 1.62 (m, 2H), 1.51 (m, 2H) ppm | 5-(3,5-dicyano-1,4-dihydro-2,6-dimethyl-4-pyridinyl)-N-[2-(1-methyl-2-pyrrolidinyl)ethyl]-1H-indazole-3-carboxamide |

TABLE 2-continued

| Cpd No. | R¹¹ | R¹² | 1H NMR | Name |
|---|---|---|---|---|
| 126 | =N-C₆H₄-NO₂ (4-nitrophenyl methyleneamino) | H | (DMSO-D6, 400 MHz): δ = 2.00 (s, 6H), 4.60 (s, 1H), 7.38 (d, 1H), 7.58 (d, 1H), 7.80 (s, 1H), 8.30 (d, 2H), 8.37 (d, 2H), 9.36 (s, 1H), 9.53 (br s, 1H), 13.25 (br s, 1H) ppm | 1,4-dihydro-2,6-dimethyl-4-[3-[[(1E)-(4-nitrophenyl)methylene]amino]-1H-indazol-5-yl]-3,5-pyridinedicarbonitrile |
| 127 | -NH-CH₂-C₆H₄-NO₂ | H | (DMSO-D6, 400 MHz): δ = 2.00 (s, 6H), 4.40 (s, 1H), 4.60 (d, 2H), 6.87 (t, 1H), 7.17 (dd, 1H), 7.24 (d, 1H), 7.59 (s, 1H), 7.64 (d, 2H), 8.15 (d, 2H), 9.43 (s, 1H), 11.44 (s, 1H) ppm | 1,4-dihydro-2,6-dimethyl-4-[3-[[(4-nitrophenyl)methyl]amino]-1H-indazol-5-yl]-3,5-pyridinedicarbonitrile |
| 128 | -NH-CH₂-C₆H₄-NH₂ | H | (DMSO-D6, 400 MHz): δ = 2.00 (s, 6H), 4.23 (d, 2H), 4.35 (s, 1H), 4.87 (s, 2H), 6.25 (t, 1H), 6.48 (d, 2H), 7.04 (d, 2H), 7.12 (d, 1H), 7.20 (d, 1H), 7.60 (s, 1H), 9.43 (s, 1H), 11.40 (s, 1H) ppm | 4-[3-[[(4-aminophenyl)methyl]amino]-1H-indazol-5-yl]-1,4-dihydro-2,6-dimethyl-3,5-pyridinedicarbonitrile |
| 129 | -NH-C(=O)-C₆H₅ | H | | N-[5-(3,5-dicyano-1,4-dihydro-2,6-dimethyl-4-pyridinyl)-1H-indazol-3-yl]-benzamide |
| 130 | -CH₂-N(piperazinyl)-4-pyridinyl | H | (DMSO-D6, 400 MHz): δ = 12.9 (s, 1H), 9.48 (s, 1H), 8.1 (d, 2H), 7.78 (s, 1H), 7.5 (d, 1H), 7.28 (d, 1H), 6.67 (d, 2H), 4.48 (s, 1H), 3.9 (s, 2H), 2.01 (s, 6H) ppm | 1,4-dihydro-2,6-dimethyl-4-[3-[[4-(4-pyridinyl)-1-piperazinyl]methyl]-1H-indazol-5-yl]-3,5-pyridinedicarbonitrile |
| 131 | -NH-CH₂-(4-piperidinyl-NBoc) | H | (DMSO-D6, 400 MHz): δ = 1.00 (m, 2H), 1.35 (s, 9H), 1.72 (d, 2H), 1.83 (m, 1H), 2.00 (s, 6H), 2.65 (m, 2H), 3.10 (m, 2H), 3.90 (m, 2H), 4.36 (s, 1H), 6.03 (t, 1H), 7.10 (d, 1H), 7.20 (d, 1H), 7.55 (s, 1H), 9.45 (s, 1H), 11.35 (s, 1H) ppm | 4-[[[5-(3,5-dicyano-1,4-dihydro-2,6-dimethyl-4-pyridinyl)-1H-indazol-3-yl]amino]methyl]-1-piperidinecarboxylic acid 1,1-dimethylethyl ester |
| 132 | -NH-CH₂-(4-piperidinyl-NBoc) | -CH₂-(4-piperidinyl-NBoc) | (DMSO-D6, 400 MHz): δ = 1.40 (m, 4H), 1.63 (m, 2H), 1.90 (m, 3H), 2.00 (s, 6H), 2.10 (m, 1H), 2.80 (m, 4H), 3.20 (m, 6H), 4.03 (d, 2H), 4.36 (s, 1H), 7.20 (d, 1H), 7.37 (d, 1H), 7.55 (s, 1H), 8.48 (m, 1H), 8.60 (m, 1H), 8.80 (m, 2H), 9.60 (s, 1H) ppm | 4-[[5-(3,5-dicyano-1,4-dihydro-2,6-dimethyl-4-pyridinyl)-3-[[[1-[(1,1-dimethylethoxy)carbonyl]-4-piperidinyl]methyl]amino]-1H-indazol-1-yl]methyl]-1-piperidinecarboxylic acid 1,1-dimethylethyl ester |

TABLE 2-continued

[Structure: 1H-indazole with R12 on N1, R11 on C3, and C5 connected to a 1,4-dihydro-2,6-dimethyl-3,5-dicyano-pyridin-4-yl group]

| Cpd No. | R11 | R12 | 1H NMR | Name |
|---|---|---|---|---|
| 133 | [piperidin-4-ylmethyl-NH-] | H | (DMSO-D6, 400 MHz): δ = 1.03 (m, 2H), 1.70 (m, 3H), 2.00 (s, 6H), 2.40 (d, 2H), 2.92 (d, 2H), 3.09 (m, 2H), 4.36 (s, 1H), 6.00 (t, 1H), 7.10 (d, 1H), 7.20 (d, 1H), 7.55 (s, 1H), 9.45 (s, 1H), 11.35 (s, 1H) ppm | 1,4-dihydro-2,6-dimethyl-4-[3-[(4-piperidinylmethyl)amino]-1H-indazol-5-yl]-3,5-pyridinedicarbonitrile |
| 134 | [piperidin-4-ylmethyl-NH-] | [piperidin-4-ylmethyl-NH-] | (DMSO-D6, 400 MHz): δ = 1.40 (m, 4H), 1.63 (m, 2H), 1.90 (m, 3H), 2.00 (s, 6H), 2.10 (m, 1H), 2.80 (m, 4H), 3.20 (m, 6H), 4.03 (d, 2H), 4.36 (s, 1H), 7.20 (d, 1H), 7.37 (d, 1H), 7.55 (s, 1H), 8.48 (m, 1H), 8.60 (m, 1H), 8.80 (m, 2H), 9.60 (s, 1H) ppm | 1,4-dihydro-2,6-dimethyl-4-[1-(4-piperidinylmethyl)-3-[(4-piperidinylmethyl)amino]-1H-indazol-5-yl]-3,5-pyridinedicarbonitrile tetrahydrochloride |
| 135 | [4-(CO2Me)benzyl-NH-] | H | (DMSO-D6, 400 MHz): δ = 2.00 (s, 6H), 3.80 (s, 3H), 4.38 (s, 1H), 4.50 (d, 2H), 6.75 (t, 1H), 7.15 (d, 1H), 7.24 (d, 1H), 7.48 (d, 2H), 7.60 (s, 1H), 7.88 D, 2H), 9.44 (s, 1H), 11.42 (s, 1H) ppm | 4-[[[5-(3,5-dicyano-1,4-dihydro-2,6-dimethyl-4-pyridinyl)-1H-indazol-3-yl]amino]methyl]-benzoic acid methyl ester |
| 136 | [4-(CO2H)benzyl-NH-] | H | (DMSO-D6, 400 MHz): δ = 2.00 (s, 6H), 4.39 (s, 1H), 4.50 (d, 2H), 6.72 (t, 1H), 7.14 (d, 1H), 7.22 (d, 1H), 7.48 (d, 2H), 7.20 (s, 1H), 7.70 (d, 2H), 9.45 (s, 1H), 12.74 (br s, 1H) ppm | 4-[[[5-(3,5-dicyano-1,4-dihydro-2,6-dimethyl-4-pyridinyl)-1H-indazol-3-yl]amino]methyl]-benzoic acid |
| 137 | [6-(4-methylpiperazin-1-yl)pyridin-3-yl] | H | (DMSO-D6, 400 MHz): δ = 9.51 (s, 1H), 8.68 (s, 1H), 8.05 (d, 1H), 7.81 (s, 1H), 7.59 (d, 1H), 7.32 (d, 1H), 6.98 (d, 1H), 4.6 (s, 1H), 3.67 (m, 4H), 2.41 (m, 4H), 2.02 (s, 6H) ppm | 1,4-dihydro-2,6-dimethyl-4-[3-[6-(4-methyl-1-piperazinyl)-3-pyridinyl]-1H-indazol-5-yl]-3,5-pyridinedicarbonitrile |
| 138 | [4-(dimethylaminomethyl)phenyl] | H | (DMSO-D6, 400 MHz): δ = 9.52 (s, 1H), 7.91 (m, 3H), 7.62 (d, 1H), 7.41 (d, 2H), 7.37 (d, 1H), 4.59 (s, 1H), 3.43 (s, 2H), 2.18 (s, 6H), 2.03 (s, 6H) ppm | 4-[3-[4-[(dimethylamino)methyl]phenyl]-1H-indazol-5-yl]-1,4-dihydro-2,6-dimethyl-3,5-pyridinedicarbonitrile |
| 139 | [3-(dimethylamino)prop-1-ynyl] | H | (DMSO-D6, 400 MHz): δ = 9.52 (br. s, 1H), 7.61 (d, 1H), 7.55 (s, 1H), 7.38 (d, 1H), 4.57 (s, 1H), 3.6 (s, 2H), 2.3 (s, 6H), 2.06 (s, 6H) ppm | 4-[3-[3-(dimethylamino)-1-propynyl]-1H-indazol-5-yl]-1,4-dihydro-2,6-dimethyl-3,5-pyridinedicarbonitrile |

TABLE 2-continued

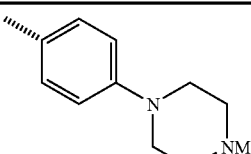

| Cpd No. | R[11] | R[12] | 1H NMR | Name |
|---|---|---|---|---|
| 140 | 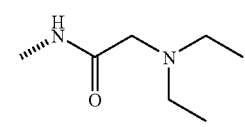 | H | (DMSO-D6, 400 MHz): δ = 13.2 (s, 1H), 9.5 (s, 1H), 7.78 (m, 3H), 7.56 (d, 1H), 7.38 (d, 1H), 7.04 (d, 2H), 4.52 (s, 1H), 3.2 (m, 4H), 2.43 (m, 4H), 2.22 (s, 3H), 2.01 (s, 6H) ppm | 1,4-dihydro-2,6-dimethyl-4-[3-[4-(4-methyl-1-piperazinyl)phenyl]-1H-indazol-5-yl]-3,5-pyridinedicarbonitrile |
| 141 | 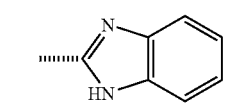 | H | (DMSO-D6, 400 MHz): δ = 9.55 (s, 1H), 7.68 (s, 1H), 7.46 (d, 1H), 7.26 (d, 1H), 4.42 (s, 1H), 3.16 (d, 2H), 2.68 (brs, 4H), 2.03 (s, 6H), 1.08 (t, 6H) ppm | N-[5-(3,5-dicyano-1,4-dihydro-2,6-dimethyl-4-pyridinyl)-1H-indazol-3-yl]-2-(diethylamino)-acetamide |
| 142 | 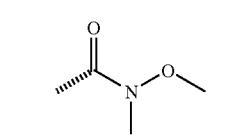 | H | (DMSO-D6, 400 MHz): δ = 8.41 (s, 1H), 7.65 (m, 3H), 7.44 (d, 1H), 7.26 (m, 2H), 4.61 (s, 1H), 2.17 (s, 6H) ppm | 4-[3-(1H-benzimidazol-2-yl)-1H-indazol-5-yl]-1,4-dihydro-2,6-dimethyl-3,5-pyridinedicarbonitrile |
| 143 |  | H | (DMSO-D6, 400 MHz): δ = 9.65 (s, 1H), 7.85 (s, 1H), 7.65 (d, 1H), 7.38 (d, 1H), 4.58 (s, 1H), 3.78 (s, 3H), 3.44 (s, 3H), 2.03 (s, 6H) ppm. | 5-(3,5-dicyano-1,4-dihydro-2,6-dimethyl-4-pyridinyl)-N-methoxy-N-methyl-1H-indazole-3-carboxamide |
| 144 | —CH₂OH | H | (DMSO-D6, 400 MHz): δ = 9.55 (s, 1H), 7.68 (s, 1H), 7.52 (d, 1H), 7.26 (d, 1H), 5.24 (t, 1H), 4.78 (d, 2H), 4.55 (s, 1H), 2.03 (s, 6H) ppm | 1,4-dihydro-4-[3-(hydroxymethyl)-1H-indazol-5-yl]-2,6-dimethyl-3,5-pyridinedicarbonitrile |
| 145 | —CHO | H | (DMSO-D6, 400 MHz): δ = 10.18 (s, 1H), 9.58 (s, 1H), 7.98 (d, 1H), 7.76 (d, 1H), 7.46 (d, 1H), 4.65 (s, 1H), 2.03 (s, 6H) ppm. | 4-(3-formyl-1H-indazol-5-yl)-1,4-dihydro-2,6-dimethyl-3,5-pyridinedicarbonitrile |
| 146 | —CH₂NHCH₃ | H | (DMSO-D6, 400 MHz): δ = 9.5 (s, 1H), 7.64 (s, 1H), 7.49 (d, 1H), 7.25 (d, 1H), 4.46 (s, 1H), 3.97 (s, 2H), 2.28 (s, 3H), 2.02 (s, 6H) ppm | 1,4-dihydro-2,6-dimethyl-4-[3-[(methylamino)methyl]-1H-indazol-5-yl]-3,5-pyridinedicarbonitrile |
| 147 | —NHC(O)NHCH₃ | H | (DMSO-D6, 400 MHz): δ = 9.53 (s, 1H), 9.42 (s, 1H), 7.94 (s, 1H), 7.76 (s. br., 1H), 7.39 (d, 1H), 7.23 (d, 1H), 4.38 (s, 1H), 2.76 (d, 3H), 2.02 (s, 6H) ppm | N-[5-(3,5-dicyano-1,4-dihydro-2,6-dimethyl-4-pyridinyl)-1H-indazol-3-yl]-N'-methyl-urea |
| 148 | Cl | H | (DMSO-D6, 400 MHz): δ = 9.57 (s, 1H), 7.60 (d, 1H), 7.48 (d, 1H), 7.41 (d, 1H), 4.59 (s, 1H), 2.06 (s, 6H) ppm | 4-(3-chloro-1H-indazol-5-yl)-1,4-dihydro-2,6-dimethyl-3,5-pyridinedicarbonitrile |

TABLE 2-continued

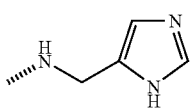

| Cpd No. | R¹¹ | R¹² | 1H NMR | Name |
|---|---|---|---|---|
| 149 | —CH(=NOH) | H | (DMSO-D6, 400 MHz): δ = 11.42 (s, 1H), 9.55 (s, 1H), 8.36 (s, 1H), 7.85 (s, 1H), 7.60 (d, 1H), 7.38 (d, 1H), 4.58 (s, 1H), 2.03 (s, 6H) ppm | 1,4-dihydro-4-[3-[(E)-(hydroxyimino)methyl]-1H-indazol-5-yl]-2,6-dimethyl-3,5-pyridinedicarbonitrile |
| 150 | 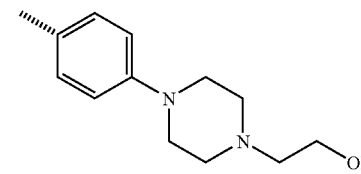 | H | (DMSO-D6, 400 MHz): δ = 2.00 (s, 6H), 4.33 (m, 3H), 6.20 (t, 1H), 6.92 (s, 1H), 7.12 (d, 1H), 7.22 (d, 1H), 7.52 (s, 1H), 7.60 (s, 1H), 9.43 (s, 1H), 11.44 (s, 1H) ppm | 1,4-dihydro-4-[3-[(1H-imidazol-4-ylmethyl)amino]-1H-indazol-5-yl]-2,6-dimethyl-3,5-pyridinedicarbonitrile |
| 151 | Br | H | (DMSO-D6, 400 MHz): δ = 9.56 (s, 1H), 7.63 (d, 1H), 7.42 (m, 2H), 4.59 (s, 1H), 2.04 (s, 6H) ppm | 4-(3-bromo-1H-indazol-5-yl)-1,4-dihydro-2,6-dimethyl-3,5-pyridinedicarbonitrile |
| 152 | 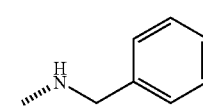 | H | (DMSO-D6, 400 MHz): δ = 7.79 (m, 3H), 7.57 (d, 1H), 7.31 (d, 1H), 7.04 (d, 2H), 4.56 (s, 1H), 3.54 (m, 2H), 3.22 (m, 4H), 2.57 (m, 4H), 2.47 (m, 2H), 2.03 (s, 6H) ppm | 1,4-dihydro-4-[3-[4-[4-(2-hydroxyethyl)-1-piperazinyl]phenyl]-1H-indazol-5-yl]-2,6-dimethyl-3,5-pyridinedicarbonitrile |
| 153 | NH₂ | 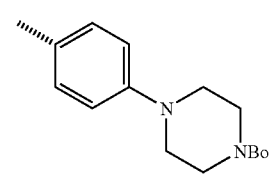 | (DMSO-D6, 400 MHz): δ = 1.58 (s, 9H), 2.00 (s, 6H), 4.20 (s, 1H), 7.08 (dd, 1H), 7.18 (d, 1H), 7.43 (m, 2H), 7.49 (s, 1H) ppm | 4-[3-amino-1-[(4-aminophenyl)methyl]-1H-indazol-5-yl]-1,4-dihydro-2,6-dimethyl-3,5-pyridinedicarbonitrile |
| 154 | —CO₂tBu | H | (DMSO-D6, 400 MHz): δ = 9.58 (s, 1H), 9.47 (s, 1H), 7.65 (s, 1H), 7.54 (d, 1H), 7.46 (d, 1H), 4.51 (s, 1H), 2.02 (s, 6H), 1.45 (s, 9) ppm | 5-(3,5-dicyano-1,4-dihydro-2,6-dimethyl-4-pyridinyl)-1H-indazole-3-carboxylic acid 1,1-dimethylethyl ester |
| 155 | 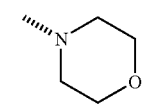 | H | (400 MHz, CDCl3): δ = 7.83 (dd, 2H), 7.51 (d, 1H), 7.37 (d, 1H), 7.08 (d, 2H), 6.22 (s, 1H), 4.48 (s, 1H), 3.6 (m, 4H), 3.22 (m, 4H), 2.14 (s, 6H), 2.17 (s, 9H) ppm | 4-[4-[5-(3,5-dicyano-1,4-dihydro-2,6-dimethyl-4-pyridinyl)-1H-indazol-3-yl]phenyl]-1-piperazinecarboxylic acid 1,1-dimethylethyl ester |
| 156 | | H | (DMSO-D6, 400 MHz): δ = 12.24 (s, 1H), 9.52 (s, 1H), 7.58 (s, 1H), 7.44 (d, 1H), 7.24 (d, 1H), 4.45 (s, 1H), 3.92 (d, 2H), 3.63 (d, 2H), 3.04-3.34 (m, 6), 2.01 (s, 6H), 1.69 (m, 2H), 0.95 (t, 3H) ppm | 1,4-dihydro-2,6-dimethyl-4-[3-(4-morpholinyl)-1H-indazol-5-yl]-3,5-pyridinedicarbonitrile |

TABLE 2-continued

| Cpd No. | R¹¹ | R¹² | 1H NMR | Name |
|---|---|---|---|---|
| 157 | 4-methyl-1-(piperidin-4-yl)-1H-pyrazol-4-yl (structure) | H | (DMSO-D6, 400 MHz): δ = 8.35 (s, 1H), 8.08 (s, 1H), 7.82 (s, 1H), 7.56 (d, 1H), 7.33 (d, 1H), 4.54 (s, 1H), 3.7 (m, 2H), 3.53 (m, 4H), 2.33 (m, 4H), 2.02 (s, 6H) ppm | 1,4-dihydro-2,6-dimethyl-4-[3-[1-(4-piperidinyl)-1H-pyrazol-4-yl]-1H-indazol-5-yl]-3,5-pyridinedicarbonitrile |
| 158 | −C(=O)OMe (structure) | H | (DMSO-D6, 400 MHz): δ = 8.02 (s, 1H), 7.75 (d, 1H), 7.38 (d, 1H), 4.58 (s, 1H), 2.63 (s, 3H), 2.03 (s, 6H) ppm | 4-(3-acetyl-1H-indazol-5-yl)-1,4-dihydro-2,6-dimethyl-3,5-pyridinedicarbonitrile |
| 159 | —CH(=NOMe) | H | (DMSO-D6, 400 MHz): δ = 9.55 (s, 1H), 8.45 (s, 1H), 7.88 (s, 1H), 7.63 (d, 1H), 7.38 (d, 1H), 4.55 (s, 1H), 3.88 (s, 3H), 2.03 (s, 6H) ppm | 1,4-dihydro-4-[3-[(E)-(methoxyimino)methyl]-1H-indazol-5-yl]-2,6-dimethyl-3,5-pyridinedicarbonitrile |
| 160 | =N-OH / Me (hydroxyimino ethyl) | H | (DMSO-D6, 400 MHz): δ = 11.25 (s, 1H), 9.55 (s, 1H), 7.96 (s, 1H), 7.58 (d, 1H), 7.32 (d, 1H), 4.45 (s, 1H), 2.28 (s, 3H), 2.03 (s, 6H) ppm | 1,4-dihydro-4-[3-[(1E)-1-(hydroxyimino)ethyl]-1H-indazol-5-yl]-2,6-dimethyl-3,5-pyridinedicarbonitrile |
| 161 | −NH−CH₂CH₃ HCl Salt | H | (DMSO-D6, 400 MHz): δ = 1.23 (t, 3H), 2.00 (s, 6H), 3.35 (q, 2H), 4.48 (s, 1H), 7.40 (d, 1H), 7.46 (d, 1H), 7.83 (s, 1H), 9.63 (s, 1H), 12.64 (br s, 1H) ppm | 4-[3-(ethylamino)-1H-indazol-5-yl]-1,4-dihydro-2,6-dimethyl-3,5-pyridinedicarbonitrile, hydrochloride salt |
| 162 | −NH−CH₂−(4-morpholinophenyl) | Boc | (DMSO-D6, 400 MHz): δ = 1.60 (s, 9H), 2.03 (s, 6H), 3.03 (m, 4H), 3.66 (m, 4H), 4.40 (d, 2H), 4.48 (s, 1H), 6.90 (d, 2H), 7.28 (d, 1H), 7.43 (d, 1H), 7.81 (s, 1H), 7.87 (d, 1H), 9.57 (s, 1H) ppm | 5-(3,5-dicyano-1,4-dihydro-2,6-dimethyl-4-pyridinyl)-3-[[[4-(4-morpholinyl)phenyl]methyl]amino]-1H-indazole-1-carboxylic acid 1,1-dimethylethyl ester |
| 163 | −NH−CH₂−(4-morpholinophenyl) | H | (DMSO-D6, 400 MHz): δ = 2.00 (s, 6H), 3.00 (m, 4H), 3.68 (m, 4H), 4.33 (m, 3H), 6.40 (t, 1H), 6.85 (d, 2H), 7.13 (d, 1H), 7.22 (d, 1H), 7.36 (d, 2H), 7.60 (s, 1H), 9.43 (s, 1H), 11.42 (s, 1H) ppm | 1,4-dihydro-2,6-dimethyl-4-[3-[[[4-(4-morpholinyl)phenyl]methyl]amino]-1H-indazol-5-yl]-3,5-pyridinedicarbonitrile |

TABLE 2-continued

| Cpd No. | R[11] | R[12] | 1H NMR | Name |
|---|---|---|---|---|
| 164 | piperazinyl | H | (DMSO-D6, 400 MHz): δ = 12.08 (s, 1H), 9.54 (s, 1H), 7.57 (s, 1H), 7.41 (d, 1H), 7.23 (d, 1H), 4.45 (s, 1H), 4.03 (q, 2H), 3.69 (m, 4H), 3.30 (m, 4H), 2.01 (s, 6H), 1.18 (t, 3H) ppm | 1,4-dihydro-2,6-dimethyl-4-[3-(1-piperazinyl)-1H-indazol-5-yl]-3,5-pyridinedicarbonitrile |
| 165.1 | 4-propyl-piperazinyl (TFA salt) | H | (DMSO-D6, 400 MHz): δ = 9.54 (s, 1H), 7.57 (s, 1H), 7.41 (d, 1H), 7.23 (d, 1H), 4.45 (s, 1H), 4.03 (q, 2H), 3.69 (m, 4H), 3.30 (m, 4H), 2.01 (s, 6H), 1.18 (t, 3H) ppm | (AutoNom 2000 name) 2,6-dimethyl-4-[3-(4-propyl-piperazin-1-yl)-1H-indazol-5-yl]-1,4-dihydro-pyridine-3,5-dicarbonitrile, TFA salt |
| 165.2 | 4-propyl-piperazinyl | H |  | (AutoNom 2000 name) 2,6-dimethyl-4-[3-(4-propyl-piperazin-1-yl)-1H-indazol-5-yl]-1,4-dihydro-pyridine-3,5-dicarbonitrile |
| 166 | [4-(2-hydroxyethyl)piperazinyl]methyl | H | (DMSO-D6, 400 MHz): δ = 7.75 (s, 1H), 7.48 (d, 1H), 7.25 (d, 1H), 4.45 (s, 1H), 3.78 (s, 2H), 3.45 (brs, 4H), 2.38 (brs, 8H), 2.03 (s, 6H) ppm | 1,4-dihydro-4-[3-[[4-(2-hydroxyethyl)-1-piperazinyl]methyl]-1H-indazol-5-yl]-2,6-dimethyl-3,5-pyridinedicarbonitrile |
| 167.2 | piperazine-carboxylic acid ethyl ester methyl (TFA salt) | H | (DMSO-D6, 400 MHz): δ = 9.54 (s, 1H), 7.57 (s, 1H), 7.41 (d, 1H), 7.23 (d, 1H), 4.45 (s, 1H), 4.03 (q, 2H), 3.69 (m, 4H), 3.30 (m, 4H), 2.01 (s, 6H), 1.18 (t, 3H) ppm | (AutoNom 2000 name) 4-[5-(3,5-dicyano-2,6-dimethyl-1,4-dihydro-pyridin-4-yl)-1H-indazol-3-ylmethyl]-piperazine-1-carboxylic acid ethyl ester TFA salt |
| 167.2 | piperazine-carboxylic acid ethyl ester methyl | H | (DMSO-D6, 400 MHz): δ = 9.54 (s, 1H), 7.57 (s, 1H), 7.41 (d, 1H), 7.23 (d, 1H), 4.45 (s, 1H), 4.03 (q, 2H), 3.69 (m, 4H), 3.30 (m, 4H), 2.01 (s, 6H), 1.18 (t, 3H) ppm | (AutoNom 2000 name) 4-[5-(3,5-dicyano-2,6-dimethyl-1,4-dihydro-pyridin-4-yl)-1H-indazol-3-ylmethyl]-piperazine-1-carboxylic acid ethyl ester |
| 168 | [4-(3-hydroxypyrrolidinyl)carbonyl]phenyl methylamino | H | (DMSO-D6, 400 MHz): δ = 1.80 (m, 1H), 1.90 (m, 1H), 2.00 (s, 6H), 3.20 (d, 0.5H), 3.40 (m, 1H), 3.50 (m, 2.5H), 4.20 (s, 0.5H), 4.30 (s, 0.5H), 4.50 (s, 1H), 4.60 (s, 1H), 7.50 (m, 6H), 7.90 (s, 1H), 9.52 (s, 1H) ppm | 1,4-dihydro-4-[3-[[[4-[(3-hydroxy-1-pyrrolidinyl)carbonyl]phenyl]methyl]amino]-1H-indazol-5-yl]-2,6-dimethyl-3,5-pyridinedicarbonitrile |
| 169 | $CF_3$ | H | (DMSO-D6, 400 MHz): δ = 9.55 (s, 1H), 7.76 (d, 1H), 7.62 (s, 1H), 7.48 (d, 1H), 4.65 (s, 1H), 2.03 (s, 6H) ppm | 1,4-dihydro-2,6-dimethyl-4-[3-(trifluoromethyl)-1H-indazol-5-yl]-3,5-pyridinedicarbonitrile |

TABLE 2-continued

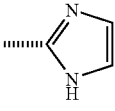

| Cpd No. | R¹¹ | R¹² | 1H NMR | Name |
|---|---|---|---|---|
| 170 | 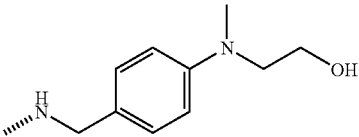 | H | (DMSO-D6, 400 MHz): δ = 9.51 (s, 1H), 8.22 (s, 1H), 7.63 (s, 1H), 7.56 (d, 1H), 7.33 (d, 1H), 7.18 (m, 2H), 4.57 (s, 1H), 2.02 (s, 6H) ppm | 1,4-dihydro-4-[3-(1H-imidazol-2-yl)-1H-indazol-5-yl]-2,6-dimethyl-3,5-pyridinedicarbonitrile |
| 171 | 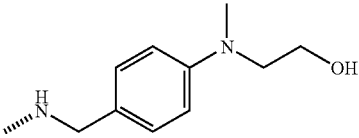 | Boc | (DMSO-D6, 400 MHz): δ = 1.58 (s, 9H), 2.00 (s, 6H), 2.84 (s, 3H), 3.34 (t, 2H), 3.50 (m, 2H), 4.35 (d, 2H), 4.46 (s, 1H), 4.58 (t, 1H), 6.63 (d, 2H), 7.20 (m, 3H), 7.42 (d, 1H), 7.80 (s, 1H), 7.88 (d, 1H), 9.50 (s, 1H) ppm | 5-(3,5-dicyano-1,4-dihydro-2,6-dimethyl-4-pyridinyl)-3-[[[4-[(2-hydroxyethyl)methylamino]phenyl]methyl]amino]-1H-indazole-1-carboxylic acid 1,1-dimethylethyl ester |
| 172 | 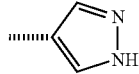 | H | (DMSO-D6, 400 MHz): δ = 2.00 (s, 6H), 2.86 (s, 3H), 3.40 (m, 2H), 3.50 (m, 2H), 4.28 (d, 2H), 4.33 (s, 1H), 4.55 (t, 1H), 6.30 (t, 1H), 6.60 (d, 2H), 7.12 (d, 2H), 7.20 (m, 3H), 7.58 (s, 1H), 9.44 (s, 1H), 11.42 (s, 1H) ppm | 1,4-dihydro-4-[3-[[[4-[(2-hydroxyethyl)methylamino]phenyl]methyl]amino]-1H-indazol-5-yl]-2,6-dimethyl-3,5-pyridinedicarbonitrile |
| 173 | 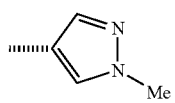 | H | (DMSO-D6, 400 MHz): δ = 9.52 (s, 1H), 8.34 (s, 1H), 7.93 (s, 1H), 7.8 (s, 1H), 7.57 (d, 1H), 7.33 (d, 1H), 4.57 (s, 1H), 2.01 (s, 6H) ppm | 1,4-dihydro-2,6-dimethyl-4-[3-(1H-pyrazol-4-yl)-1H-indazol-5-yl]-3,5-pyridinedicarbonitrile |
| 174 | 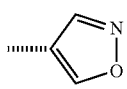 | H | (DMSO-D6, 400 MHz): δ = 9.5 (s, 1H), 8.32 (s, 1H), 7.96 (s, 1H), 7.84 (s, 1H), 7.56 (d, 1H), 7.31 (d, 1H), 4.55 (s, 1H), 3.92 (s, 3H), 2.01 (s, 6H) ppm | 1,4-dihydro-2,6-dimethyl-4-[3-(1-methyl-1H-pyrazol-4-yl)-1H-indazol-5-yl]-3,5-pyridinedicarbonitrile |
| 175 | 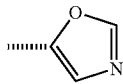 | H | (DMSO-D6, 400 MHz): δ = 9.58 (s, 1H), 9.08 (s, 1H), 8.06 (s, 1H), 7.70 (d, 1H), 7.45 (d, 1H), 6.72 (s, 1H), 4.65 (s, 1H), 2.08 (s, 6H) ppm | 1,4-dihydro-4-[3-(3-isoxazolyl)-1H-indazol-5-yl]-2,6-dimethyl-3,5-pyridinedicarbonitrile |
| 176 | —OH | H | (DMSO-D6, 400 MHz): δ = 2.00 (s, 6H), 4.41 (s, 1H), 7.20 (d, 1H), 7.26 (d, 1H), 7.43 (s, 1H), 9.48 (s, 1H), 10.57 (br s, 1H), 11.42 (br s, 1H) ppm | 1,4-dihydro-4-(3-hydroxy-1H-indazol-5-yl)-2,6-dimethyl-3,5-pyridinedicarbonitrile |
| 177 |  | H | (DMSO-D6, 400 MHz): δ = 8.55 (s, 1H), 7.86 (s, 1H), 7.75 (s, 1H), 7.65 (d, 1H), 7.38 (d, 1H), 4.60 (s, 1H), 2.03 (s, 6H) ppm | 1,4-dihydro-2,6-dimethyl-4-[3-(5-oxazolyl)-1H-indazol-5-yl]-3,5-pyridinedicarbonitrile |

TABLE 2-continued

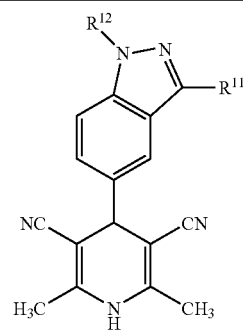

| Cpd No. | R11 | R12 | 1H NMR | Name |
|---|---|---|---|---|
| 178 | (2-thienyl) | H | (DMSO-D6, 400 MHz): δ = 9.55 (s, 1H), 7.92 (s, 1H), 7.68 (d, 1H), 7.60 (d, 1H), 7.58 (d, 1H), 7.38 (d, 1H), 7.20 (d, 1H), 4.65 (s, 1H), 2.03 (s, 6H). | 1,4-dihydro-2,6-dimethyl-4-[3-(2-thienyl)-1H-indazol-5-yl]-3,5-pyridinedicarbonitrile |
| 179 | —NH(iPr) | H |  | 1,4-dihydro-2,6-dimethyl-4-[3-[(1-methylethyl)amino]-1H-indazol-5-yl]-3,5-pyridinedicarbonitrile |

TABLE 3

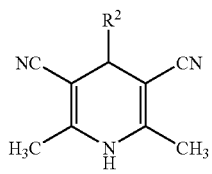

| Cpd No. | R2 | 1H NMR | Name |
|---|---|---|---|
| 180 | MeO2C-pyridinyl | (DMSO-D6, 400 MHz): δ = 2.05 (s, 6H), 3.90 (s, 3H), 4.76 (s, 1H), 8.17-8.18 (t, 1H), 8.78 (d, 1H), 9.05 (d, 1H), 9.68 (s, 1H) ppm. | 3',5'-dicyano-1',4'-dihydro-2',6'-dimethyl-[3,4'-bipyridine]-5-carboxylic acid, methyl ester |
| 181 | thiophene-CO2Me | (DMSO-D6, 400 MHz): δ = 2.04 (s, 6H), 3.80 (s, 3H), 4.88 (s, 1H), 7.08-7.09 (d, 1H), 7.70-7.71 (d, 1H), 9.76 (s, 1H) ppm | 5-(3,5-dicyano-1,4-dihydro-2,6-dimethyl-4-pyridinyl)-2-thiophenecarboxylic acid, methyl ester |
| 182 | furan-CO2Et | (DMSO-D6, 400 MHz): δ = 1.24-1.28 (t, 3H), 2.03 (s, 6H), 4.20-4.26 (dd, 2H), 4.69 (s, 1H), 6.60 (s, 1H), 8.37-8.38 (d, 1H) ppm | 5-(3,5-dicyano-1,4-dihydro-2,6-dimethyl-4-pyridinyl)-3-furancarboxylic acid, ethyl ester |
| 183 | piperidine-N-Boc | (DMSO-D6, 400 MHz): δ = 9.51 (s, 1H), 3.89 (m, 2H), 3.12 (m, 1H), 2.48 (m, 2H), 2.06 (s, 6H), 1.65 (m, 2H), 1.36 (s, 9H), 1.25 (m, 3H) ppm | 3-(3,5-dicyano-1,4-dihydro-2,6-dimethyl-4-pyridinyl)-1-piperidinecarboxylic acid, 1,1-dimethylethyl ester |

TABLE 3-continued

| Cpd No. | R² | 1H NMR | Name |
|---|---|---|---|
| 184 | (piperidine N-CO-OMe, 3-substituted) | (DMSO-D6, 400 MHz): δ = 9.50 (m, 1H), 3.92 (m, 2H), 3.68 (m, 1H), 3.44 (m, 1H), 3.35 (s, 1H), 3.18 (m, 1H), 2.64 (m, 2H), 2.01 (m, 6H), 1.68 (m, 2H), 1.38 (m, 1H), 1.30 (m, 2H) ppm | 3-(3,5-dicyano-1,4-dihydro-2,6-dimethyl-4-pyridinyl)-1-piperidinecarboxylic acid, methyl ester |
| 185 | 2-methyl-3-(methoxycarbonyl)furan-5-yl | (DMSO-D6, 400 MHz): δ = 2.04 (s, 6H), 2.40 (s, 3H), 3.80 (s, 3H), 4.60 (s, 1H), 6.45 (s, 1H) ppm | 5-(3,5-dicyano-1,4-dihydro-2,6-dimethyl-4-pyridinyl)-2-methyl-3-furancarboxylic acid, methyl ester |
| 186 | 5-(acetyloxymethyl)furan-2-yl | (DMSO-D6, 400 MHz): δ = 9.60 (s, 1H), 6.48 (s, 1H), 6.24 (s, 1H), 5.00 (s, 2H), 4.60 (s, 1H), 2.05 (m, 9H) ppm | 4-[5-[(acetyloxy)methyl]-2-furanyl]-1,4-dihydro-2,6-dimethyl-3,5-pyridinedicarbonitrile |
| 187 | 2-methyl-3-(N-methylcarboxamido)furan-5-yl | (DMSO-D6, 400 MHz): δ = 2.03 (s, 6H), 2.48 (s, 3H), 2.67 (d, 3H), 4.55 (s, 1H), 6.60 (s, 1H), 7.94 (dd, 1H), 9.61 (s, 1H) ppm. | 5-(3,5-dicyano-1,4-dihydro-2,6-dimethyl-4-pyridinyl)-N,2-dimethyl-3-furancarboxamide |
| 188 | 1H-1,2,3-benzotriazol-5-yl | (DMSO-D6, 400 MHz): δ = 7.05 (d, 1H), 7.76 (s, 1H), 7.47 (d, 1H), 4.6 (s, 1H), 2.09 (s, 6H) ppm | 4-(1H-1,2,3-benzotriazol-5-yl)-1,4-dihydro-2,6-dimethyl-3,5-pyridinedicarbonitrile |
| 189 | 6-(N-methylcarboxamido)pyridin-2-yl | (DMSO-D6, 400 MHz): δ = 9.64 (s, 1H), 8.41 (m, 1H), 8.09 (m, 1H), 7.96 (m, 1H), 7.60 (m, 1H), 4.65 (s, 1H), 2.87 (d, 3H), 2.07 (s, 6H) ppm | 3',5'-dicyano-1',4'-dihydro-N,2',6'-trimethyl-[2,4'-bipyridine]-6-carboxamide |
| 190 | 6-(N-(pyridin-3-yl)carboxamido)pyridin-2-yl | (DMSO-D6, 400 MHz): δ = 10.44 (s, 1H), 9.75 (s, 1H), 8.94 (m, 1H), 8.34 (m, 1H), 8.26 (m, 1H), 8.14 (m, 1H), 8.07 (m, 1H), 7.66 (m, 1H), 7.40 (m, 1H), 4.76 (s, 1H), 2.04 (s, 6H) ppm | 3',5'-dicyano-1',4'-dihydro-2',6'-dimethyl-N-3-pyridinyl-[2,4'-bipyridine]-6-carboxamide |

TABLE 3-continued

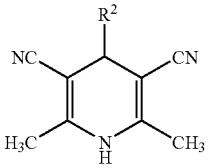

| Cpd No. | R² | 1H NMR | Name |
|---|---|---|---|
| 191 | 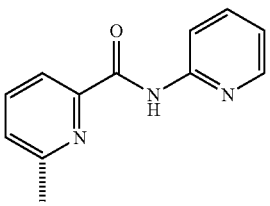 | (DMSO-D6, 400 MHz): δ = 9.69 (s, 1H), 8.54 (m, 1H), 8.10 (m, 1H), 7.95 (m, 1H), 7.62 (m, 2H), 7.20 (m, 1H), 6.88 (m, 1H), 4.67 (s, 1H), 4.01 (m, 2H), 3.30 (m, 2H), 2.07 (s, 6H), 1.97 (m, 2H) ppm | 3',5'-dicyano-1',4'-dihydro-N-[3-(1H-imidazol-1-yl)propyl]-2',6'-dimethyl-[2,4'-bipyridine]-6-carboxamide |
| 192 | 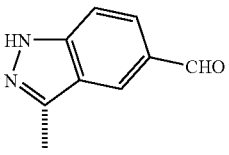 | (DMSO-D6, 400 MHz): δ = 10.37 (s, 1H), 9.74 (s, 1H), 8.41 (m, 1H), 8.31 (m, 1H), 8.19 (m, 2H), 7.90 (m, 1H), 7.73 (m, 1H), 7.22 (m, 1H), 4.80 (s, 1H), 2.11 (s, 3H) ppm | 3',5'-dicyano-1',4'-dihydro-2',6'-dimethyl-N-2-pyridinyl-[2,4'-bipyridine]-6-carboxamide |
| 193 | 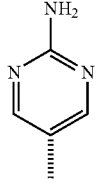 | (DMSO-D6, 400 MHz): δ = 9.97 (s, 1H), 9.74 (s, 1H), 8.22 (s, 1H), 7.82 (d, 2H), 7.66 (d, 2H), 5.05 (s, 1H), 2.03 (s, 6H) ppm | 4-(5-formyl-1H-indazol-3-yl)-1,4-dihydro-2,6-dimethyl-3,5-pyridinedicarbonitrile |
| 194 | 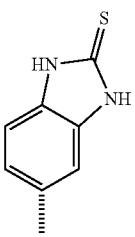 | (DMSO-D6, 400 MHz): δ = 9.51 (s, 1H), 8.11 (s, 2H), 6.74 (s, 2H), 4.28 (s, 1H), 2.01 (s, 6H) ppm | 4-(2-amino-5-pyrimidinyl)-1,4-dihydro-2,6-dimethyl-3,5-pyridinedicarbonitrile |
| 195 | 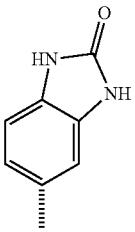 | (DMSO-D6, 400 MHz): δ = 9.64 (s, 1H), 7.53 (s, 1H), 7.36 (d, 1H), 7.32 (d, 1H), 4.61 (s, 1H), 2.10 (s, 6H) ppm | 4-(2,3-dihydro-2-thioxo-6-benzoxazolyl)-1,4-dihydro-2,6-dimethyl-3,5-pyridinedicarbonitrile |
| 196 |  | (DMSO-D6, 400 MHz): δ = 11.64 (s, 1H), 9.51 (s, 1H), 7.18 (s, 1H), 7.08 (d, 1H), 7.03 (d, 1H), 4.40 (s, 1H), 2.01 (s, 6H) ppm | 4-(2,3-dihydro-2-oxo-6-benzoxazolyl)-1,4-dihydro-2,6-dimethyl-3,5-pyridinedicarbonitrile |

TABLE 3-continued

| Cpd No. | R² | 1H NMR | Name |
|---|---|---|---|
| 197 | 2-amino-benzoxazol-6-yl | (DMSO-D6, 400 MHz): δ = 9.46 (s, 1H), 7.40 (s, 2H), 7.19 (s, 1H), 7.17 (d, 1H), 6.98 (d, 1H), 4.39 (s, 1H), 2.02 (s, 6H) ppm | 4-(2-amino-6-benzoxazolyl)-1,4-dihydro-2,6-dimethyl-3,5-pyridinedicarbonitrile |
| 198 | 3-amino-1H-indazol-6-yl | (DMSO-D6, 400 MHz): δ = 11.37 (s, 1H), 9.49 (s, 1H), 7.64 (d, 1H), 7.03 (s, 1H), 6.82 (d, 1H), 5.32 (s, 2H), 4.42 (s, 1H), 2.02 (s, 6H) ppm | 4-(3-amino-1H-indazol-6-yl)-1,4-dihydro-2,6-dimethyl-3,5-pyridinedicarbonitrile |
| 199 | 4-(1H-pyrazol-5-yl)-2-thienyl | (DMSO-D6, 400 MHz): δ = 2.05 (s, 6H), 4.79 (s, 1H), 6.56-6.57 (d, 1H), 7.32 (s, 1H), 7.70 (br s, 2H), 9.66 (s, 1H) ppm | 1,4-dihydro-2,6-dimethyl-4-[4-(1H-pyrazol-5-yl)-2-thienyl]-3,5-pyridinedicarbonitrile |
| 200 | 4-(1H-pyrazol-5-yl)-2-furanyl | (DMSO-D6, 400 MHz): δ = 2.04 (s, 6H), 4.63 (s, 1H), 6.45-6.46 (d, 1H), 6.63 (s, 1H), 7.64 (d, 1H), 8.0 (d, 1H) ppm | 1,4-dihydro-2,6-dimethyl-4-[4-(1H-pyrazol-5-yl)-2-furanyl]-3,5-pyridinedicarbonitrile |
| 201 | 4-(3-pyridinyl)-2-furanyl | (DMSO-D6, 400 MHz): δ = 2.05 (s, 6H), 4.64 (s, 1H), 6.89 (s, 1H), 7.38-7.42 (m, 1H), 7.98-8.01 (dt, 1H), 8.29 (d, 1H), 8.44-8.46 (dd, 1H), 8.86 (d, 1H) ppm | 1,4-dihydro-2,6-dimethyl-4-[4-(3-pyridinyl)-2-furanyl]-3,5-pyridinedicarbonitrile |
| 202 | 1H-indazol-6-yl | (DMSO-D6, 400 MHz): δ = 9.57 (s, 1H), 8.05 (s, 1H), 7.77 (d, 1H), 7.36 (s, 1H), 7.05 (d, 1H), 4.53 (s, 1H), 2.02 (s, 6H) ppm | 1,4-dihydro-4-(1H-indazol-6-yl)-2,6-dimethyl-3,5-pyridinedicarbonitrile |

TABLE 3-continued

[Structure: 4-R² substituted 1,4-dihydro-2,6-dimethyl-3,5-pyridinedicarbonitrile core]

| Cpd No. | R² | 1H NMR | Name |
|---|---|---|---|
| 203 | 1H-pyrazolo[4,3-b]pyridin-5-yl | (DMSO-D6, 400 MHz): δ = 9.6 (s, 1H), 8.33 (s, 1H), 8.02 (d, 1H), 7.37 (d, 1H), 4.63 (s, 1H), 2.0 (s, 6H) ppm | 1,4-dihydro-2,6-dimethyl-4-(1H-pyrazolo[4,3-b]pyridin-5-yl)-3,5-pyridinedicarbonitrile |
| 204 | 1H-pyrazolo[3,4-b]pyridin-5-yl | (DMSO-D6, 400 MHz): δ = 8.48 (m, 1H), 8.18 (s, 1H), 8.14 (s, 1H), 4.67 (s, 1H), 4.09 (s, 1H), 2.06 (s, 6H) ppm | 1,4-dihydro-2,6-dimethyl-4-(1H-pyrazolo[3,4-b]pyridin-5-yl)-3,5-pyridinedicarbonitrile |
| 205 | 3-amino-2-NBoc-2H-indazol-5-yl | (DMSO-D6, 400 MHz): δ = 1.58 (s, 9H), 2.00 (s, 6H), 4.20 (s, 1H), 7.08 (dd, 1H), 7.18 (d, 1H), 7.43 (m, 2H), 7.49 (s, 1H) ppm | 3-amino-5-(3,5-dicyano-1,4-dihydro-2,6-dimethyl-4-pyridinyl)-2H-indazole-2-carboxylic acid, 1,1-dimethylethyl ester |
| 206 | 1H-pyrazolo[3,4-c]pyridin-5-yl | (DMSO-D6, 400 MHz): δ = 9.42 (s, 1H), 9.04 (s, 1H), 8.21 (s, 1H), 7.64 (s, 1H), 4.61 (s, 1H), 2.0 (s, 6H) ppm | 1,4-dihydro-2,6-dimethyl-4-(1H-pyrazolo[3,4-c]pyridin-5-yl)-3,5-pyridinedicarbonitrile |

TABLE 4

[Structure: phenyl ring with R at position 1 and R¹¹ substituent]

| Cpd No. | R | R¹¹ | 1H NMR | Name |
|---|---|---|---|---|
| 207 | 4-(3,5-dicyano-1,4-dihydro-2-methyl-6-phenyl-pyridin-4-yl) | 4, —OH and 3, —Cl | (DMSO-D6, 400 MHz): δ = 10.33 (s, 1H), 9.70 (s, 1H) 7.51 (m, 5H), 7.27 (s, 1H), 7.13 (d, 1H), 6.99 (d, 1H), 4.49 (s, 1H), 2.07 (s, 6H) ppm | 4-(3-chloro-4-hydroxyphenyl)-1,4-dihydro-2-methyl-6-phenyl-3,5-pyridinedicarbonitrile |

TABLE 4-continued

| Cpd No. | R | R¹¹ | 1H NMR | Name |
|---|---|---|---|---|
| 208 | (3,5-dicyano-1,4-dihydro-6-methyl-2-tert-butyl pyridinyl) | 4, —OH and 3, —Cl | (DMSO-D6, 400 MHz): δ = 10.26 (s, 1H), 8.24 (s, 1H), 7.15 (s, 1H), 7.00 (m, 2H), 4.24 (s, 1H), 2.11 (s, 3H), 1.32 (s, 9H) ppm | 4-(3-chloro-4-hydroxyphenyl)-2-(1,1-dimethylethyl)-1,4-dihydro-6-methyl-3,5-pyridinedicarbonitrile |
| 209 | (3,5-dicyano-1,4-dihydro-6-methyl-2-furanyl pyridinyl) | 4, —OH and 3, —Cl | (DMSO-D6, 400 MHz): δ = 10.31 (s, 1H), 9.58 (s, 1H), 7.96 (s, 1H), 7.24 (m, 2H), 7.11 (d, 1H), 6.99 (d, 1H), 6.73 (m, 1H), 4.47 (s, 1H), 2.16 (s, 3H) ppm | 4-(3-chloro-4-hydroxyphenyl)-2-(2-furanyl)-1,4-dihydro-6-methyl-3,5-pyridinedicarbonitrile |
| 210 | (3,5-dicyano-1,4-dihydro-6-methyl-2-phenyl pyridinyl) | 4, —OH | (DMSO-D6, 400 MHz): δ = 9.67 (s, 1H), 9.48 (s, 1H), 7.54 (m, 5H), 7.15 (d, 2H), 6.80 (d, 2H), 4.41 (s, 1H), 2.08 (s, 3H) ppm | 1,4-dihydro-4-(4-hydroxyphenyl)-2-methyl-6-phenyl-3,5-pyridinedicarbonitrile |
| 211 | (3,5-dicyano-1,4-dihydro-6-methyl-2-(2-chlorophenyl) pyridinyl) | 4, —OH | (DMSO-D6, 400 MHz): δ = 9.83 (s, 1H), 9.50 (s, 1H), 7.55 (m, 4H), 7.20 (d, 2H), 6.80 (d, 2H), 4.45 (s, 1H), 2.04 (s, 3H) ppm | 2-(2-chlorophenyl)-1,4-dihydro-4-(4-hydroxyphenyl)-6-methyl-3,5-pyridinedicarbonitrile |
| 212 | (3-cyano-1,4-dihydro-2-methyl-6-trifluoromethyl pyridinyl) | 4, —OH and 3, —Cl | (DMSO-D6, 400 MHz): δ = 10.20 (s, 1H), 9.29 (s, 1H), 7.16 (s, 1H), 7.03 (d, 1H), 6.97 (d, 1H), 5.34 (m, 1H), 4.36 (m, 1H), 2.06 (s, 3H) ppm | 4-(3-chloro-4-hydroxyphenyl)-1,4-dihydro-2-methyl-6-(trifluoromethyl)-3-pyridinecarbonitrile |
| 213 | (3,5-dicyano-1,4-dihydro-6-methyl-2-(4-methoxycarbonylphenyl) pyridinyl) | 4, —OH and 3, —Cl | (DMSO-D6, 400 MHz): δ = 10.32 (s, 1H), 9.84 (s, 1H), 8.09 (d, 2H), 7.71 (d, 2H), 7.32 (s, 1H), 7.17 (d, 1H), 7.03 (d, 1H), 4.54 (s, 1H), 3.89 (s, 3H), 2.11 (s, 3H) ppm | 4-[4-(3-chloro-4-hydroxyphenyl)-3,5-dicyano-1,4-dihydro-6-methyl-2-pyridinyl]-benzoic acid, methyl ester |

TABLE 4-continued

| Cpd No. | R | R[11] | 1H NMR | Name |
|---|---|---|---|---|
| 214 | (3-cyano-2-methyl-6-phenyl-1,4-dihydropyridin-4-yl, with NC, CN, phenyl, CH₃) | 4, —OH | | 1,4-dihydro-4-(4-hydroxyphenyl)-2-methyl-6-phenyl-3,5-pyridinedicarbonitrile |
| 215 | (dihydropyridine with 4-(hydroxymethyl)phenyl substituent) | 4, —OH and 3, —Cl | | 4-(3-chloro-4-hydroxyphenyl)-1,4-dihyro-2-[4-(hydroxymethyl)phenyl]-6-methyl-3,5-pyridinedicarbonitrile |
| 216 | (dihydropyridine with 2-chlorophenyl substituent) | 4, —OH | | 2-(2-chlorophenyl)-1,4-dihydro-4-(4-hydroxyphenyl)-6-methyl-3,5-pyridinecarbonitrile |
| 217 | (dihydropyridine with CF₃ and CH₃, single CN) | 4, —OH and 3, —Cl | | 4-(3-chloro-4-hydroxyphenyl)-1,4-dihydro-2-methyl-6-(trifluoromethyl)-3-pyridinecarbonitrile |
| 218 | (dihydropyridine with 3-hydroxyphenyl substituent) | 4, —OH and 3, —Cl | (DMSO-D6, 400 MHz): δ = 10.29 (s, 1H), 9.82 (s, 1H) 9.67 (s, 1H), 7.27 (m, 2H), 7.15 (m, 1H), 7.02 (m, 1H), 6.91 (m, 3H), 4.48 (s, 1H), 2.08 (s, 3H) ppm | 4-(3-chloro-4-hydroxyphenyl)-1,4-dihydro-2-(3-hydroxyphenyl)-6-methyl-3,5-pyridinedicarbonitrile |
| 219 | (dihydropyridine with phenyl substituent) | 3, —CO₂CH₃ | (DMSO-D6, 400 MHz): δ = 9.84 (s, 1H), 7.97 (m, 2H), 7.71 (m, 1H), 7.64 (m, 1H), 7.56 (m, 5H), 4.78 (s, 1H), 3.88 (s, 3H), 2.12 (s, 3H) ppm | 3-(3,5-dicyano-1,4-dihydro-2-methyl-6-phenyl-4-pyridinyl)-benzoic acid, methyl ester |

TABLE 4-continued

| Cpd No. | R | R¹¹ | 1H NMR | Name |
|---|---|---|---|---|
| 220 | (furan with 2,5-dimethyl and CF3, attached to dihydropyridine dicarbonitrile with methyl) | 4, —OBn and 3, —Cl | (DMSO-D6, 400 MHz): δ = 10.34 (s, 1H), 9.92 (s, 1H) 7.26 (s, 1H), 7.09 (d, 1H), 6.99 (d, 1H), 6.62 (s, 1H), 4.52 (s, 1H), 2.40 (s, 3H), 2.04 (s, 3H) ppm | 4-(3-chloro-4-hydroxyphenyl)-1,4-dihydro-2-methyl-6-[2-methyl-5-(trifluoromethyl)-3-furanyl]-3,5-pyridinedicarbonitrile |
| 221 | (5-methyl-3-furanyl dihydropyridine dicarbonitrile) | 4, —OH and 3, —Cl | (DMSO-D6, 400 MHz): δ = 10.31 (s, 1H), 9.57 (s, 1H), 7.66 (d, 1H), 7.26 (s, 1H), 7.14 (d, 1H), 7.02 (d, 1H), 6.59 (d, 1H), 4.47 (s, 1H), 2.26 (s, 3H), 2.07 (s, 3H) ppm | 4-(3-chloro-4-hydroxyphenyl)-1,4-dihydro-2-methyl-6-(5-methyl-3-furanyl)-3,5-pyridinedicarbonitrile |
| 222 | (4-chlorophenyl dihydropyridine dicarbonitrile) | 4, —OH and 3, —Cl | (DMSO-D6, 400 MHz): δ = 10.31 (s, 1H), 9.76 (s, 1H), 7.58 (m, 4H), 7.30 (s, 1H), 7.17 (d, 1H), 7.02 (d, 1H), 4.52 (s, 1H), 2.09 (s, 3H) ppm | 4-(3-chloro-4-hydroxyphenyl)-2-(4-chlorophenyl)-1,4-dihydro-6-methyl-3,5-pyridinedicarbonitrile |
| 223 | (2-thienyl dihydropyridine dicarbonitrile) | 4, —OH and 3, —Cl | (DMSO-D6, 400 MHz): δ = 10.30 (s, 1H), 9.62 (s, 1H), 7.82 (m, 1H), 7.54 (m, 1H), 7.24 (s, 1H), 7.19 (m, 1H), 7.08 (d, 1H), 6.98 (d, 1H), 4.47 (s, 1H), 2.09 (s, 3H) ppm | 4-(3-chloro-4-hydroxyphenyl)-1,4-dihydro-2-methyl-6-(2-thienyl)-3,5-pyridinedicarbonitrile |
| 224 | (3-pyridyl dihydropyridine dicarbonitrile) | 4, —OH and 3, —Cl | (DMSO-D6, 400 MHz): δ = 10.29 (s, 1H), 9.83 (s, 1H), 8.72 (m, 2H), 7.96 (m, 1H), 7.53 (m, 1H), 7.31 (s, 1H), 7.15 (d, 1H), 7.00 (d, 1H), 4.53 (s, 1H), 2.07 (s, 3H) ppm | 4-(3-chloro-4-hydroxyphenyl)-1,4-dihydro-6-methyl-[2,3'-bipyridine]-3,5-dicarbonitrile |
| 225 | (2,6-dimethylpyridine dicarbonitrile) | 4, —SH | Remove??? | 4-(4-mercaptophenyl)-2,6-dimethyl-3,5-pyridinedicarbonitrile |

TABLE 4-continued

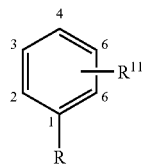

| Cpd No. | R | R[11] | 1H NMR | Name |
|---|---|---|---|---|
| 226 | (piperidin-3-yl, NH) attached to dihydropyridine with NC, CN, CH3 | 3, —CO2CH3 | (DMSO-D6, 400 MHz): δ = [Mixture of diastereomers]10.88 (s, 0.5H), 10.72 (s, 0.5H), 9.88 (s, 0.5H), 9.65 (s, 0.5H), 9.61 (s, 0.5H), 8.28 (s, 0.5H), 7.93 (m, 1H), 7.89 (m, 1H), 7.60 (m, 2H), 5.05 (s, 0.5H), 4.56 (s, 0.5H), 3.83 (m, 3H), 3.61 (m, 1H), 3.25 (m, 3H), 2.69 (m, 0.5H), 2.56 (m, 0.5H), 2.09 (s, 1.5H), 2.05 (s, 1.5H), 1.95 (m, 1H), 1.75 (m, 2H), 1.45 (m, 1H) ppm | |
| 227 | (N-Boc piperidin-3-yl) attached to dihydropyridine with NC, CN, CH3 | 3, —CO2CH3 | (DMSO-D6, 400 MHz): δ = 9.16 (m, 1H), 7.91 (m, 1H), 7.83 (m, 1H), 7.59 (m, 2H), 4.61 (s, 1H), 3.92 (m, 4H), 3.85 (s, 3H), 3.21 (m, 1H), 2.50 m, 2H), 2.09 (m, 3H), 1.71 (m, 2H), 1.38 (m, 9H) ppm | 3-[3,5-dicyano-1,4-dihydro-4-[3-(methoxycarbonyl)phenyl]-6-methyl-2-pyridinyl]-1-piperidinecarboxylic acid, 1,1-dimethylethyl ester |
| 228 | (biphenyl) attached to dihydropyridine with NC, CN, CH3 | 4, —OH and 3, —Cl | (DMSO-D6, 400 MHz): δ = 10.29 (s, 1H), 9.75 (s, 1H), 7.81 (m, 2H), 7.71 (m, 2H), 7.61 (m, 2H), 7.48 (m, 2H), 7.29 (s, 1H), 7.14 (d, 1H), 7.01 (m, 1H), 4.51 (s, 1H), 2.09 (s, 3H) ppm | 2-[1,1'-biphenyl]-4-yl-4-(3-chloro-4-hydroxyphenyl)-1,4-dihydro-6-methyl-3,5-pyridinedicarbonitrile |
| 229 | (N-Ac piperidin-3-yl) attached to dihydropyridine with NC, CN, CH3 | 3, —CO2CH3 | (DMSO-D6, 400 MHz): δ = 9.19 (s, 1H), 7.94 (m, 1H), 7.86 (m, 1H), 7.59 (m, 2H), 4.63 (m, 1H), 4.41 (m, 1H), 3.87 (s, 3H), 3.85 (m, 1H), 3.37 (m, 1H), 2.85 (m, 1H), 2.51 (m, 1H), 2.09 (s, 3H), 2.01 (s, 3H), 1.95 (m, 1H), 1.79 (m, 2H), 1.47 (m, 1H) ppm | 3-[2-(1-acetyl-3-piperidinyl)-3,5-dicyano-1,4-dihydro-6-methyl-4-pyridinyl]-benzoic acid, methyl ester. |

TABLE 4-continued

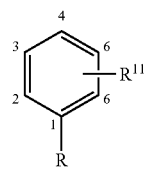

| Cpd No. | R | R11 | 1H NMR | Name |
|---|---|---|---|---|
| 230 | (piperidine with N-C(=O)NH2, connected via 3-position to dihydropyridine with 2 CN, Me, NH) | 3, —CO2CH3 | (DMSO-D6, 400 MHz): δ = 9.18 (m, 1H), 7.93 (m, 1H), 7.86 (m, 1H), 7.59 (m, 2H), 6.05 (s, 2H), 4.61 (s, 1H), 3.90 (m, 2H), 3.87 (s, 3H), 2.98 (m, 1H), 2.61 (m, 2H), 2.09 (m, 3H), 1.88 (m, 1H), 1.76 (m, 2H), 1.35 (m, 1H). | 3-[2-[1-(aminocarbonyl)-3-piperidinyl]-3,5-dicyano-1,4-dihydro-6-methyl-4-pyridinyl]-benzoic acid, methyl ester |
| 231 | (phthalimide-CH(Me)- attached to dihydropyridine) | 3, —CO2CH3 | (DMSO-D6, 400 MHz): δ = 9.08 (m, 1H), 7.85 (m, 6H), 7.56 (m, 2H), 5.10 (m, 1H), 4.61 (s, 1H), 3.84 (s, 3H), 2.09 (s, 3H), 1.76 (m, 3H) ppm | 3-[3,5-dicyano-2-[1-(1,3-dihydro-1,3-dioxo-2H-isoindol-2-yl)ethyl]-1,4-dihydro-6-methyl-4-pyridinyl]-benzoic acid, methyl ester |
| 232 | (3-nitrophenyl-dihydropyridine) | 3, —CO2CH3 | (DMSO-D6, 400 MHz): δ = 8.40 (m, 2H), 8.05 (m, 2H), 7.95 (m, 1H), 7.70 (m, 1H), 7.55 (m, 2H), 6.30 (s, 1H), 4.60 (s, 1H), 3.92 (s, 3H), 2.25 (s, 3H) ppm | 3-[3,5-dicyano-1,4-dihydro-2-methyl-6-(3-nitrophenyl)-4-pyridinyl]-benzoic acid, methyl ester |
| 233 | (4-nitrophenyl-dihydropyridine) | 3, —CO2CH3 | (DMSO-D6, 400 MHz): δ = 10.02 (s, 1H), 8.39 (m, 2H), 7.97 (m, 2H), 7.87 (m, 2H), 7.75 (m, 1H), 7.66 (m, 1H), 4.84 (s, 1H), 3.89 (s, 3H), 2.13 (s, 3H) ppm | 3-[3,5-dicyano-1,4-dihydro-2-methyl-6-(4-nitrophenyl)-4-pyridinyl]-benzoic acid, methyl ester |
| 234 | (4-hydroxyphenyl-dihydropyridine) | 3, —CO2CH3 | (DMSO-D6, 400 MHz): δ = 10.05 (s, 1H), 9.68 (s, 1H), 7.95 (m, 2H), 7.66 (m, 1H), 7.61 (m, 1H), 7.38 (d, 2H), 6.87 (d, 2H), 4.71 (s, 1H), 3.87 (s, 3H), 2.11 (s, 3H) ppm | 3-[3,5-dicyano-1,4-dihydro-2-(4-hydroxyphenyl)-6-methyl-4-pyridinyl]-benzoic acid, methyl ester |

TABLE 4-continued

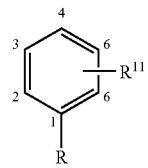

| Cpd No. | R | R[11] | 1H NMR | Name |
|---|---|---|---|---|
| 235 | (structure: 2-(3-aminophenyl)-3,5-dicyano-6-methyl-1,4-dihydropyridine) | 3, —CO₂CH₃ | (DMSO-D6, 400 MHz): δ = 9.74 (s, 1H), 7.96 (m, 2H), 7.65 (m, 2H), 7.14 (m, 1H), 6.70 (m, 2H), 6.61 (m, 1H), 5.40 (s, 2H), 4.71 (s, 1H), 3.88 (s, 3H), 2.09 (s, 3H) ppm | 3-[2-(3-aminophenyl)-3,5-dicyano-1,4-dihydro-6-methyl-4-pyridinyl]-benzoic acid, methyl ester |
| 236 | (structure: 2-(4-aminophenyl)-3,5-dicyano-6-methyl-1,4-dihydropyridine) | 3, —CO₂CH₃ | (DMSO-D6, 400 MHz): δ = 9.55 (s, 1H), 7.93 (m, 2H), 7.63 (m, 2H), 7.22 (m, 2H), 6.60 (m, 2H), 5.70 (s, 2H), 4.65 (s, 1H), 3.87 (s, 3H), 2.11 (s, 3H) ppm | 3-[2-(4-aminophenyl)-3,5-dicyano-1,4-dihydro-6-methyl-4-pyridinyl]-benzoic acid, methyl ester |
| 237 | (structure: 2-(3-aminophenyl)-3,5-dicyano-6-methyl-1,4-dihydropyridine) | 3, —C(O)NHCH₃ | (DMSO-D6, 400 MHz): δ = 9.70 (s, 1H), 8.52 (m, 1H), 7.78 (m, 2H), 7.50 (m, 2H), 7.13 (m, 1H), 6.69 (m, 2H), 6.63 (m, 1H), 5.38 (s, 2H), 4.60 (s, 1H), 2.79 (d, 3H), 2.09 (s, 3H) ppm | 3-[2-(3-aminophenyl)-3,5-dicyano-1,4-dihydro-6-methyl-4-pyridinyl]-N-methyl-benzamide |
| 238 | (structure: 2-(4-aminophenyl)-3,5-dicyano-6-methyl-1,4-dihydropyridine) | 3, —C(O)NHCH₃ | (DMSO-D6, 400 MHz): δ = 9.51 (s, 1H), 8.50 (m, 1H), 7.78 (m, 2H), 7.50 (m, 2H), 7.23 (m, 2H), 6.60 (m, 2H), 5.68 (s, 2H), 4.54 (s, 1H), 2.79 (d, 3H), 2.11 (s, 3H) ppm | 3-[2-(4-aminophenyl)-3,5-dicyano-1,4-dihydro-6-methyl-4-pyridinyl]-N-methyl-benzamide |
| 239 | (structure: 2-(4-hydroxyphenyl)-3,5-dicyano-6-methyl-1,4-dihydropyridine) | 3, —C(O)NHCH₃ | (DMSO-D6, 400 MHz): δ = 9.64 (s, 1H), 8.50 (m, 1H), 7.78 (m, 2H), 7.50 (m, 2H), 7.38 (m, 2H), 6.86 (m, 2H), 4.59 (s, 1H), 3.17 (s, 1H), 2.79 (d, 3H), 2.09 (s, 3H) ppm | 3-[3,5-dicyano-1,4-dihydro-2-(4-hydroxyphenyl)-6-methyl-4-pyridinyl]-N-methyl-benzamide |
| 240 | (structure: 2-phenyl-3,5-dicyano-6-methyl-1,4-dihydropyridine) | 3, —C(O)NHCH₃ | (DMSO-D6, 400 MHz): δ = 9.60 (s, 1H), 8.50 (m, 1H), 7.78 (m, 1H), 7.50 (m, 8H), 4.64 (s, 1H), 2.79 (d, 3H), 2.09 (s, 3H) ppm | 3-(3,5-dicyano-1,4-dihydro-2-methyl-6-phenyl-4-pyridinyl)-N-methyl-benzamide |

TABLE 4-continued

| Cpd No. | R | R[11] | 1H NMR | Name |
|---|---|---|---|---|
| 241 | (structure: 2-(3-NHAc-phenyl)-3,5-dicyano-6-methyl-1,4-dihydropyridine) | 3, —C(O)NHCH₃ | (DMSO-D6, 400 MHz): δ = 10.16 (s, 1H), 9.81 (s, 1H), 8.53 (m, 1H), 7.80 (m, 3H), 7.70 (m, 1H), 7.53 (m, 2H), 7.44 (m, 1H), 7.18 (m, 1H), 4.66 (s, 1H), 2.79 (m, 3H), 2.11 (s, 3H), 2.05 (s, 3H) ppm | 3-[2-[3-(acetylamino)phenyl]-3,5-dicyano-1,4-dihydro-6-methyl-4-pyridinyl]-N-methyl-benzamide |
| 242 | (structure: 2-(3-NHSO₂Me-phenyl)-3,5-dicyano-6-methyl-1,4-dihydropyridine) | 3, —C(O)NHCH₃ | (DMSO-D6, 400 MHz): δ = 10.28 (s, 1H), 9.83 (s, 1H), 8.52 (m, 1H), 7.81 (m, 2H), 7.51 (m, 3H), 7.33 (m, 2H), 7.25 (m, 1H), 4.68 (s, 1H), 3.03 (s, 3H), 2.79 (m, 3H), 2.11 (s, 3H) ppm | 3-[3,5-dicyano-1,4-dihydro-2-methyl-6-[3-[(methylsulfonyl)amino]phenyl]-4-pyridinyl]-N-methyl-benzamide |
| 243 | (structure: 2-(3-NH(CO)NH₂-phenyl)-3,5-dicyano-6-methyl-1,4-dihydropyridine) | 3, —C(O)NHCH₃ | (DMSO-D6, 400 MHz): δ = 9.78 (s, 1H), 8.78 (s, 1H), 8.52 (m, 1H), 7.81 (m, 2H), 7.58 (m, 4H), 7.35 (m, 1H), 7.05 (m, 1H), 5.91 (s, 2H), 4.65 (s, 1H), 2.80 (m, 3H), 2.11 (s, 3H) ppm | 3-[2-[3-[(aminocarbonyl)amino]phenyl]-3,5-dicyano-1,4-dihydro-6-methyl-4-pyridinyl]-N-methyl-benzamide |
| 244 | (structure: 2-(2-CbzNH-ethyl)-3,5-dicyano-6-methyl-1,4-dihydropyridine) | 3, —C(O)NHCH₃ | (DMSO-D6, 400 MHz): δ = 2.04 (s, 3H), 2.45-2.50 (m, 2H), 2.75-2.80 (d, 4H), 3.25-3.32 (m, 2H), 4.42 (s, 1H), 4.90-5.10 (m, 2H), 7.28-7.36 (m, 6H), 7.42-7.48 (m, 3H), 7.70-7.72 (s, 1H), 7.74-7.78 (dt, 1H), 8.44-8.48 (bt, 1H), 9.50 (bs, 1H) ppm | [2-[3,5-dicyano-1,4-dihydro-6-methyl-4-[3-[(methylamino)carbonyl]phenyl]-2-pyridinyl]ethyl]-carbamic acid, phenylmethyl ester |
| 245 | (structure: 2-(3-NH₂-phenyl)-3,5-dicyano-6-methyl-1,4-dihydropyridine) | 3-, CH₃C(O)NH-CH₂CH₂CH₂-OEt | (DMSO-D6, 400 MHz): δ = 9.71 (s, 1H), 8.54 (t, 1H), 7.80 (m, 2H), 7.53 (m, 2H), 7.13 (m, 1H), 6.70 (m, 2H), 6.61 (m, 1H), 5.39 (m, 2H), 4.61 (s, 1H), 3.42 (m, 4H), 3.30 (m, 2H), 2.09 (s, 3H), 1.77 (m, 2H), 1.10 (t, 3H) ppm | 3-[2-(3-aminophenyl)-3,5-dicyano-1,4-dihydro-6-methyl-4-pyridinyl]-N-(3-ethoxypropyl)-benzamide |

TABLE 4-continued

| Cpd No. | R | R¹¹ | 1H NMR | Name |
|---|---|---|---|---|
| 246 | 2-(3-aminophenyl)-3,5-dicyano-6-methyl-1,4-dihydropyridin-4-yl | 3-, -NHC(O)CH₃ with propyl-imidazole (3-acetamidopropyl imidazole) | (DMSO-D6, 400 MHz): δ = 9.71 (s, 1H), 8.61 (m, 1H), 7.81 (m, 2H), 7.66 (s, 1H), 7.52 (m, 2H), 7.21 (s, 1H), 7.13 (m, 1H), 6.89 (s, 1H), 6.70 (m, 2H), 6.62 (m, 1H), 5.39 (s, 2H), 4.62 (s, 1H), 4.03 (t, 2H), 3.24 (m, 2H), 2.11 (s, 3H), 1.95 (m, 2H) ppm | 3-[2-(3-aminophenyl)-3,5-dicyano-1,4-dihydro-6-methyl-4-pyridinyl]-N-[3-(1H-imidazol-1-yl)propyl]-benzamide |
| 247 | 2-(2-aminoethyl)-3,5-dicyano-6-methyl-1,4-dihydropyridin-4-yl | 3, —C(O)NHCH₃ | (DMSO-D6, 400 MHz): δ = 2.13 (s, 3H), 2.77-2.81 (t, 2H), 2.93 (s, 3H), 3.19-3.23 (m, 2H), 4.51 (s, 1H), 7.48-7.50 (m, 2H), 7.75-7.77 (m, 1H), 7.79-7.80 (m, 1H) ppm. | |
| 248 | 2-((1,3-dioxoisoindolin-2-yl)methyl)-3,5-dicyano-6-methyl-1,4-dihydropyridin-4-yl | 4, —OH and 3, —Cl | (DMSO-D6, 400 MHz): δ = 2.00 (s, 1H), 4.37 (s, 1H), 4.45-4.56 (dd, 2H), 6.95-6.97 (d, 1H), 7.06-7.07 (dd, 1H), 7.25-7.26 (d, 1H), 7.89-7.92 (m, 4H), 9.50 (s, 1H), 10.25 (s, 1H) ppm | 4-(3-chloro-4-hydroxyphenyl)-2-[(1,3-dihydro-1,3-dioxo-2H-isoindol-2-yl)methyl]-1,4-dihydro-6-methyl-3,5-pyridinedicarbonitrile |

TABLE 5

| Cpd No. | R⁴ | R⁶ | R¹¹ | R¹² | 1H NMR | Name |
|---|---|---|---|---|---|---|
| 249 | phenyl | —CH₃ | —H | —H | (DMSO-D6, 400 MHz): δ = 13.14 (s, 1H), 9.76 (s, 1H), 8.12 (s, 1H), 7.72 (s, 1H), 7.63 (m, 1H), 7.54 (m, 5H), 7.40 (m, 1H), 4.67 (s, 1H), 2.11 (s, 3H) ppm | 1,4-dihydro-4-(1H-indazol-5-yl)-2-methyl-6-phenyl-3,5-pyridine-dicarbonitrile |

TABLE 5-continued

| Cpd No. | R⁴ | R⁶ | R¹¹ | R¹² | 1H NMR | Name |
|---|---|---|---|---|---|---|
| 250 | 3-nitrophenyl (wedge) | —CH₃ | —H | —H | (DMSO-D6, 400 MHz): δ = 13.14 (s, 1H), 9.93 (s, 1H), 8.43 (m, 2H), 8.12 (s, 1H), 8.06 (m, 1H), 7.85 (m, 1H), 7.79 (s, 1H), 7.63 (m, 1H), 7.45 (m, 1H), 4.72 (s, 1H), 2.11 (s, 3H) ppm | 1,4-dihydro-4-(1H-indazol-5-yl)-2-methyl-6-(3-nitrophenyl)-3,5-pyridine-dicarbonitrile |
| 251 | N-Cbz piperidin-3-yl (wedge) | —CH₃ | —H | —H | (DMSO-D6, 400 MHz): δ = 13.14 (s, 1H), 9.93 (s, 1H), 8.43 (m, 2H), 8.12 (s, 1H), 8.06 (m, 1H), 7.85 (m, 1H), 7.79 (s, 1H), 7.63 (m, 1H), 7.45 (m, 1H), 4.72 (s, 1H), 2.11 (s, 3H) ppm | 3-[3,5-dicyano-1,4-dihydro-4-(1H-indazol-5-yl)-6-methyl-2-pyridinyl]-1-piperidine-carboxylic acid phenylmethyl ester |
| 252 | 3-aminophenyl (wedge) | —CH₃ | —H | —H | (DMSO-D6, 400 MHz): δ = 9.67 (s, 1H), 8.11 (s, 1H), 7.67 (s, 1H), 7.60 (m, 1H), 7.36 (m, 1H), 7.12 (m, 1H), 6.68 (m, 2H), 6.62 (m, 1H), 5.38 (m, 2H), 4.61 (s, 1H), 2.11 (s, 3H) ppm | 2-(3-aminophenyl)-1,4-dihydro-4-(1H-indazol-5-yl)-6-methyl-3,5-pyridine-dicarbonitrile |
| 253 | 3-NHAc-phenyl (wedge) | —CH₃ | —H | —H | (DMSO-D6, 400 MHz): δ = 13.14(s, 1H), 10.15 (s, 1H), 9.76 (s, 1H), 8.12 (s, 1H), 7.78 (m, 1H), 7.70 (m, 2H), 7.61 (m, 1H), 7.43 (m, 2H), 7.19 (m, 1H), 4.66 (s, 1H), 2.11 (s, 3H), 2.05 (s, 3H) ppm | N-[3-[3,5-dicyano-1,4-dihydro-4-(1H-indazol-5-yl)-6-methyl-2-pyridinyl]phenyl]-acetamide |

TABLE 5-continued

| Cpd No. | R⁴ | R⁶ | R¹¹ | R¹² | 1H NMR | Name |
|---|---|---|---|---|---|---|
| 254 | (3-piperidinyl) | —CH₃ | —H | —H | (DMSO-D6, 400 MHz): δ = [Mixture of diastereomers] 10.86 (s, 0.5H), 10.69 (s, 0.5H), 9.89 (s, 0.5H), 9.62 (m, 1H), 8.13 (m, 1H), 7.82 (m, 1H), 7.70 (s, 0.5H), 7.57 (m, 1H), 7.32 (m, 1H), 5.04 (s, 0.5H), 4.57 (s, 0.5H), 3.58 (m, 1H), 3.34 (m, 2H), 3.15 (m, 1H), 2.71 (m, 0.5H), 2.58 (m, 0.5H), 2.12 (s, 1.5H), 2.08 (s, 1.5H), 2.01 (m, 1H), 1.78 (m, 2H), 1.48 (m, 1H) ppm | (AutoNom 2000 name) 4-(1H-indazol-5-yl)-6-methyl-1,4,1',2',3',4',5',6'-octahydro-[2,3']bipyridinyl-3,5-dicarbonitrile |
| 255 | —CH₂CH₂NH₂ | —CH₃ | —H | —H | (DMSO-D6, 400 MHz): δ = 8.09 (s, 1H), 7.60 (m, 1H), 7.55 (m, 1H), 7.29 (m, 1H), 4.50 (s, 1H), 2.80 (m, 2H), 2.43 (m, 2H), 2.04 (s, 3H) ppm | 2-(2-aminoethyl)-1,4-dihydro-4-(1H-indazol-5-yl)-6-methyl-3,5-pyridine-dicarbonitrile |
| 256 | —CH₂CH₂NHAc | —CH₃ | —H | —H | (DMSO-D6, 400 MHz): δ = 13.10 (s, 1H), 9.47 (s, 1H), 8.08 (s, 1H), 8.03 (m, 1H), 7.64 (s, 1H), 7.55 (m, 1H), 7.31 (m, 1H), 4.49 (s, 1H), 3.37 (m, 1H), 3.25 (m, 1H), 2.42 (m, 2H), 2.11 (s, 3H), 1.77 (s, 3H) ppm | N-[2-[3,5-dicyano-1,4-dihydro-4-(1H-indazol-5-yl)-6-methyl-2-pyridinyl]ethyl]-acetamide |
| 257 | 4-(CO₂Me)-phenyl | —CH₃ | —H | —H | (DMSO-D6, 400 MHz): δ = 13.05 (s, 1H), 9.87 (s, 1H), 8.13 (s, 1H), 8.07 (m, 2H), 7.73 (m, 3H), 7.62 (m, 1H), 7.43 (m, 1H), 4.71 (s, 1H), 3.89 (s, 3H), 2.13 (s, 3H) ppm | 4-[3,5-dicyano-1,4-dihydro-4-(1H-indazol-5-yl)-6-methyl-2-pyridinyl]-benzoic acid methyl ester |

TABLE 5-continued

| Cpd No. | R⁴ | R⁶ | R¹¹ | R¹² | 1H NMR | Name |
|---|---|---|---|---|---|---|
| 258 | 4-(hydroxymethyl)phenyl | —CH₃ | —H | —H | (DMSO-D6, 400 MHz): δ = 13.12 (s, 1H), 9.72 (s, 1H), 8.11 (s, 1H), 7.71 (s, 1H), 7.62 (m, 1H), 7.52 (m, 2H), 7.40 (m, 3H), 5.33 (m, 2H), 4.65 (s, 1H), 4.56 (m, 2H), 2.11 (s, 3H) ppm | 1,4-dihydro-2-[4-(hydroxy-methyl)phenyl]-4-(1H-indazol-5-yl)-6-methyl-3,5-pyridine-dicarbonitrile |
| 259 | phenyl | —CH₃ | —NH₂ | —H | (DMSO-D6, 400 MHz): δ = 11.46 (s, 1H), 9.71 (s, 1H), 7.64 (s, 1H), 7.54 (m, 5H), 7.27 (m, 2H), 5.42 (s, 2H), 4.54 (s, 1H), 2.11 (s, 3H) ppm | 4-(3-amino-1H-indazol-5-yl)-1,4-dihydro-2-methyl-6-phenyl-3,5-pyridine-dicarbonitrile |
| 260 | 4-(CO₂H)phenyl | —CH₃ | —NH₂ | —H | (DMSO-D6, 400 MHz): δ = 9.85 (s, 1H), 8.13 (s, 1H), 8.07 (d, 2H), 7.73 (s, 1H), 7.68 (d, 2H), 7.61 (m, 1H), 7.41 (m, 1H), 4.70 (s, 1H), 3.17 (s, 1H), 2.12 (s, 3H) ppm | 4-[3,5-dicyano-1,4-dihydro-4-(1H-indazol-5-yl)-6-methyl-2-pyridinyl]-benzoic acid |
| 261 | 4-[C(O)NH-CH₂CH₂-morpholinyl]phenyl | —CH₃ | —H | —CH₃ | (DMSO-D6, 400 MHz): δ = 13.1 (s, 1H), 9.82 (s, 1H), 8.57 (m, 1H), 8.12 (s, 1H), 7.95 (d, 2H), 7.73 (s, 1H), 7.64 (m, 3H), 7.41 (m, 1H), 4.69 (s, 1H), 3.56 (m, 4H), 3.40 (m, 4H), 2.41 (m, 4H), 2.11 (s, 3H) ppm | 4-[3,5-dicyano-1,4-dihydro-4-(1H-indazol-5-yl)-6-methyl-2-pyridinyl]-N-[2-(4-morpholinyl)ethyl]-benzamide |
| 264 | 4-chlorophenyl | —CH₃ | —NH₂ | —H | (DMSO-D6, 400 MHz): δ = 11.45 (s, 1H), 9.75 (s, 1H), 7.60 (m, 5H), 7.25 (m, 2H), 5.41 (s, 2H), 4.55 (s, 1H), 2.11 (s, 3H) ppm | 4-(3-amino-1H-indazol-5-yl)-2-(4-chlorophenyl)-1,4-dihydro-6-methyl-3,5-pyridine-dicarbonitrile |

TABLE 5-continued

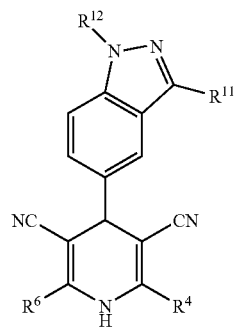

| Cpd No. | $R^4$ | $R^6$ | $R^{11}$ | $R^{12}$ | 1H NMR | Name |
|---|---|---|---|---|---|---|
| 265 | 4-pyridyl | —CH₃ | —H | —H | (DMSO-D6, 400 MHz): δ = 9.84 (s, 1H), 8.76 (d, 2H), 8.12 (s, 1H), 7.72 (s, 1H), 7.58 (m, 3H), 7.40 (d, 1H), 4.69 (s, 1H), 2.09 (s, 3H) ppm | 1,4-dihydro-4-(1H-indazol-5-yl)-6-methyl-[2,4'-bipyridine]-3,5-dicarbonitrile |
| 266 | 3-pyridyl | —CH₃ | —H | —H | (DMSO-D6, 400 MHz): δ = 9.90 (s, 1H), 8.78 (d, 2H), 8.11 (s, 1H), 8.00 (d, 1H), 7.74 (s, 1H), 7.61 (d, 1H), 7.56 (d, 1H), 7.43 (d, 1H), 4.72 (s, 1H), 2.10 (s, 3H) ppm | 1,4-dihydro-4-(1H-indazol-5-yl)-6-methyl-[2,3'-bipyridine]-3,5-dicarbonitrile |
| 267 | 2-furanyl | —CH₃ | —H | —H | (DMSO-D6, 400 MHz): δ = 9.59 (s, 1H), 8.08 (s, 1H), 7.95 (s, 1H), 7.65 (s, 1H), 7.57 (d, 1H), 7.33 (d, 1H), 7.21 (s, 1H), 6.71 (s, 1H), 4.61 (s, 1H), 2.14 (s, 3H) ppm | 2-(2-furanyl)-1,4-dihydro-4-(1H-indazol-5-yl)-6-methyl-3,5-pyridine-dicarbonitrile |
| 268 | —CO₂CH₃ | —CH₃ | —H | —H | (DMSO-D6, 400 MHz): δ = 13.15 (s, 1H), 9.70 (s, 1H), 8.10 (s, 1H), 7.65 (s, 1H), 7.55 (d, 1H), 7.30 (d, 1H), 4.67 (s, 1H), 4.30 (m, 2H), 2.11 (s, 3H), 1.27 (t, 3H) ppm | 3,5-dicyano-1,4-dihydro-4-(1H-indazol-5-yl)-6-methyl-2-pyridine-carboxylic acid ethyl ester |
| 269 | —CH₂CH₃ | —CH₂CH₃ | —H | —H | (DMSO-D6, 400 MHz): δ = 9.39 (s, 1H), 8.05 (s, 1H), 7.58 (s, 1H), 7.55 (d, 1H), 7.24 (d, 1H), 4.48 (s, 1H), 2.34 (q, 4H), 1.17 (t, 6H) ppm | 2,6-diethyl-1,4-dihydro-4-(1H-indazol-5-yl)-3,5-pyridine-dicarbonitrile |

TABLE 5-continued

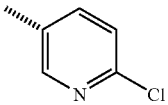

| Cpd No. | R⁴ | R⁶ | R¹¹ | R¹² | 1H NMR | Name |
|---|---|---|---|---|---|---|
| 270 | 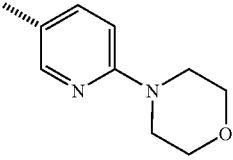 | —CH₃ | —H | —H | (DMSO-D6, 400 MHz): δ = 13.10 (s, 1H), 9.70 (s, 1H), 8.32 (s, 1H), 8.10 (s, 1H), 7.75 (m, 2H), 7.60 (m, 1H), 7.39 (m, 1H), 6.95 (m, 1H), 4.64 (s, 1H), 3.70 (m, 4H), 3.55 (m, 4H), 2.13 (s, 3H) ppm | 1,4-dihydro-2-(4-chloropyrid-3-yl)-6-methyl-4-(1H-indazol-5-yl)-3,5-pyridine-dicarbonitrile |
| 271 | 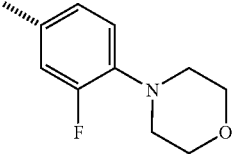 | —CH₃ | —H | —H | (DMSO-D6, 400 MHz): δ = 13.10 (s, 1H), 9.70 (s, 1H), 8.32 (s, 1H), 8.10 (s, 1H), 7.75 (m, 2H), 7.60 (m, 1H), 7.39 (m, 1H), 6.95 (m, 1H), 4.64 (s, 1H), 3.70 (m, 4H), 3.55 (m, 4H), 2.13 (s, 3H) ppm | 1,4-dihydro-4-(1H-indazol-5-yl)-6-methyl-6'-(4-morpholinyl)-[2,3'-bipyridine]-3,5-dicarbonitrile |
| 272 | 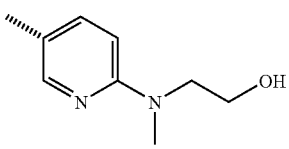 | —CH₃ | —H | —H | (DMSO-D6, 400 MHz): δ = 13.00 (s, 1H), 9.70 (s, 1H), 8.12 (s, 1H), 7.75 (s, 1H), 7.60 (m, 1H), 7.39 (m, 3H), 7.13 (m, 1H), 4.64 (s, 1H), 3.75 (m, 4H), 3.10 (m, 4H), 2.13 (s, 3H) ppm | 2-[3-fluoro-4-(4-morpholinyl) phenyl]-1,4-dihydro-4-(1H-indazol-5-yl)-6-methyl-3,5-pyridine-dicarbonitrile |
| 273 |  | —CH₃ | —H | —H | (DMSO-D6, 400 MHz): δ = 13.10 (s, 1H), 9.62 (s, 1H), 8.29 (s, 1H), 8.10 (s, 1H), 7.75 (s, 1H), 7.60 (m, 2H), 7.39 (m, 1H), 6.78 (m, 1H), 4.78 (t, 1H), 4.60 (s, 1H), 3.60 (m, 4H), 3.10 (s, 3H), 2.13 (s, 3H) ppm | 1,4-dihydro-6'-[(2-hydroxyethyl) methyl-amino]-4-(1H-indazol-5-yl)-6-methyl-[2,3'-bipyridine]-3,5-dicarbonitrile |

TABLE 5-continued

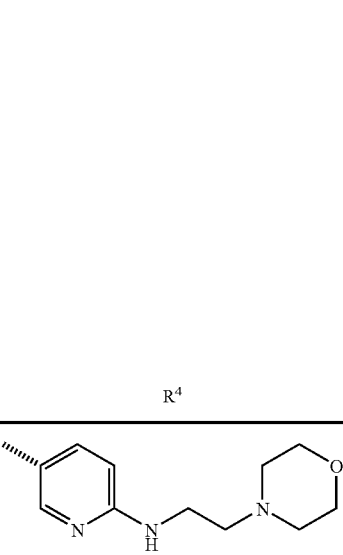

| Cpd No. | R⁴ | R⁶ | R¹¹ | R¹² | 1H NMR | Name |
|---|---|---|---|---|---|---|
| 274 | 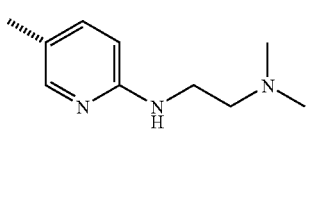 | —CH₃ | —H | —H | (DMSO-D6, 400 MHz): δ = 13.00 (s, 1H), 9.60 (s, 1H), 8.20 (m, 1H), 8.10 (s, 1H), 7.75 (m, 1H), 7.60 (m, 1H), 7.55 (m, 1H), 7.39 (m, 1H), 7.02 (m, 1H), 6.58 (m, 1H), 4.60 (s, 1H), 3.65 (m, 4H), 3.40 (m, 2H), 2.50 (m, 2H), 2.40 (m, 4H), 2.13 (s, 3H) ppm | 1,4-dihydro-4-(1H-indazol-5-yl)-6-methyl-6'-[[2-(4-morpholinyl)ethyl]amino]-[2,3'-bipyridine]-3,5-dicarbonitrile |
| 275 | 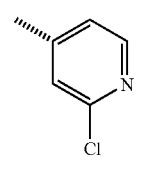 | —CH₃ | —H | —H | (DMSO-D6, 400 MHz): δ = 13.10 (s, 1H), 9.60 (s, 1H), 8.19 (m, 1H), 8.10 (s, 1H), 7.75 (s, 1H), 7.60 (m, 1H), 7.52 (m, 1H), 7.39 (m, 1H), 7.00 (m, 1H), 6.58 (m, 1H), 4.60 (s, 1H), 3.40 (m, 2H), 2.40 (m, 2H), 2.20 (s, 6H), 2.10 (s, 3H) ppm. | 1,4-dihydro-2-[4-(2-dimethylamino)ethylamino-pyrid-3-yl)-6-methyl-4-(1H-indazol-5-yl)-3,5-pyridine-dicarbonitrile |
| 276 | 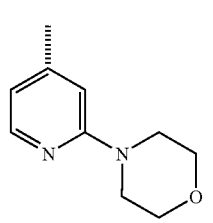 | —CH₃ | —H | —H | (DMSO-D6, 400 MHz): δ = 13.10 (s, 1H), 9.90 (s, 1H), 8.60 (m, 1H), 8.10 (s, 1H), 7.80 (s, 1H), 7.75 (s, 1H), 7.60 (m, 2H), 7.41 (m, 1H), 4.72 (s, 1H), 2.13 (s, 3H) ppm | 2'-chloro-1,4-dihydro-4-(1H-indazol-5-yl)-6-methyl-[2,4'-bipyridine]-3,5-dicarbonitrile |
| 277 |  | —CH₃ | —H | —H | (DMSO-D6, 400 MHz): δ = 13.01 (s, 1H), 9.78 (s, 1H), 8.25 (m, 1H), 8.10 (s, 1H), 7.71 (s, 1H), 7.60 (m, 1H), 7.40 (m, 1H), 6.96 (s, 1H), 6.78 (m, 1H), 4.63 (s, 1H), 3.70 (m, 4H), 3.52 (m, 4H), 2.06 (s, 3H). | 1,4-dihydro-4-(1H-indazol-5-yl)-6-methyl-2'-(4-morpholinyl)-[2,4'-bipyridine]-3,5-dicarbonitrile |

TABLE 5-continued

[Structure: 1H-indazole with R12 on N1, R11 at 3-position, connected at 5-position to a 1,4-dihydropyridine ring bearing two CN groups at 3,5-positions, R4 and R6 at 2,6-positions, NH]

| Cpd No. | R⁴ | R⁶ | R¹¹ | R¹² | 1H NMR | Name |
|---|---|---|---|---|---|---|
| 278 | [4-pyridyl with 2-(2-morpholinylethyl)amino substituent] | —CH₃ | —H | —H | (DMSO-D6, 400 MHz): δ = 13.10 (s, 1H), 9.78 (s, 1H), 8.17 (d, 1H), 8.11 (m, 1H), 7.70 (m, 1H), 7.60 (m, 1H), 7.39 (m, 1H), 7.18 (m, 1H), 6.72 (m, 1H), 6.68 (m, 1H), 4.65 (s, 1H), 3.80 (m, 4H), 3.60 (m, 4H), 3.25 (m, 4H), 2.11 (s, 3H) ppm | 1,4-dihydro-4-(1H-indazol-5-yl)-6-methyl-2'-[[2-(4-morpholinyl)ethyl]amino]-[2,4-bipyridine]-3,5-dicarbonitrile |
| 279 | CH₃ | —CH₃ | —NH₂ | (4-NH₂—C₆H₄)CH₂— | (DMSO-D6, 400 MHz): δ = 1.58 (s, 9H), 2.00 (s, 6H), 4.20 (s, 1H), 7.08 (dd, 1H), 7.18 (d, 1H), 7.43 (m, 2H), 7.49 (s, 1H) ppm | 4-[3-amino-1-[(4-aminophenyl)methyl]-1H-indazol-5-yl]-1,4-dihydro-2,6-dimethyl-3,5-pyridine-dicarbonitrile |
| 280 | [4-pyridyl with N-methyl-N-(2-hydroxyethyl)amino substituent] | —CH₃ | —H | —H | (DMSO-D6, 400 MHz): δ = 11.46 (s, 1H), 7.61 (m, 1H), 7.46 (m, 2H), 7.34 (m, 1H), 7.26 (m, 3H), 7.19 (m, 1H), 5.41 (s, 2H), 4.98 (s, 2H), 4.46 (s, 1H), 2.18 (s, 6H) ppm | 1,4-dihydro-2'-[(2-hydroxyethyl)methylamino]-4-(1H-indazol-5-yl)-6-methyl-[2,4'-bipyridine]-3,5-dicarbonitrile |
| 281 | [2,5-dimethyl-3-furanyl] | —CH₃ | —NH₂ | —H | (DMSO-D6, 400 MHz): δ = 11.45 (s, 1H), 9.49 (s, 1H), 7.59 (s, 1H), 7.28 (d, 1H), 7.20 (d, 1H), 6.21 (s, 1H), 5.40 (s, 2H), 4.48 (s, 1H), 2.25 (s, 3H), 2.19 (s, 3H), 2.08 (s, 3H) ppm | 4-(3-amino-1H-indazol-5-yl)-2-(2,5-dimethyl-3-furanyl)-1,4-dihydro-6-methyl-3,5-pyridine-dicarbonitrile |
| 282 | [2-methyl-3-furanyl] | —CH₃ | —NH₂ | —H | (DMSO-D6, 400 MHz): δ = 11.45 (s, 1H), 9.55 (s, 1H), 7.66 (m, 1H), 7.61 (s, 1H), 7.28 (m, 1H), 7.22 (m, 1H), 6.60 (s, 1H), 5.40 (s, 2H), 4.50 (s, 1H), 2.25 (s, 3H), 2.09 (s, 3H) ppm | 4-(3-amino-1H-indazol-5-yl)-1,4-dihydro-2-methyl-6-(2-methyl-3-furanyl)-3,5-pyridine-dicarbonitrile |

TABLE 6

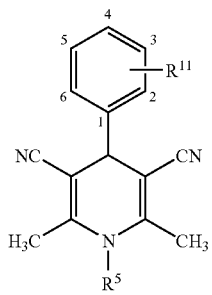

| Cpd No | $R^5$ | $R^{11}$ | 1H NMR | Name |
|---|---|---|---|---|
| 283 | —Bn | 4, —OH and 3, —Br | (DMSO-D6, 400 MHz): δ = 10.33 (s, 1H), 9.50 (s, 1H), 7.52 (m, 2H), 7.34 (s, 1H), 7.21 (m, 3H), 7.08 (d, 1H), 6.96 (d, 1H), 4.34 (s, 1H), 2.03 (s, 6H) ppm | 4-(3-bromo-4-hydroxyphenyl)-1,4-dihydro-2,6-dimethyl-1-(phenylmethyl)-3,5-pyridinedicarbonitrile |
| 284 | —CH$_3$ | 3, —CO$_2$CH$_3$ | (DMSO-D6, 400 MHz): δ = 2.2 (s, 6H), 3.85 (s, 3H), 4.5 (s, 1H), 7.55 (m, 2H), 7.83 (s, 1H), 7.88 (d, 1H), 9.60 (s 1H) ppm | 3-(3,5-dicyano-1,4-dihydro-1,2,6-trimethyl-4-pyridinyl)-benzoic acid, methyl ester |
| 285 | —CH$_3$ | 3, —C(O)NHCH$_3$ | (DMSO-D6, 400 MHz): δ = 2.20 (s, 6H), 2.75 (s, 3H), 4.40 (s, 1H), 7.40 (d, 1H), 7.42 (dd, 1H), 7.64 (s, 1H), 7.73 (d, 1H), 8.44 (q, 1H) ppm | 3-(3,5-dicyano-1,4-dihydro-1,2,6-trimethyl-4-pyridinyl)-N-methyl-benzamide |
| 286 | —Bn | 3, —CN and 4, —F | (DMSO-D6, 400 MHz): δ = 7.86 (dd, 1H), 7.69 (m, 1H), 7.55 (t, 1H), 7.46 (m, 2H), 7.25 (m, 3H), 5.4 (s, 2H), 4.7 (s, 1H), 2.12 (s, 6H) ppm | (AutoNom 2000 name) 1-benzyl-4-(3-cyano-4-fluoro-phenyl)-2,6-dimethyl-1,4-dihydro-pyridine-3,5-dicarbonitrile |
| 287 | —CH$_2$CH$_3$ | 3, —CN and 4, —F | (DMSO-D6, 400 MHz): δ = 7.86 (dd, 1H), 7.69 (m, 1H), 7.55 (t, 1H), 4.57 (s, 1H), 3.12 (q, 2H), 2.1 (s, 6H), 1.4 (t, 3H) ppm | 1-ethyl-4-(3-cyano-4-fluorophenyl)-1,4-dihydro-2,6-dimethyl-3,5-pyridinedicarbonitrile |

TABLE 7

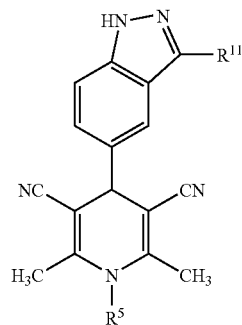

| Cpd No. | $R^5$ | $R^{11}$ | 1H NMR | Name |
|---|---|---|---|---|
| 288 | —CH$_3$ | —NH$_2$ | (DMSO-D6, 400 MHz): δ = 7.47 (s, 1H), 7.21 (d, 1H), 7.16 (d, 1H), 4.25 (s, 1H), 2.11 (s, 6H) ppm | 4-(3-amino-1H-indazol-5-yl)-1,4-dihydro-1,2,6-trimethyl-3,5-pyridinedicarbonitrile |
| 289 | —CH$_3$ | —H | (DMSO-D6, 400 MHz): δ = 8.08 (s, 1H), 7.60 (s, 1H), 7.56 (d, 1H), 7.29 (d, 1H), 4.45 (s, 1H), 3.21 (s, 3H), 2.24 (s, 6H) ppm | 1,4-dihydro-4-(1H-indazol-5-yl)-1,2,6-trimethyl-3,5-pyridinedicarbonitrile |

TABLE 7-continued

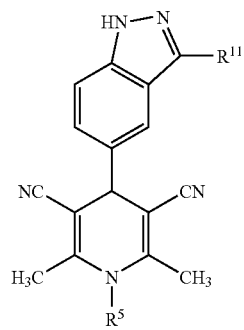

| Cpd No. | R⁵ | R¹¹ | 1H NMR | Name |
|---|---|---|---|---|
| 290 | —CH₂CO₂CH₂CH₃ | —H | (CD3OD, 400 MHz): δ = 8.05 (s, 1H), 7.72 (s, 1H), 7.57 (d, 1H), 7.49 (d, 1H), 4.58 (s, 2H), 4.43 (s, 1H), 4.32 (q, 2H), 2.22 (s, 6H), 1.33 (t, 3H) ppm | 3,5-dicyano-4-(1H-indazol-5-yl)-2,6-dimethyl-1(4H)-pyridineacetic acid ethyl ester |
| 291 | —CH₂COOH | —H | (DMSO-D6, 400 MHz): δ = 9.90 (s, 1H), 8.78 (d, 2H), 8.11 (s, 1H), 8.00 (d, 1H), 7.74 (s, 1H), 7.61 (d, 1H), 7.56 (d, 1H), 7.43 (d, 1H), 4.72 (s, 1H), 2.10 (s, 3H) ppm | 3,5-dicyano-4-(1H-indazol-5-yl)-2,6-dimethyl-1(4H)-pyridineacetic acid |
| 292 | —CH₂CH₂OH | —H | (CD3OD, 400 MHz): δ = 8.04 (s, 1H), 7.69 (s, 1H), 7.55 (d, 1H), 7.44 (d, 1H), 4.38 (s, 1H), 3.84 (m, 2H), 3.72 (t, 2H), 2.32 (s, 6H) ppm | 1,4-dihydro-1-(2-hydroxyethyl)-4-(1H-indazol-5-yl)-2,6-dimethyl-3,5-pyridinedicarbonitrile |
| 293 | —Bn | —NH₂ | (CD3OD, 400 MHz): δ = 8.04 (s, 1H), 7.69 (s, 1H), 7.55 (d, 1H), 7.44 (d, 1H), 4.38 (s, 1H), 3.84 (m, 2H), 3.72 (t, 2H), 2.32 (s, 6H) ppm | 4-(3-amino-1H-indazol-5-yl)-1,4-dihydro-2,6-dimethyl-1-(phenylmethyl)-3,5-pyridinedicarbonitrile |
| 294 | —CH₂CH₃ | —NH₂ | (DMSO-D6, 400 MHz): δ = 11.43 (s, 1H), 7.51 (s, 1H), 7.26 (d, 1H), 7.12 (d, 1H), 5.37 (s, 2H), 4.32 (s, 1H), 3.67 (q, 2H), 2.27 (s, 6H), 1.18 (t, 3H) ppm | 1-ethyl-4-(3-amino-1H-indazol-5-yl)-1,4-dihydro-2,6-dimethyl-3,5-pyridinedicarbonitrile |
| 295 | —Bn | —H | (CD3OD, 400 MHz): δ = 8.13 (s, 1H), 7.67 (s, 1H), 7.62 (d, 1H), 7.48 (m, 2H), 7.37 (m, 2H), 7.26 (d, 2H), 5.01 (s, 2H), 4.61 (s, 1H), 2.22 (s, 6H) ppm | 1,4-dihydro-4-(1H-indazol-5-yl)-2,6-dimethyl-1-(phenylmethyl)-3,5-pyridinedicarbonitrile |
| 296 | —CH₂CO₂CH₂CH₃ | —Cl | (DMSO-D6, 400 MHz): δ = 7.60 (d, 1H), 7.54 (s, 1H), 7.48 (d, 1H), 4.62 (s, 2H), 4.58 (s, 1H), 4.32 (q, 2H), 2.20 (s, 6H), 1.33 (t, 3H) ppm | 4-(3-chloro-1H-indazol-5-yl)-3,5-dicyano-2,6-dimethyl-1(4H)-pyridineacetic acid ethyl ester |
| 297 | —CH₂CH₂OH | —Cl | (DMSO-D6, 400 MHz): δ = 7.57 (d, 1H), 7.53 (d, 1H), 7.46 (d, 1H), 5.11 (t, 1H), 4.49 (s, 1H), 3.77 (m, 2H), 3.56 (m, 2H), 2.24 (s, 6H) ppm | 4-(3-chloro-1H-indazol-5-yl)-1,4-dihydro-1-(2-hydroxyethyl)-2,6-dimethyl-3,5-pyridinedicarbonitrile |

TABLE 7-continued

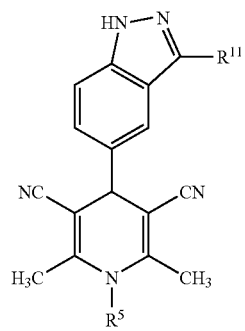

| Cpd No. | R⁵ | R¹¹ | 1H NMR | Name |
|---|---|---|---|---|
| 298 | —CH₃ | —Cl | (DMSO-D6, 400 MHz): δ = 7.42 (d, 1H), 7.39 (s, 1H), 7.07 (d, 1H), 4.32 (s, 1H), 3.00 (m, 1H), 2.45 (s, 3H), 2.34 (s, 6H), 1.02 (m, 1H), 0.79 (m, 1H) ppm | 4-(3-chloro-1H-indazol-5-yl)-1,4-dihydro-1,2,6-trimethyl-3,5-pyridinedicarbonitrile |
| 299 | —CH₂CH₂OH | —NH₂ | (DMSO-D6, 400 MHz): δ = 11.40 (s, 1H), 7.51 (s, 1H), 7.21 (d, 1H), 7.15 (d, 1H), 5.37 (s, 2H), 4.28 (s, 1H), 3.20 (s, 3H), 2.04 (s, 6H) ppm | 4-(3-amino-1H-indazol-5-yl)-1,4-dihydro-1-(2-hydroxyethyl)-2,6-dimethyl-3,5-pyridinedicarbonitrile |
| 300 | -cyclopropyl | —H | (DMSO-D6, 400 MHz): δ = 8.04 (s, 1H), 7.52 (d, 1H), 7.47 (s, 1H), 7.10 (d, 1H), 4.36 (s, 1H), 2.97 (m, 1H), 2.33 (s, 6H), 1.01 (m, 1H), 0.79 (m, 1H) ppm | 1-cyclopropyl-1,4-dihydro-4-(1H-indazol-5-yl)-2,6-dimethyl-3,5-pyridinedicarbonitrile |
| 301 | -cyclopropyl | —CH₃ | (DMSO-D6, 400 MHz): δ = 7.42 (d, 1H), 7.39 (s, 1H), 7.07 (d, 1H), 4.32 (s, 1H), 3.00 (m, 1H), 2.45 (s, 3H), 2.34 (s, 6H), 1.02 (m, 1H), 0.79 (m, 1H) ppm | 1-cyclopropyl-1,4-dihydro-2,6-dimethyl-4-(3-methyl-1H-indazol-5-yl)-3,5-pyridinedicarbonitrile |
| 302 | ![propargyl] | —H | (DMSO-D6, 400 MHz): δ = 8.06 (s, 1H), 7.59 (s, 1H), 7.54 (d, 1H), 7.26 (d, 1H), 4.53 (s, 2H), 4.45 (s, 1H), 3.62 (s, 1H), 2.32 (s, 6H) ppm | 1,4-dihydro-4-(1H-indazol-5-yl)-2,6-dimethyl-1-(2-propynyl)-3,5-pyridinedicarbonitrile |
| 303 | -cyclopropyl | —NH₂ | (DMSO-D6, 400 MHz): δ = 11.39 (s, 1H), 7.33 (s, 1H), 7.19 (d, 1H), 6.99 (d, 1H), 5.33 (s, 2H), 4.21 (s, 1H), 2.98 (m, 1H), 2.35 (s, 6H), 1.00 (m, 1H), 0.80 (m, 1H) ppm | 4-(3-amino-1H-indazol-5-yl)-1-cyclopropyl-1,4-dihydro-2,6-dimethyl-3,5-pyridinedicarbonitrile |
| 306 | —CH₃ | —CH₃ | (DMSO-D6, 400 MHz): δ = 12.67 (br s, 1H), 7.50 (s, 1H), 7.48 (d, 1H), 7.26 (d, 1H), 4.44 (s, 1H), 3.21 (s, 3H), 2.48 (s, 3H), 2.24 (s, 6H) ppm | 1,4-dihydro-1,2,6-trimethyl-4-(3-methyl-1H-indazol-5-yl)-3,5-pyridinedicarbonitrile |

TABLE 8

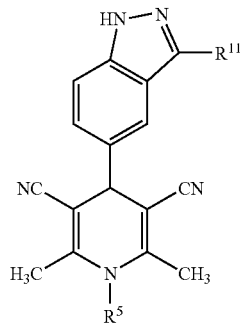

| Cpd No. | R⁵ | R¹¹ | 1H NMR | Name |
|---|---|---|---|---|
| 307 | —H | (morpholinylethyl-aminomethyl group) | (DMSO-D6, 300 MHz): δ = 11.46 (br s, 1H), 9.50 (br s, 1H), 7.56 (s, 1H), 7.25 (d, 1H), 7.17 (dd, 1H), 5.93 (t, 1H), 4.40 (s, 1H), 3.60 (m, 4H), 3.40 (partially obscured by solvent, 2H), 2.59 (t, 2H), 2.44 (m, 4H), 2.05 (s, 6H) ppm | 1,4-dihydro-2,6-dimethyl-4-[3-[[2-(4-morpholinyl)ethyl]amino]-1H-indazol-5-yl]-3,5-pyridinedicarbonitrile |
| 308 | —H | —NHCH₂CH₂NH₂ | (DMSO-D6, 300 MHz): δ = 11.38 (br s, 1H), 9.46 (br s, 1H), 7.52 (s, 1H), 7.20 (d, 1H), 7.12 (dd, 1H), 5.93 (t, 1H), 4.34 (s, 1H), 3.21 (m, 2H), 2.75 (t, 2H), 2.01 (s, 6H) ppm | 4-[3-[(2-aminoethyl)amino]-1H-indazol-5-yl]-1,4-dihydro-2,6-dimethyl-3,5-pyridinedicarbonitrile |
| 309 | —H | (pyrrolidinylethyl-aminomethyl group) | (DMSO-D6, 300 MHz): δ = 11.39 (br s, 1H), 9.45 (br s, 1H), 7.52 (s, 1H), 7.20 (d, 1H), 7.11 (dd, 1H), 5.90 (t, 1H), 4.34 (s, 1H), 3.32 (partially obscured by solvent, 2H), 2.64 (t, 2H), 2.00 (s, 6H), 1.65 (m, 4H) ppm [remaining 4H obscured by solvent] | 1,4-dihydro-2,6-dimethyl-4-[3-[[2-(1-pyrrolidinyl)ethyl]amino]-1H-indazol-5-yl]-3,5-pyridinedicarbonitrile |

Biological Example 1 c-MET Receptor Tyrosine Kinase Homogeneous Time Resolved Fluorescence Assay Recombinant c-Met kinase domain (amino acids 960-1390) was produced in a baculovirus expression vector as an N-terminal His-tagged fusion protein and purified on a NiNTA column. The resulting purified enzyme was then used in the following c-Met Homogeneous Time Resolved Fluorescence assay (HTRF) to find compounds of the invention and to perform initial activity determinations. Specifically, this assay measures the ability of compounds of the invention to inhibit the phosphorylation of a randomly synthesized, biotinylated heterocopolymeric polypeptide composed of glutamic acid and tyrosine, with an average length of 100 aa. The assay analyzes the amount of phosphorylated polypeptide produced.

The enzymatic phosphorylation of the biotinylated heterocopolymeric polypeptide was performed in a black 384-well plate at ambient temperature in a reaction mixture containing 50 mM HEPES (pH 7.4), 5 mM $MgCl_2$, 5 mM $MnCl_2$, 0.01% Tween-20, and 2 mM DTT, 300 µM recombinant human c-MET kinase enzyme domain, 37 nM biotinylated heterocopolymeric polypeptide composed of glutamic acid and tyrosine, 20 µM ATP, 1% DMSO in the absence or presence of a compound of the invention. The reaction was stopped after a 20-minute incubation by the addition of 80 mM EDTA.

The formation of phosphorylated heterocopolymeric, biotinylated polypeptide was quantified with the HTRF assay technology using an anti-phosphotyrosine antibody, PT66, conjugated to europium cryptate, mixed with a streptavidin-XL665 conjugate. Reduced or inhibited phosphorylation of the heterocopolymeric, biotinylated polypeptide prevents the anti-phosphotyrosine antibody from binding to the peptide, resulting in a loss of energy transfer to the streptavidin-XL665 conjugate.

Following the 384-well enzymatic phosphorylation reaction outlined above, the detection of phosphorylated heterocopolymeric, biotinylated polypeptide was performed by dilution of the stopped reaction mixture 2-fold with 50 mM HEPES (pH 7.0), 500 mM KF, 0.1% BSA, streptavidin-XL665 (20 nM), and anti-phosphotyrosine antibody PT66-crypate conjugate (6.4 ng/well) and incubation for four hours at ambient temperature. Plates were read in an Envision plate reader (PerkinElmer Life and Analytical Sciences, Inc., MA) simultaneously at 620 nm and 665 nm to obtain signal ratios of 665 nm/620 nm. Results of energy transfer were expressed as signal ratios of 665 nm/620 nm. Negative controls were samples without recombinant c-MET or c-MET treated with 100 mM EDTA.

For determination of $IC_{50}$ values of particular compounds of the invention, eight serially diluted compound concentrations (at 1:3.16 dilution) were used in the assay. Controls without a compound of the invention or with a reference compound were run in parallel in the same assay plate.

Compounds of the invention, when tested in this assay, demonstrated the ability to inhibit c-MET tyrosine kinase activity at $IC_{50}$ values of less than 100 µM, preferably at less than 1 µM.

Biological Example 2 c-Met Receptor Tyrosine Kinase Homogeneous Time Resolved Fluorescence Assay (Alternative Format)

N-terminally His6-tagged recombinant kinase domain of the human c-Met (amino acids 960-1390) expressed in insect cells (SF21) and purified by Ni-NTA affinity chromatography and consecutive size exclusion chromatography (Superdex 200) was used. Alternatively commercially available c-Met from Millipore can be used. As substrate for the kinase reaction the biotinylated poly-Glu,Tyr (4:1) copolymer (#61GT0BLC) from Cis Biointernational (Marcoule, France) was used.

For the assay 50 nL of a 100 fold concentrated solution of the test compound in DMSO was pipetted into a black low volume 384 well microtiter plate (Greiner Bio-One, Frickenhausen, Germany), 2 µL of a solution of cMet in assay buffer [25 mM Hepes/NaOH pH 7.5, 5 mM $MgCl_2$, 5 mM $MnCl_2$, 2 mM dithiothreitol, 0.1% (v/v) Tween20 (Sigma), 0.1% (w/v) bovine serum albumin] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (2.27 µg/mL=>final conc. in the 5 µl assay volume is 1.36 µg/mL [~30 nM]) in assay buffer and the resulting mixture was incubated for a reaction time of 30 min at 22° C. The concentration of c-Met in the assay was adjusted depending on the activity of the enzyme lot and was appropriately chosen to have the assay in the linear range; typical enzyme concentrations were in the range of about 0.03 nM (final conc. in the 5 µL assay volume). The reaction was stopped by the addition of 5 µL of a solution of HTRF detection reagents (40 nM streptavidine-XLent and 2.4 nM PT66-Eu-Chelate, an europium-chelate labelled anti-phospho-tyrosine antibody from Perkin Elmer) in an aqueous EDTA-solution (100 mM EDTA, 0.2% (w/v) bovine serum albumin in 50 mM HEPES/NaOH pH 7.5). The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM; dilution series prepared before the assay at the level of the 100 fold conc. stock solutions by serial 1:3 dilutions), in duplicate for each concentration, and $IC_{50}$ values were calculated by a 4 parameter fit using an inhouse software.

Compounds of the invention, when tested in this assay, demonstrated the ability to inhibit c-Met tyrosine kinase activity at $IC_{50}$ values of less than 10 µM, preferably at less than 1 µM.

Biological Example 3 c-Met Cell-Based Autophosphorylation Assays

To directly ascertain the cell-based activity of inhibitors, compounds were profiled for their ability to inhibit c-Met tyrosine kinase autophosphorylation in Western and ELISA formats. For the Western assay, A549 lung carcinoma cells or U373 glioblastoma cells were plated in Ham's F12 with 10% FBS in 6-well plates at $2.2 \times 10^5$ cells per well. The cells were incubated in a humid atmosphere of 95% air and 5% $CO_2$ for overnight. The following day, the cells were washed 2× with PBS and the medium was replaced with Ham's F12 without serum. After 48 hours, the cells were treated with compound for two hours. Prior to incubation, compounds were dissolved in 100% DMSO and added to cells so that the final DMSO concentration was 1%. Subsequently, HGF was added to the cells to a final concentration of 20 ng/mL for 10 minutes. The cells were then lysed in gel sample buffer containing 1 mM NaF, 200 µM NaOV and 2.5% µ-mercaptoethanol. The lysates were then subjected to SDS-PAGE and electrophoretic transfer to nitrocellulose membrane. The resulting membranes were then probed with phospho-c-Met specific antisera (Upstate anti-phospho-c-Met 1234, 1235; Cat #07-211) diluted 1:5000 in 2% milk-PBST and incubated overnight at 4° C. with shaking. The next day the membranes were washed 4× with water at room temperature and incubated with secondary antibody (Amersham anti-rabbit cat #NA934V) diluted 1:5000 in 2% milk-PBST. After two hours' incubation at room temperature, the membranes were washed 1× with PBST and 5× with water. Finally, the membranes were processed with a Pierce Dura or Femto kit according to the manufactures instructions.

For analysis of c-Met autophosphorylation by ELISA, lysates treated similar to above were processed using a c-Met phospho-specific ELISA kit from Biosource International (cat#KH00281) according to the manufacturers instructions and using antisera supplied in the kit. ELISA plates were read at 450 nM. In general, the ELISA assay performed better when A549 lung carcinoma cells were used due to higher levels of phospho-c-Met in this cell line relative to U373.

Compounds of the invention, when tested in this assay, demonstrated the ability to inhibit c-Met cell-based autophosphorylation at $IC_{50}$ values less than 20 µM and preferably less than 1 µM.

It will also be apparent to the person skilled in the art that c-Met cell-based autophosphorylation may also be assessed by using other assay formats, such as, for example, a Meso Scale assay (assays, kits, reagents and technical support are available from Meso Scale Discovery, 9238 Gaither Road, Gaithersburg, Md. 20877, USA).

Biological Example 4

Cell-Based Down-Stream Signaling Assays

To verify the cell-based activity of compounds identified in high-throughput screening described above, inhibition of downstream signaling events from the c-Met receptor was examined. We found that the activated c-Met signal transduction apparatus induced c-Fos promoter activity. We then developed an assay to measure the effect of HGF on c-Fos transcription by real-time RT-PCR in the presence and absence of c-Met small-molecule inhibitors. This assay allows for much more precise quantitation than the Western assay described above and proved somewhat more sensitive than the ELISA assay. Therefore, while all compounds are profiled to ensure qualitative inhibition of cellular c-Met kinase activity, we have relied on the c-Fos transcriptional activation assay as a more accurate estimate of cell-based compound $IC_{50}$. In brief, U373 glioblastoma cells were seeded at $5 \times 10^4$ cells/well in a 24-well dish and incubated overnight in culture medium comprised of MEM, 10% FBS, 2 mM glutamine, 0.1 mM non-essential amino acids and 1 mM sodium pyruvate at 37° C. in a humid atmosphere of 95% air and with 5% $CO_2$. Subsequently, the cells were pre-incubated with compound for two hours in serum-free medium comprised of Ham's F12, 2 mM glutamine, 0.1 mM non-essential amino acids and 1 mM sodium pyruvate. Compounds used for treatment were diluted in log increments in 100% DMSO and 15 µL of the resulting solution was added to 1.5 mL of the SF incubation medium. Following pre-incubation with compound, cells were treated with HGF (hepatocyte growth factor) for 30 minutes at a final concentration of 10 ng/mL in triplicate. In the absence of inhibitor, such treatment resulted in a 40-fold increase in c-Fos transcription. After incubation with HGF, RNA was isolated from the cells by using an mRNA Catcher Kit™ from Invitrogen. Subsequently, c-Fos mRNA levels were quantified by using a PCR thermocycler from Stratagene (MX3000P) and reagents from Applied Biosystems (Taqman 2× universal PCR master mix cat #58004002-01; MuLV reverse transcriptase cat#N808-0018; and RNase inhibitor cat #N808-0119). Primers and probe set specific for c-Fos were also purchased from Applied Biosystems (cat #Hs99999.140_m1). For normalizing the quantity of input mRNA, we determined the level of GAPDH in each sample using a primer probe set from Applied Biosystems (cat #Hs99999905_m1).

Compounds of the invention, when tested in this assay, demonstrated the ability to inhibit HGF-mediated induction of c-Fos transcription at $IC_{50}$ values less than 20 µM and preferably less than 1 µM. Final $IC_{50}$ determinations had a Hill slope of between 0.5 and 3.5.

Biological Example 5

Cell-Based Efficacy Assays

Two cell-based efficacy assays were used for compound profiling: proliferation on plastic and anchorage-independent growth on soft agar. These assays were employed as a final measure of compound effect on a cell-based phenotype that would be directly relevant to the final desired profile of compound activity: inhibition of tumor growth.

For the proliferation assay, MKN45 gastric carcinoma cells were used. These cells have constitutively active c-Met, and active inhibitors against the kinase had a profound effect on the proliferation of these cells. For the assay, cells were plated in serum-free F12 at a density of 15,000 cells/well in collagen IV-coated 96-well plates (BD Biocoat #354429). The cells were then incubated in a humid atmosphere of 95% air and 5% $CO_2$ for 30 hours. Compounds of the invention were then diluted in 100% DMSO and added to the cells in quadruplicate, with a final DMSO concentration of 1%. Cells with the test compounds were returned to the incubator for overnight. The next day, the cells were processed for BrdU incorporation using a Cell Proliferation ELISA BrdU calorimetric kit (Roche #11-647-229-001). BrdU labeling solution was prepared according to the manufacturer's instructions and incubated with the cells for six hours. The labeling solution was then removed and the plates were dried at 60° C. for one hour. Substrate provided by the manufacturer was then added to the plates and incubated for 30 min. The plates were then read at 370 nM.

Compounds of the invention, when tested in this assay, demonstrated the ability to inhibit MKN45 cell proliferation at $IC_{50}$ values less than 20 µM and preferably less than 1 µM.

For the soft agar assay, U373 glioblastoma cells were used. When cultured in the below-mentioned soft agar medium, these cells do not form colonies unless HGF is added. Therefore, this assay measures the ability of compounds to inhibit HGF-mediated colony formation. To perform the assay, briefly, melted 3% agar was equilibrated to 48° C. and then mixed to a final concentration of 0.5% agar with SF media, composed of Ham's F12, 0.1 mM non-essential amino acids and 1 mM sodium pyruvate. Fetal bovine serum was added to a final concentration of 5%. The resulting solution was added to 35-mm dishes and allowed to solidify. A separate aliquot of melted 3% agar was then equilibrated to 42° C. and added to SF media plus 5% fetal bovine serum to a final concentration of 0.3% agar. The resulting top layer of agar was maintained at 42° C. until cells were finally added. To prepare the cellular inoculum, U373 cells were trypsinized and washed 2 times with PBS. The cells were then gently passed through an 18-gauge syringe needle to eliminate any clusters of adherent cells. The cells were then resuspended in fresh SF medium to a final concentration of $1.25 \times 10^5$ mL. An equal volume of the cell suspension was then added to 0.5 mL of the agar top layer. The cells were then treated with and without HGF to a final concentration of 20 ng/mL HGF. In addition, various concentrations of c-Met inhibitors were added to this solution. The resulting mixture was then added to the previously prepared agar plates and allowed to solidify. The plates were subsequently incubated at 37° C. in a humid atmosphere of 95% air and 5% $CO_2$. Every seven days, additional aliquots of top agar layers were prepared as above, without cells, to replenish both compound and HGF. After three weeks, the resulting colonies were stained with 0.5% Nitro Blue Tetrazolium and then quantified using a Bio Rad gel imager.

Compounds of the invention, when tested in this assay, demonstrated the ability to inhibit HGF induced U373 colony formation at $IC_{50}$ values less than 20 µM and preferably less than 1 µM.

Biological Example 6

In Vivo Pharmacodynamic Assay and Efficacy of c-Met Inhibitor in Female Nude Mice Bearing s.c. MKN-45 Gastric Carcinoma Tumors To demonstrate that compounds of the invention were efficacious against human gastric cancer, they were tested for efficacy in an MKN-45 tumor xenograft animal model. Animals used in this analysis were female athymic (nu/nu) mice (Simonsen, Gilroy, Calif.) at 6-8 weeks old were implanted with a small fragment (~5 $mm^3$) by s.c. insertion of trocar needle. A colony of host mice was initially created by s.c. injection of $5 \times 10^6$ freshly trypsinized MKN-45 (from American Type Culture Collection, Manassas, Va.) tissue culture cells and serially transferred in vivo for no more than 10 passages. All animal experiments were performed in accordance with AALAC national and international standards and were approved by Berlex (Richmond, Calif.) IACUC (institutional animal care and use committee). Tumor volume was estimated by caliper measurement taken in two perpendicular diameters and calculated by the formula [(L×W×W)÷2]=V (where W=width, L=length and V=volume). Animal body weight was measured at least twice a week and reported as the percent body weight loss or gain by comparison to the day when dosing began. Any animal deaths were recorded as "compound related" or "not compound related" by subjective observation of the animal technician. Animals were identified by s.c. insertion of a transponder (BMDS, Seaford, Del.) which allowed electronic transfer of body weight and caliper measurements directly to an Excel file. At study end, animals were anesthetized with 2-4% isoflurane, blood was extracted by cardiac tap, and tumors were excised, weighed and snap frozen in liquid nitrogen.

For administration, compounds of the invention were dissolved in Saline/PEG400 (60%/40%) at 10 mg/mL immediately before use and were applied p.o. (per os) by disposable oral gavage needle (Popper & Sons, Inc., New Hyde Park, N.Y.) twice daily (BID) at a dose volume of approximately 5 mL/kg (125 μL, assuming an average body weight of 25 g per mouse). Dosing began 2-3 weeks after trocar implantation when average tumor volume in groups (N=20) was ~300 mm$^3$ and continued until study end.

To measure the concentration of compounds of the invention in plasma, blood was collected from the heart into microtainer plasma separator tubes with lithium heparin (Beckton Dickinson, Franklin Lakes, N.J.), centrifuged at 5,000 rpm for 10 minutes at 4° C., and the plasma stored at −80° C. In addition, the concentration of compound was also determined in tumors homogenates. For this analysis, tumors were thawed by adding 3-fold excess (30.0 μL for each 100 mg wet weight) of 1% Triton X-100 and homogenizing first in an Omni tissue homogenizer with disposable probes (Omni International, Marietta, Ga.) then in a FastPrep Bio101 (Savant) shaking machine (Q-biogen Inc, Carlsbad, Calif.). Compound concentration in plasma or whole tumor homogenate was analyzed by LC/MS/MS (API 3000, Applied Biosystems, Foster City, Calif.) on a C18A column (Varian Polaris) in a 10%-80% gradient of water to acetonitrile (in 0.1% formic acid), after precipitation of protein by 4:1 addition of acetonitrile in 0.1% formic acid.

For pharmacodynamic analysis of c-Met phosphorylation in vivo in compound-treated animals, isolated tumors were thawed by adding 5-fold excess of extraction buffer [T-PER (Pierce, Rockford, Ill.), 5 mM sodium vanadate (Aldrich), protease inhibitors (Roche Diagnostics GmbH, Mannheim, Germany), and 1 mM PMSF (Sigma, St Louis, Mo.)] and homogenizing first in an Omni tissue homogenizer with disposable probes (Omni International, Marietta, Ga.), then in a FastPrep Bio101 (Savant) shaking machine (Q-biogen Inc, Carlsbad, Calif.). The supernatant from 10,000 rpm 10 minute 4° C. centrifugation was stored at −80° C. Protein concentration was measured by BCA analysis (Pierce, Rockford, Ill.) and read at 562 nm in Versamax plate reader (Molecular Devices, Carlsbad, Calif.). Total c-Met and Phospho-c-Met was quantified by c-Met[pYpYpY1230/1234/1235] phospho ELISA kit and total c-Met ELISA kit (BioSource Intl., Camarillo, Calif.; Invitrogen, Carlsbad, Calif.).

It will also be apparent to the person skilled in the art that c-Met cell-based autophosphorylation may also be assessed by using other assay formats, such as, for example, a Meso Scale assay (assays, kits, reagents and technical support are available from Meso Scale Discovery, 9238 Gaither Road, Gaithersburg, Md. 20877, USA).

To further illustrate the utility of the compounds of the present invention, Table 7 below presents biological activity of representative examples according to the assays described in Biological Assay 1 and/or Biological Assay 2.

| Cpd No. | Biological Activity in Biological Example 1 and/or 2 |
|---|---|
| 10 | ++ |
| 12 | + |
| 17 | + |
| 21 | ++ |
| 22 | ++ |
| 23 | + |
| 26 | ++ |
| 27 | + |
| 32 | ++ |
| 34 | + |
| 38 | + |
| 43 | +++ |
| 45 | + |
| 47 | + |
| 51 | ++ |
| 57 | + |
| 58 | ++ |
| 60 | + |
| 61 | ++ |
| 62 | + |
| 63 | ++ |
| 65 | ++ |
| 66 | ++ |
| 68 | ++ |
| 72 | ++ |
| 76 | ++ |
| 80 | +++ |
| 81 | +++ |
| 82 | +++ |
| 83 | + |
| 84 | ++ |
| 85 | + |
| 86 | +++ |
| 87 | +++ |
| 88 | +++ |
| 89 | +++ |
| 91 | +++ |
| 92 | ++ |
| 93 | +++ |
| 94.2 | +++ |
| 95 | +++ |
| 99.1 | +++ |
| 99.2 | +++ |
| 103.1 | +++ |
| 103.2 | +++ |
| 105 | +++ |
| 106.1 | +++ |
| 110 | ++ |
| 111 | +++ |
| 114.1 | +++ |
| 118 | +++ |
| 119 | +++ |
| 120 | +++ |
| 121 | +++ |
| 123 | + |
| 124 | +++ |
| 125 | +++ |
| 127 | + |
| 128 | +++ |
| 129 | +++ |
| 130 | + |
| 131 | + |
| 133 | +++ |
| 135 | +++ |
| 136 | +++ |
| 137 | +++ |
| 138 | +++ |
| 139 | +++ |
| 140 | +++ |
| 141 | + |
| 142 | +++ |
| 143 | +++ |
| 144 | +++ |
| 145 | +++ |

| Cpd No. | Biological Activity in Biological Example 1 and/or 2 |
|---|---|
| 147 | +++ |
| 148 | +++ |
| 149 | +++ |
| 150 | +++ |
| 151 | +++ |
| 152 | +++ |
| 153 | + |
| 155 | +++ |
| 156 | +++ |
| 157 | +++ |
| 158 | +++ |
| 159 | +++ |
| 160 | +++ |
| 161 | +++ |
| 163 | +++ |
| 164 | +++ |
| 165.1 | +++ |
| 166 | +++ |
| 167.1 | +++ |
| 168 | +++ |
| 169 | + |
| 170 | +++ |
| 172 | +++ |
| 173 | +++ |
| 174 | +++ |
| 175 | +++ |
| 176 | + |
| 177 | +++ |
| 178 | +++ |
| 189 | + |
| 190 | ++ |
| 191 | ++ |
| 192 | +++ |
| 204 | +++ |
| 219 | +++ |
| 229 | ++ |
| 230 | ++ |
| 232 | + |
| 233 | + |
| 234 | ++ |
| 235 | ++ |
| 236 | ++ |
| 238 | + |
| 239 | + |
| 240 | + |
| 246 | ++ |
| 249 | +++ |
| 250 | +++ |
| 251 | + |
| 252 | +++ |
| 253 | +++ |
| 255 | +++ |
| 257 | +++ |
| 258 | +++ |
| 259 | +++ |
| 260 | +++ |
| 261 | +++ |
| 264 | +++ |
| 265 | +++ |
| 266 | +++ |
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 278 | +++ |
| 280 | +++ |
| 281 | +++ |
| 282 | +++ |
| 284 | + |
| 288 | +++ |
| 289 | +++ |
| 290 | +++ |
| 292 | +++ |
| 293 | +++ |
| 294 | +++ |
| 297 | +++ |
| 298 | +++ |
| 299 | +++ |
| 301 | +++ |
| 302 | +++ |
| 304 | +++ |
| 306 | +++ |
| 307 | +++ |
| 308 | +++ |
| 309 | +++ |

Key:
"+++" = mean $IC_{50}$ in Biological Example 1 and/or Biological Example 2 is less than 100 nM;

"++" = mean $IC_{50}$ in Biological Example 1 and/or Biological Example 2 is less than 500 nM but greater than 100 nM;

"+" = mean $IC_{50}$ in Biological Example 1 and/or Biological Example 2 is less than 2.5 μM but greater than 500 nM;

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 60/875,124, filed Dec. 14, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound having the formula

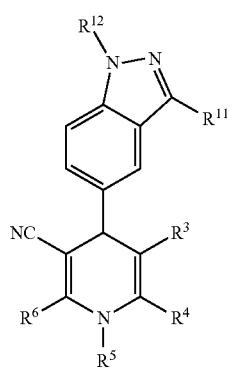

wherein
  $R^3$ is a cyano group;
  $R^4$ is $C_{1-3}$alkyl or haloalkyl;
  $R^5$ is hydrogen;
  $R^6$ is $C_{1-3}$alkyl;
  $R^{11}$ is $C_{1-3}$alkyl;
and
  $R^{12}$ is hydrogen,
or a pharmaceutically acceptable salt thereof.

2. A compound according to claim 1, wherein $R^4$ is $C_{1-3}$alkyl.

3. A compound according to claim 1, wherein $R^4$ is methyl.

4. A compound according to claim 1, wherein $R^6$ is methyl.

5. A compound according to claim 1, wherein $R^{11}$ is methyl.

6. A compound according to claim 1, wherein $R^4$ and $R^6$ are $C_{1-3}$alkyl.

7. A compound according to claim 1, wherein $R^4$ and $R^6$ are methyl.

8. A compound according to claim 1, wherein $R^6$ and $R^{11}$ are methyl.

9. A compound according to claim 1, which is 1,4-dihydro-2,6-dimethyl-4-(3-methyl-1H-indazol-5-yl)-3,5-pyridinedicarbonitrile, or a pharmaceutically acceptable salt thereof.

10. A compound having the formula

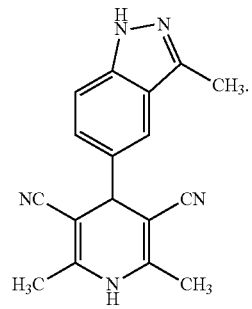

* * * * *